US011512144B2

(12) United States Patent
Babb et al.

(10) Patent No.: US 11,512,144 B2

(45) **Date of Patent: *Nov. 29, 2022**

(54) COMPOSITIONS AND METHODS FOR MAKING ANTIBODIES BASED ON USE OF AN EXPRESSION-ENHANCING LOCI

(71) Applicant: REGENERON PHARMACEUTICALS, INC., Tarrytown, NY (US)

(72) Inventors: Robert Babb, River Edge, NJ (US); Darya Burakov, Tarrytown, NY (US); Gang Chen, Yorktown Heights, NY (US); James P. Fandl, LaGrangeville, NY (US); Yu Zhao, Williston Park, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 830 days.

This patent is subject to a terminal disclaimer.

(21) Appl. No.: 16/095,084

(22) PCT Filed: Apr. 20, 2017

(86) PCT No.: PCT/US2017/028555

§ 371 (c)(1), (2) Date: Oct. 19, 2018

(87) PCT Pub. No.: WO2017/184832

PCT Pub. Date: Oct. 26, 2017

(65) Prior Publication Data

US 2019/0233544 A1 Aug. 1, 2019

Related U.S. Application Data

(60) Provisional application No. 62/325,400, filed on Apr. 20, 2016.

(51) Int. Cl.

| | |
|---|---|
| ***C07K 16/46*** | (2006.01) |
| ***C07K 16/00*** | (2006.01) |
| ***C12N 15/90*** | (2006.01) |
| ***C12N 15/85*** | (2006.01) |

(52) U.S. Cl.

CPC ............ *C07K 16/468* (2013.01); *C07K 16/00* (2013.01); *C12N 15/85* (2013.01); *C12N 15/907* (2013.01)

(58) Field of Classification Search

None

See application file for complete search history.

(56) References Cited

U.S. PATENT DOCUMENTS

| | | | |
|---|---|---|---|
| 4,634,665 | A | 1/1987 | Axel et al. |
| 4,656,134 | A | 4/1987 | Ringold |
| 6,800,457 | B2 | 10/2004 | Koduri et al. |
| 7,183,076 | B2 | 2/2007 | Arathoon et al. |
| 8,389,239 | B2 | 3/2013 | Chen et al. |
| 8,586,713 | B2 | 11/2013 | Davis et al. |
| 2005/0142562 | A1 | 6/2005 | Zhu et al. |
| 2010/0105042 | A1 | 4/2010 | Taylor et al. |
| 2013/0004946 | A1 | 1/2013 | Chesnut et al. |
| 2014/0088295 | A1 | 3/2014 | Smith et al. |
| 2014/0134719 | A1 | 5/2014 | Deshpande et al. |
| 2014/0179547 | A1 | 6/2014 | Fischer et al. |
| 2014/0308285 | A1 | 10/2014 | Yan et al. |
| 2015/0167020 | A1 | 6/2015 | Rance et al. |
| 2015/0218276 | A1 | 8/2015 | Chen et al. |
| 2015/0266966 | A1 | 9/2015 | Smith et al. |
| 2016/0115502 | A1 | 4/2016 | Shen et al. |

FOREIGN PATENT DOCUMENTS

| | | | |
|---|---|---|---|
| CN | 102575264 | A | 7/2012 |
| EA | 201790698 | A1 | 1/2018 |
| EP | 1 870 459 | A1 | 12/2007 |
| JP | 2009-539349 | A | 11/2009 |
| JP | 2012-531439 | A | 12/2012 |
| KR | 10-2015-0110571 | | 10/2015 |
| TW | 201514206 | A | 4/2015 |
| WO | 03/101189 | A1 | 12/2003 |
| WO | 2004/046340 | A2 | 6/2004 |
| WO | 2007/110205 | A2 | 10/2007 |
| WO | 2007/143168 | A2 | 12/2007 |
| WO | 2008/119353 | A1 | 10/2008 |
| WO | 2008/151219 | A1 | 12/2008 |
| WO | 2009/089004 | A1 | 7/2009 |
| WO | 2010/141478 | A1 | 12/2010 |
| WO | 2010/151792 | A1 | 12/2010 |
| WO | 2011/034605 | A2 | 3/2011 |
| WO | 2011/131746 | A2 | 10/2011 |
| WO | 2013/181253 | A1 | 12/2013 |

(Continued)

OTHER PUBLICATIONS

Araki K. et al., "Site-Directed Integration of the Cre Gene Mediated by Cre Recombinase Using a Combination of Mutant Lox Sites", Nucleic Acids Research 30(19):e103 (2002).

(Continued)

*Primary Examiner* — Michael D Burkhart

(74) *Attorney, Agent, or Firm* — Scully, Scott, Murphy & Presser, P.C.; Todd R. Samelman

(57) ABSTRACT

This invention relates to site-specific integration and expression of recombinant proteins in eukaryotic cells. In particular, the invention includes compositions and methods for improved expression of antigen-binding proteins including monospecific and bispecifc antibodies in eukaryotic cells, particularly Chinese hamster (*Cricetulus griseus*) cell lines, by employing multiple expression-enhancing locus.

43 Claims, 7 Drawing Sheets

Specification includes a Sequence Listing.

(56) References Cited

FOREIGN PATENT DOCUMENTS

| | | | |
|---|---|---|---|
| WO | 2013/190032 | A1 | 12/2013 |
| WO | 2014/022540 | A1 | 2/2014 |
| WO | 2014/121087 | A1 | 8/2014 |
| WO | 2016/064999 | A1 | 4/2016 |
| WO | 2017053856 | A1 | 3/2017 |

OTHER PUBLICATIONS

Baser B. et al., "A Method for Specifically Targeting Two Independent Genomic Integration Sites for Co-Expression of Genes in CHO Cells", Methods 95:3-12 (2016), together with Supplementary Materials.
Boch J. et al., "Breaking the Code of DNA Binding Specificity of TAL-Type III Effectors", Science 326:1509-1512 (Dec. 11, 2009).
Chen H. et al., "Cut Site Selection by the Two Nuclease Domains of the Cas9 RNA-Guided Endonuclease", The Journal of Biological Chemistry 289(19): 13284-13294 (May 9, 2014).
Crawford Y. et al., "Fast Identification of Reliable Hosts for Targeted Cell Line Development from a Limited-Genome Screening Using Combined C31 Integrase and CRE-Lox Technologies", Biotechnol. Prog. 29(5): 1307-1315 (2013).
Doerner A. et al., "Therapeutic Antibody Engineering by High Efficiency Cell Screening", FEBS Letters 588:278-287 (2014).
Frenzel A. et al., "Expression of Recombinant Antibodies", Frontiers in Immunology 4(217):1-20 (Jul. 2013).
Kawabe Y. et al., "Repeated Integration of Antibody Genes into a Pre-Selected Chromosomal Locus of CHO Cells Using an Accumulative Site-Specific Gene Integration System", Cytotechnology 64:267-279 (2012).
Kim S.K. et al., "Stable Reduction of Thymidine Kinase Activity in Cells Expressing High Levels of Anti-Sense RNA", 42:129-138 (Aug. 1985).
Klar M. et al., "Dominant Genomic Structures: Detection and Potential Signal Functions in the Interferon-Beta Domain", Gene 364:79-89 (2005).
Kontermann R.E et al., "Bispecific Antibodies", Drug Discovery Today 20(7):838-847 (Jul. 2015).
Kostelny S.A. et al., "Formation of a Bispecific Antibody by the Use of Leucine Zippers", The Journal of Immunology 148(5): 1547-1553 (Mar. 1, 1992).
Kriz A. et al., "A Plasmid-Based Multigene Expression System for Mammalian Cells", Nature Communications 1:120:DOI:10.1038 (2010).
Lai T. et al., "Advances in Mammalian Cell Line Development Technologies for Recombinant Protein Production", Pharmaceuticals 6:579-603 (2013).
Lattenmayer C. et al., "Identification of Transgene Integration Loci of Different Highly Expressing Recombinant CHO Cell Lines by FISH", Cytotechnology 51(3):171-182 (Nov. 15, 2006).
Li J. et al., "Analysis of IgG Heavy Chain to Light Chain Ratio With Mutant Encephalomyocarditis Virus Internal Ribosome Entry Site", Protein Engineering, Design & Selection 20(10):491-496 (2007).
Qiao J. et al., "Novel Tag-and-Exchange (RMCE) Strategies Generate Master Cell Clones With Predictable and Stable Transgene Expression Properties", J. Mol. Biol. 390:579-594 (2009).
Racher A., "Establishment of Cell Lines for Manufacturing Recombinant Antibodies", 2004, Lonza Presentation.
Szymczak A L et al., "Development of 2A Peptide-Based Strategies in the Design of Multicistronic Vectors", Expert Opinion Biol. Ther. 5(5):627-638 (2005).
Turan S. et al., "Recombinase-Mediated Cassette Exchange (RMCE)—A Rapidly-Expanding Toolbox for Targeted Genomic Modifications", Gene 515(1):1-27 (Feb. 1, 2013).
Turan S. et al., "Site-Specific Recombinases: From Tag-and-Target to Tag-and-Exchange-Based Genomic Modifications", The FASEB Journal 25:4088-4107 (2011).
Turan S. et al., "Multiplexing RMCE: Versatile Extensions of the Flp-Recombinase-Mediated Cassette-Exchange Technology", J. Mol. Biol. 402:52-69 (2010).
Wiberg F.C. et al., "Production of Target-Specific Recombinant Human Polyclonal Antibodies in Mammalian Cells", Biotechnology and Bioengineering 94(2):396-405 (Jun. 5, 2006).
Wilke S. et al., "Streamlining Homogeneous Glycoprotein Production for Biophysical and Structural Applications by Targeted Cell Line Development", PLoS One 6(12):e27829 (Dec. 2011).
Zboray K. et al., "Heterologous Protein Production Using Euchromatin-Containing Expression Vectors in Mammalian Cells", Nucleic Acids Research 43(16):e102 (Sep. 18, 2015).
Zhang L. et al., "Recombinase-Mediated Cassette Exchange (RMCE) for Monoclonal Antibody Expression in the Commercially Relevant CHOK1SV Cell Line", Biotechnology Progress 31(6):1645-1656 (Oct. 13, 2015).
Zhou C. et al., "Development of a Novel Mammalian Cell Surface Antibody Display Platform", mABS 2(5):508-518 (Sep./Oct. 2010).
International Search Report dated Jul. 5, 2017 received in International Application No. PCT/US2017/028555.
Japanese Notice of Reasons for Rejection dated Apr. 12, 2021 received in Japanese Patent Application No. 2018-552794, together with an English-language translation.
Korean Notice of Grounds for Preliminary Rejection dated Oct. 15, 2021 received in Korean Application No. 10-2018-7029365, together with an English-language translation.
English-language translation of Taiwanese Search Report dated Jul. 12, 2021 received in ROC Patent Application No. 106113298.
Chinese Office Action dated Dec. 1, 2021 received in Chinese Application No. 201780024557.0, together with an English-language translation.
Eurasian Office Action dated May 17, 2022 received in Eurasian Application No. 201892010, together with an English-language translation.

COMPOSITIONS AND METHODS FOR MAKING ANTIBODIES BASED ON USE OF AN EXPRESSION-ENHANCING LOCI

CROSS REFERENCE TO RELATED APPLICATION

This application claims the benefit of priority from U.S. Provisional Application No. 62/325,400, filed Apr. 20, 2016, the entire contents of which are incorporated herein by reference.

FIELD OF THE DISCLOSURE

This disclosure relates to site-specific integration and expression of recombinant proteins in eukaryotic cells. In particular, the disclosure relates to compositions and methods for improved expression of antigen-binding proteins (including monospecific and bispecifc antibodies) in eukaryotic cells, particularly Chinese hamster (*Cricetulus griseus*) cell lines, by employing expression-enhancing loci.

BACKGROUND ART

Cellular expression systems aim to provide a reliable and efficient source for the manufacture of a given protein, whether for research or therapeutic use. Recombinant protein expression in mammalian cells is a preferred method for manufacturing therapeutic proteins due to, for example, the ability of mammalian expression systems to appropriately post-translationally modify recombinant proteins.

Despite the availability of various expression systems, the challenge of efficient gene transfer and stability of the integrated gene for expression of a recombinant protein still exists. For long-term expression of a target transgene, one consideration is minimal disruption of cellular genes to avoid changes in the phenotype of the cell line.

Engineering stable cell lines to accommodate multiple genes for expression, such as multiple antibody chains as in multispecific antibodies, is particularly challenging. Wide variations in expression levels of integrated genes may occur. Integrating additional genies may lead to greater variation in expression and instability due to the local genetic environment (i.e., position effects). Expression systems for the production of multispecific antigen-binding proteins often requires the expression of two or more different immunoglobulin chains intended to pair as a specific multimeric format, and can often weigh in favor of homodimer production, rather than the desired heterodimer or multimer combination. Accordingly, there is a need in the art for improved mammalian expression systems.

SUMMARY OF THE DISCLOSURE

In one aspect, this disclosure provides a cell that contains multiple exogenous nucleic acids integrated site-specifically in two expression-enhancing loci wherein the multiple exogenous nucleic acids together encode an antigen-binding protein. The antigen-binding protein can be a bispecific antigen-binding protein, or a conventional monospecific antigen-binding protein.

In some embodiments, a cell is provided that contains a first exogenous nucleic acid integrated within a first enhanced expression locus, and a second exogenous nucleic acid integrated within a second enhanced expression locus; wherein the first and second exogenous nucleic acids together encode an antigen-binding protein.

In some embodiments, the first exogenous nucleic acid contains a nucleotide sequence encoding a first heavy chain fragment (HCF), and the second exogenous nucleic acid contains a nucleotide sequence encoding a first light chain fragment (LCF).

In some embodiments, the second exogenous nucleic acid further includes a nucleotide sequence encoding a second HCF (also HCF*). The first and second HCFs can be the same, or different as in a bispecific antigen-binding protein. Each HCF- or LCF-encoding nucleotide sequence can encode amino acids from a constant region. In some embodiments, the nucleotide sequence encoding the first HCF encodes a first CH3 domain, and the nucleotide sequence encoding the second HCF (HCF*) encodes a second CH3 domain. In some embodiments, the first and second CH3 domains can differ in at least one amino acid position, such as a position that results in different Protein A binding characteristics. In other embodiments, the nucleotide sequences encoding the first and second CH domains differ from each other in that one of the nucleotide sequences has been codon modified.

In some embodiments, the first exogenous nucleic acid (containing the first HCF-encoding nucleotide sequence) further comprises a nucleotide sequence encoding a second LCF. The second LCF can be the same as or different from the first LCF in the second exogenous nucleic acid.

In many of the embodiments of a cell provided herein, each of the nucleotide sequences encoding a HCF or LCF is operably linked to a promoter independently so that transcription of each HCF or LCF-encoding sequence is regulated separately.

In some embodiments, a first RRS and a second RRS are positioned 5' and 3', respectively, relative to the first exogenous nucleic acid, and a third RRS and a fourth RRS are positioned 5' and 3', respectively, relative to the second exogenous nucleic acid, wherein the first and second RRSs are different, and the third and fourth RRSs are different. Generally, the RRSs within a pair of RRSs flanking an exogenous nucleic acid are different to avoid unintended recombination and removal of the exogenous nucleic acid. In some embodiments, the first, second, third and fourth RRS are all different from each other.

In embodiments where the first exogenous nucleic acid in the first locus includes the first HCF-encoding nucleotide sequence, and the second exogenous nucleic acid in the second locus includes both the first LCF-encoding sequence and the second HCF-encoding sequence, a first additional RRS can be present between the nucleotide sequence encoding the first LCF and the nucleotide sequence encoding the second HCF. The additional RRS can be different from each of the first, second, third and fourth RRSs. In some embodiments, the first additional RRS is included between a promoter to which the selectable marker gene is operably linked, and the selectable marker gene, or the additional RRS may be included in a selectable marker gene, or within an intron of a selectable marker gene, that is present between the first LCF-encoding sequence and an HCF-encoding sequence, or between a first HCF-encoding sequence and a second HCF-encoding sequence.

In embodiments where the first exogenous nucleic acid in the first locus includes the first HCF-encoding nucleotide sequence and the second HCF-encoding nucleotide sequence, and the second exogenous nucleic acid in the second locus includes both the first LCF-encoding sequence and the second HCF-encoding sequence, a first RRS and a second RRS can be present at 5' and 3', respectively, relative to the first exogenous nucleic acid, and a third RRS and a fourth RRS can be present at 5' and 3', respectively, relative to the second exogenous nucleic acid, wherein the first and second RRSs are different, and the third and fourth RRSs are different. In some embodiments, the first and second HCFs are the same, and the first and second LCFs are the same, in which instances the RRSs can be engineered such that the first and third RRS are the same, and the second and fourth RRS are the same. In some embodiments, the first and second HCFs are different, and the first and second LCFs are the same, in which instances the RRSs can be engineered such that the first, second, third and fourth RRSs are all different from each other. Irrespective of whether the two HCFs are the same or different, an additional RRS can be present between the first LCF-encoding sequence and the second HCF-encoding sequence, and/or present between the second LCF encoding sequence and the first HCF-encoding sequence. The additional (middle) RRS is different from each of the first, second, third and fourth RRSs. The additional RRS can be included within a selectable marker gene, or within an intron of a selectable marker gene, placed between two HFC/LCF coding sequences.

In another aspect, cells are provided that contain pairs of RRSs integrated within two expression enhancing loci that can be used for integration of nucleic acids encoding antigen-binding proteins through RMCE.

In certain embodiments, cells are provided that contain pairs of RRSs integrated within two expression enhancing loci that can be used for simultaneous integration of nucleic acids encoding antigen-binding proteins through RMCE in the presence of a recombinase.

In some embodiments, a cell is provided that contains, integrated within a first enhanced expression locus, from 5' to 3': a first RRS, a first exogenous nucleic acid, and a second RRS; and integrated within a second enhanced expression locus, from 5' to 3': a third RRS, a second exogenous nucleic acid, and a fourth RRS; wherein the first and second RRS are different, and the third and fourth RRSs are different.

In some embodiments, the first exogenous nucleic acid includes a first selectable marker gene, and the second exogenous nucleic acid includes a second selectable marker gene, wherein the first and the second selectable marker genes are different.

In some embodiments, one or both of the first and second exogenous nucleic acids can include an additional RRS, i.e., an additional RRS between the first and second RRSs in the first locus, and/or an additional RRS between the third and fourth RRS. The additional, middle RRS is different from the RRSs at the 5' and 3'. Where an additional RRS is included between a 5' RRS and a 3' RRS (e.g., between the first and second RRS), one selectable marker gene can be included between the 5' RRS and the additional (middle) RRS, and another, different selectable marker gene can be included between the additional RRS and the 3' RRS.

In another embodiment, the cell provides a first exogenous nucleic acid that includes a third RRS, i.e., an additional RRS between the first and second RRSs in the first locus, wherein the first and second RRSs flank two selection markers at the 5' and 3' ends of the expression cassette. In other embodiments, the second exogenous nucleic acid can also include an identical third RRS, i.e., an additional RRS between the first and second RRSs in the second locus, wherein the first and second RRSs flank two selection markers at the 5' and 3' ends of the expression cassette. The four selectable marker genes included between the first, third and second RRSs, are different from one another.

In another embodiment, the cell provides a first exogenous nucleic acid that includes a third RRS, i.e., an additional RRS between the first and second RRSs in the first locus, wherein the first and second RRSs flank two selection markers at the 5' and 3' ends of the expression cassette. In other embodiments, the second exogenous nucleic acid can include an sixth RRS, i.e., an additional RRS between a fourth and fifth RRSs in the second locus, wherein the fourth and fifth RRSs flank two selection markers at the 5' and 3' ends of the expression cassette. The four selectable marker genes included between RRSs, are different from one another.

In many of the embodiments, the cells provided herein are cells of a CHO cell line.

In various embodiments, the two enhanced expression loci utilized are selected from the group consisting of a locus containing nucleotide sequence at least 90% identical to SEQ ID NO: 1, a locus containing a nucleotide sequence at least 90% identical to SEQ ID NO: 2, and a locus containing a nucleotide sequence at least 90% identical to SEQ ID NO:3.

In a further aspect, vector sets are provided for integration and expression of bispecific antigen-binding proteins in a cell.

In some embodiments, the vector set includes a first vector containing from 5' to 3', a first RRS, a first nucleic acid containing a nucleotide sequence encoding a first HCF, and a second RRS; a second vector containing from 5' to 3', a third RRS, a second nucleic acid containing a nucleotide sequence encoding a second HCF, a fourth RRS; and a nucleotide sequence encoding a first LCF that is either within the first nucleic acid in the first vector, or is in a third vector different from the first and second vectors; wherein the first, second, third, and fourth RRSs are different; and wherein the bispecific antigen-binding protein contains the first HCF, the second HCF and the first LCF, and wherein the first and second HCFs are different.

In some embodiments, the nucleotide sequence encoding the first LCF is within the first nucleic acid in the first vector. In some embodiments, the first nucleic acid further includes a first selectable marker gene.

In some embodiments, the nucleotide sequence encoding the first LCF is provided in the third vector and is flanked by a 5' RRS and 3' RRS, wherein (i) the 3' RRS is the same as the first RRS, and the 5' RRS is different from the first and second RRSs, or alternatively (ii) the 5' RRS is the same as the second RRS, and the 3' RRS is different from the first and second RRSs. In some embodiments, the vectors can be designed such that the common RRS shared by the first and third vectors is provided in a split selectable marker gene format (or a split-intron format), e.g., placed at the 3' end of a 5' portion of a selectable marker gene on one of the first and third vectors, and is placed at the 5' end of the remaining 3' portion of the selectable marker gene on the other vector.

In some embodiments, the vector set further includes a nucleotide sequence encoding a second LCF that is provided either within the second nucleic acid in the second vector, or is in a fourth vector separate from the first, second and third vectors.

In some embodiments, the first and second LCFs are the same.

In some embodiments, the nucleotide sequence encoding the first LCF is included within the first nucleic acid in the first vector, and the nucleotide sequence encoding the second VL is provided on the fourth vector. In some embodiments, the nucleotide sequence encoding the second LCF on the fourth vector is flanked by a 5' RRS and 3' RRS, wherein (i) the 3' RRS is the same as the third RRS, and the 5' RRS is different from the third and fourth RRSs, or (ii) the 5' RRS is the same as the fourth RRS, and the 3' RRS is different from the third and fourth RRSs. In certain embodiments, the vectors are designed such that common RRS shared by the second and fourth vectors is provided in a split marker (e.g., via an intron) format, e.g., placed at the 3' end of a 5' portion of a selectable marker gene on one of the second and fourth vectors, and is placed at the 5' end of the remaining 3' portion of the selectable marker gene on the other vector.

In some embodiments, the nucleotide sequence encoding the first LCF is within the first nucleic acid in the first vector, and the nucleotide sequence encoding the second VL is within the second nucleic acid on the second vector.

In some embodiments, the nucleotide sequence encoding the first LCF is on the third vector, and the nucleotide sequence encoding the second VL is on the fourth vector. In some embodiments, the nucleotide sequence encoding the first LCF on the third vector is flanked by a 5' RRS and 3' RRS, wherein (i) the 3' RRS on the third vector is the same as the first RRS, and the 5' RRS on the third vector is different from the first and second RRSs, or (ii) the 5' RRS on the third vector is the same as the second RRS, and the 3' RRS on the third vector is different from the first and second RRSs; and wherein the nucleotide sequence encoding the second LCF on the fourth vector is flanked by a 5' RRS and 3' RRS, wherein (i) the 3' RRS on the fourth vector is the same as the third RRS, and the 5' RRS on the fourth vector is different from the third and fourth RRSs, or (ii) the 5' RRS on the fourth vector is the same as the fourth RRS, and the 3' RRS on the fourth vector is different from the third and fourth RRSs.

In many embodiments of a vector set provided herein, the nucleotide sequence encoding the first HCF can encode a first CH3 domain, and the nucleotide sequence encoding the second HCF can encode a second CH3 domain. In some embodiments, the first and second CH3 domains differ in at least one amino acid. In some embodiments, the nucleotide sequences encoding the first and second CH3 domains differ in that one of the nucleotide sequences has been codon modified.

In many embodiments of a vector set provided herein, each of the nucleotide sequences encoding a HCF or LCF is independently linked a promoter.

In some embodiments, a vector set can further include a nucleotide sequence encoding one or more recombinases that recognize one or more of the RRSs, which can be included in one of the LCF- or HCF-encoding vectors, or provided in a separate vector.

In still other embodiments, a vector set is provided that includes a first vector containing a first nucleic acid, flanked by a 5' homology arm and a 3' homology arm for integration into a first expression enhancing locus of a cell; and a second vector containing a second nucleic acid, flanked by a 5' homology arm and a 3' homology arm for integration into a second expression enhancing locus of the cell; wherein the first and second nucleic acids together encode an antigen-binding protein.

In a further aspect, this disclosure provides systems that include a combination of a cell (e.g., a CHO cell) with one or more vectors, and that can be utilized to make cells having integrated within two expression enhancing loci exogenous nucleic acids that together encode an antigen binding protein, either a monospecific protein or a bispecific protein. The systems can be provided in the form of a kit, for example.

In certain embodiments, a system is provided that includes a cell and a set of vectors, wherein the cell contains, integrated within two separate enhanced expression loci of its genome a set of RRSs that are different from one another and spaced between one or more exogenous nucleic acids, such as selection markers, for recombinant exchange with genes of interest in a set of vectors; and wherein the RRSs in the set of vectors comprise the same arrangement as the RRSs in the cell.

In some embodiments, a system is provided that includes a cell and a set of vectors, wherein the cell contains, integrated within a first enhanced expression locus: from 5' to 3', a first RRS, a first exogenous nucleic acid, and a second RRS, and integrated within a second enhanced expression locus: from 5' to 3', a third RRS, a second exogenous nucleic acid, and a fourth RRS; wherein the first and second RRSs are different, and the third and fourth RRSs are different; and wherein the first and second enhanced expression loci are different; wherein the vector set includes (i) a first vector containing from 5' to 3', a first vector 5' RRS, a first nucleic acid, and a first vector 3' RRS, wherein the first vector 5' and 3' RRSs are different; (ii) a second vector containing from 5' to 3', a second vector 5' RRS, a second nucleic acid, and a second vector 3' RRS, wherein the second vector 5' and 3' RRSs are different; and (iii) a nucleotide sequence encoding a first HCF and a nucleotide sequence encoding a first LCF, wherein one of the two heavy chain-encoding nucleotide sequences is in the first nucleic acid and the other nucleotide sequences is in the second nucleic acid; wherein the first HCF and the first LCF are regions of an antigen-binding protein; and wherein upon introduction of the vectors into the cell, the first and second nucleic acids in the vectors integrate into the first enhanced expression locus and the second enhanced expression locus, respectively, through recombination mediated by the RRSs.

In some embodiments, the antigen-binding protein is a monospecific antigen-binding protein.

In some embodiments, the first and third RRSs are the same, and the second and fourth RRSs are the same. In certain embodiments, a first additional RRS is present between the first and second RRS in the first locus. In some embodiments, the first vector 5' RRS is the same as the first and third. RRS; the first vector 3' RRS, the second vector 5' RRS, and the first additional RRS are the same; and the second vector 3' RRS is the same as the second and fourth RRS. In some embodiments, the LCF-encoding nucleotide sequence is in the first vector, and the HCF-encoding nucleotide sequence is in the second vector. In some embodiments, the first vector 3' RRS is placed at the 3' end of a 5' portion of a selectable marker gene, and the second vector 5' RRS is placed at the 5' end of the remaining 3' portion of the selectable marker gene. In other embodiments, the first vector 5' RRS is the same as the first RRS, and the first vector 3' RRS is the same as the second RRS; and wherein the second vector 5' RRS is the same as the third RRS, and the second vector 3' RRS is the same as the fourth RRS.

In various embodiments, the antigen-binding protein is a bispecific antigen-binding protein.

In some embodiments, the vector set in the system further includes a nucleotide sequence encoding a second HCF that is different from the first HCF.

In some embodiments, the nucleotide sequence encoding the first LCF and the nucleotide sequence encoding the second HCF are both included in the first nucleic acid in the first vector, and the nucleotide sequence encoding the first HCF is in the second vector. In some embodiments, the first vector 5' RRS is the same as the first RRS, the first vector 3' RRS is the same as the second RRS, the second vector 5' RRS is the same as the third RRS, and the second vector 3' RRS is the same as the fourth RRS, In some embodiments, the nucleotide sequence encoding the second HCF is on a third, separate vector, flanked by a third vector 5' RRS and a third vector 3' RRS. In some embodiments, the nucleotide sequence encoding the first LC is in the first vector, the nucleotide sequence encoding the first HCF is in the second vector, the first vector 5' RRS is the same as the first RRS, the first vector 3' RRS is the same as the second vector 5' RRS and as a first additional RRS, and the second vector 3' RRS is the same as the second RRS, the third vector 5' RRS is the same as the third RRS, and the third vector 3' RRS is the same as the fourth RRS, wherein the first additional RRS is included in the first locus between the first and second RRSs. In some embodiments, the vectors are designed to provide the common RRS in a split marker format, e.g., the first vector 3' RRS is placed at the 3' end of a 5' portion of a selectable marker gene included in the first vector, and the second vector 5' RRS is placed at the 5' end of the remaining selectable marker gene included in the second vector.

In some embodiments, the vector set of the system further includes a nucleotide sequence encoding a second LCF, which can be the same or different from the first LCF.

In some embodiments, the nucleotide sequence encoding the second LCF is in the second nucleic acid of the second vector, wherein the first vector 5' RRS is the same as the first RRS, the first vector 3' RRS is the same as the second RRS, the second vector 5' RRS is the same as the third RRS, and the second vector 3' RRS is the same as the fourth RRS.

In some embodiments, the nucleotide sequence encoding the second LCF is in a third, separate vector, flanked by a third vector 5' RRS and a third vector 3' RRS. In some embodiments, the first vector 5' and 3' RRS are identical to the first and second RRS in the first locus, respectively; the third vector 5' RRS is the same as the third RRS, the third vector 3' RRS is the same as the second vector '5 RRS and as an additional RRS present between the third and fourth RRSs in the second locus, the second vector 3' RRS is the same as the fourth RRS. In some embodiments, the common RRS is designed in a split marker format, e.g., the third vector 3' RRS is placed at the 3' end of a 5' portion of a selectable marker gene included in the third vector, and the second vector '5 RRS is placed at the 5' end of the remaining 3' portion of the selectable marker gene included in the second vector.

In many embodiments of a system provided herein, the nucleotide sequence encoding a HCF or LCF can encode amino acids from a constant region. In some embodiments, the nucleotide sequence encoding the first HCF can encode a first CH3 domain, and the nucleotide sequence encoding the second HCF can encode a second CH3 domain. In some embodiments, the first and second CH3 domains differ in at least one amino acid. In some embodiments, the nucleotide sequences encoding the first and second CH3 domains differ in that one of the nucleotide sequences has been codon modified.

In many embodiments of a system provided herein, each of the nucleotide sequences encoding a HCF or LCF is independently linked to a promoter.

In some embodiments, the vector set of a system can further include a nucleotide sequence encoding one or more recombinases that recognize one or more of the RRSs, which can be included in one of the HCF- or LCF-encoding vectors, or provided in a separate vector.

In various embodiments, the cell in a system provided herein is a CFO cell.

In various embodiments, the two enhanced expression loci are selected from the group consisting of a locus comprising the nucleotide sequence of SEQ ID NO: 1, a locus comprising the nucleotide sequence of SEQ ID NO: 2, and a locus comprising the nucleotide sequence of SEQ ID NO: 3.

In another aspect, this disclosure also provides methods of making bispecific antigen-binding proteins. In one embodiment, the method utilizes a system disclosed herein and introduces the vectors of the system into the cell of the system by transfection. Transfected cells where the exogenous nucleic acids have been properly integrated into two enhanced expression loci of the cell through RMCE can be screened and identified. HCF-containing polypeptides and LCF-containing polypeptides can be expressed from the integrated nucleic acids, and the antigen-binding protein of interest can be obtained from the identified transfected cell, and purified using known methods.

In another embodiment, the method simply utilizes a cell described hereinabove, which contains exogenous nucleic acids integrated at two enhanced expression loci that together encode an antigen-binding protein, and expresses the antigen-binding protein from the cell.

DETAILED DESCRIPTION

Definitions

Figure 1:
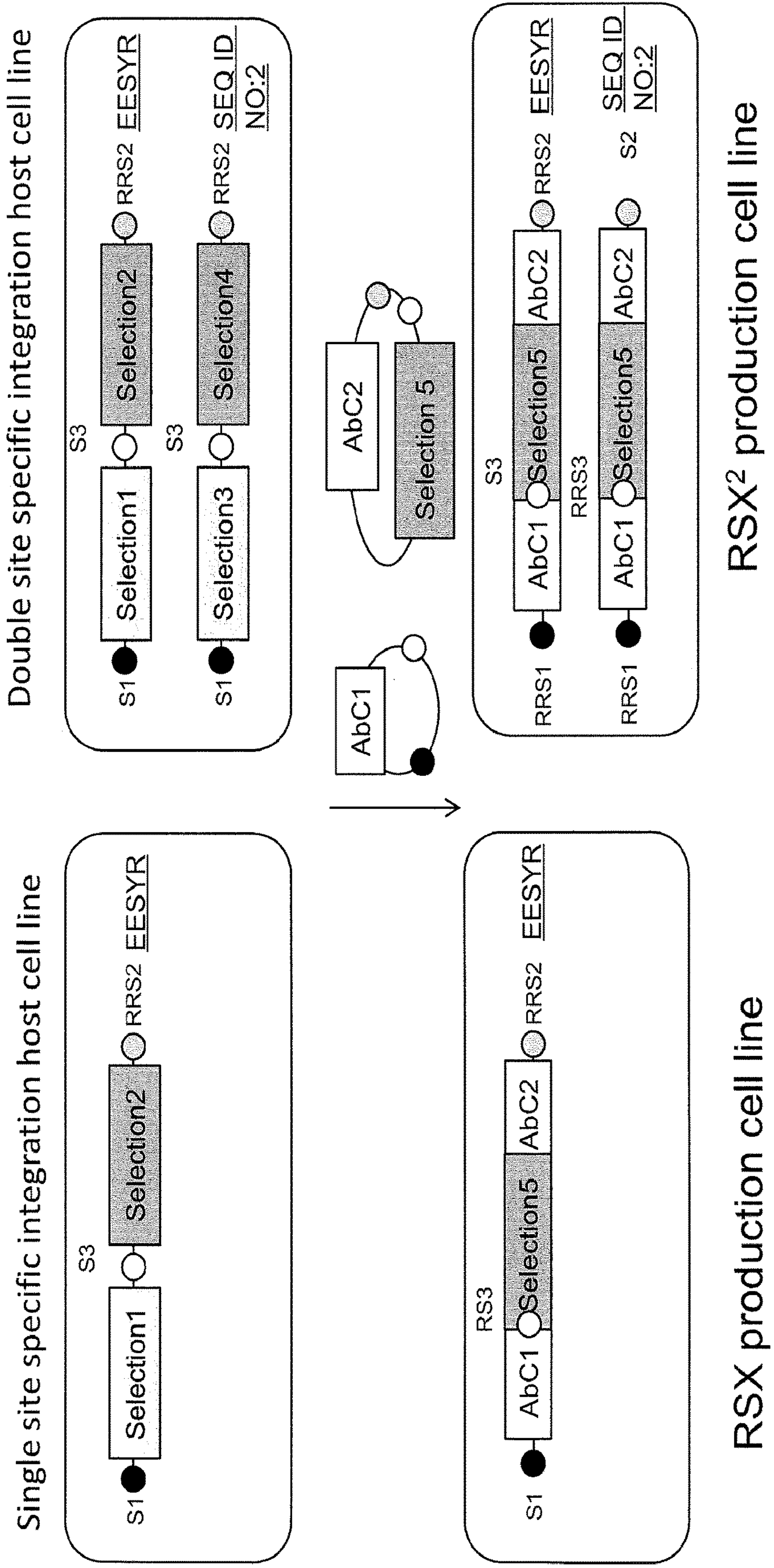
FIG. 1. An exemplary antibody cloning strategy for integration within one expression enhancing locus compared to multiple expression enhancing loci for a conventional monospecific antibody. Two vectors were transfected into the host cell, the first vector carrying a nucleic acid encoding antibody chain 1 (AbC1), such as a light chain, and a second vector carrying a nucleic acid encoding antibody chains 2 (AbC2), such as a heavy chain, and a selection marker different from the markers integrated within the targeted locus of the host cell. From 5' to 3': RRS1, middle RRS3 and RRS2 sites of the vector constructs match the RRS sites flanking selection markers within the loci of the host cell. An additional vector transfected into the host cells encodes for a recombinase. When the selection marker of the second vector is an antibiotic resistance gene, and since the two vectors are engineered to combine and allow expression of the marker, positive recombinant clones are selected for growth in the antibiotic. Alternatively, fluorescent marker enables positive clone selection by fluorescent activated cell sorting (FACS) analysis. The same vectors may be utilized for site-specific integration at a single locus, such as the EESYR® locus (Locus 1).

The term "antibody", as used herein, includes immunoglobulin molecules comprised of four polypeptide chains, two heavy (H) chains and two light (L) chains inter-connected by disulfide bonds. Each heavy chain may comprise a heavy chain variable region (abbreviated herein as HCVR or VH) and a heavy chain constant region. The heavy chain constant region comprises three domains, CH1, CH2 and CH3 and a hinge. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

The phrase "antigen-binding protein" includes a protein that has at least one CDR and is capable of selectively recognizing an antigen, i.e., is capable of binding an antigen with a $_{KD}$ that is at least in the micromolar range. Therapeutic antigen-binding proteins (e.g., therapeutic antibodies) frequently require a $_{KD}$ that is in the nanomolar or the picomolar range. Typically, an antigen-binding protein includes two or more CDRs, e.g., 2, 3, 4, 5, or 6 CDRs. Examples of antigen binding proteins include antibodies, antigen-binding fragments of antibodies such as polypeptides containing the variable regions of heavy chains and light chains of an antibody (e.g., Fab fragment, $F(ab')_2$ fragment), and proteins containing the variable regions of heavy chains and light chains of an antibody and containing additional amino acids from the constant regions of heavy and/or light chains (such as one or more constant domains, i.e., one or more of CL, CH1, hinge, CH2, and CH3 domains).

The phrase "bispecific antigen-binding protein" includes antigen-binding proteins capable of selectively binding, or having different specificities to, two or more epitopes—either on two different molecules (e.g., antigens) or on the same molecule (e.g., on the same antigen). The antigen binding portion, or fragment antigen binding (Fab) portion of such protein renders specificity to a particular antigen, and is typically comprised of a heavy chain variable region and a light chain variable region of an immunoglobulin. In some circumstances, the heavy chain variable region and light chain variable region may not be a cognate pair, in other words, have a different binding specificities.

An example of a bispecific antigen-binding protein is a "bispecific antibody", which includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antigen-binding protein is capable of selectively binding two different epitopes (a first epitope and a second epitope), the affinity of the variable region of the first heavy chain for the first epitope will generally be at least one to two or three or four orders of magnitude lower than the affinity of the variable region of the first heavy chain for the second epitope, and vice versa. Bispecific antigen-binding proteins such as bispecific antibodies can include the variable regions of heavy chains that recognize different epitopes of the same antigen. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. In one embodiment, an Fc domain includes at least CH2 and CH3. An Fc domain may include a hinge, a CH2 domain and CH3 domain.

One embodied bispecific format includes, a first heavy chain (RC), a second heavy chain Which has a modified CH3 (HC*), and a common light chain (LC) (two copies of the same light chain). Another embodiment includes a first heavy chain (HC), a common LC and a HC-ScFv fusion polypeptide (wherein the second HC is fused to the N-terminus of the ScFv). Another embodiment includes a first HC, a cognate LC, an HC-ScFv fusion polypeptide (wherein the second HC is fused to the N-terminus of the ScFv). Another embodiment includes a first heavy chain (HC), a LC and an Fc domain. Another embodiment includes a first HC, an LC, an ScFv-Fc fusion polypeptide (wherein the Fc is fused to the C-terminus of the ScFv). Another embodiment includes a first HC, a common LC, and an Fe-ScFv fusion polypeptide (wherein the Fc is fused to the N-terminus of the ScFv). Another embodiment includes a first HC, a LC and an ScFv-HC (wherein the second HC is fused to the C-terminus of the ScFv).

In certain embodiments, one heavy chain (HC) may be native or "wild-type" sequence and the second heavy chain may be modified in the Fc domain. In other embodiments, one heavy chain (HC) may be native or "wild-type" sequence and the second heavy chain may be codon-modified.

The term "cell" includes any cell that is suitable for expressing a recombinant nucleic acid sequence, and has a locus that allows for stable integration and enhanced expression of an exogenous nucleic acid. Cells include mammalian cells, such as non-human animal cells, human cells, or cell fusions such as, for example, hybridomas or quadromas. In some embodiments, the cell is a human, monkey, ape, hamster, rat, or mouse cell. In some embodiments, the cell is a mammalian cell selected from the following cells: CHO (e.g., CHO Kl, DXB-11 CHO, Veggie-CHO), COS (e.g., COS-7), retinal cell, Vero, CV1, kidney (e.g., 11E1(293, 293 EBNA, MSR 293, MDCK, HaK, BHK), HeLa, HepG2, W138, MRC 5, Colo205, 11B 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

"Cell density" refers to the number of cells per volume of sample, for example as number of total (viable and dead) cells per mL. The number of cells may be counted manually or by automation, such as with a flow cytometer. Automated cell counters have been adapted to count the number of viable or dead or both viable; dead cells using for example a standard tryptan blue uptake technique. The phrase "viable cell density" or "viable cell concentration" refers to the number of viable cells per volume of sample (also referred to as "viable cell count"). Any number of well-known manual or automated techniques may be used to determine cell density. Online biomass measurements of the culture may be measured, where the capacitance or optical density is correlated to the number of cells per volume. Final cell density in a cell culture, such as in a production culture, varies depending on the starting cell line, for example in the range of about 1.0 to $10\times10^6$ cells/mL. In some embodiments, final cell density reaches 1.0 to $10\times10^6$ cells/mL prior to harvest of protein of interest from a production cell culture. In other embodiments, final cell density reaches greater than $5.0\times10^6$ cells/ mL, greater than $6\times10^6$ cells/mL greater than $7\times10^6$ cells/mL, greater than $8\times10^6$ cells/mL, greater than $9\times10^6$ cells/mL, or greater than $10\times10^6$ cells/ mL.

The term "codon modified" means that a protein-coding nucleotide sequence has been modified in one or more nucleotides, i.e., one or more codons, without changing the amino acids encoded by the codons, resulting in a codon-modified version of the nucleotide sequence. Codon modification of a nucleotide sequence can provide a convenient basis to differentiate a nucleotide sequence from its codon-modified version in a nucleic acid-based assay (e.g., a hybridization based assays, PCR, among others). In some instances, codons of a nucleotide sequence are modified to provide improved or optimized expression of the encoded protein in a host cell by employing codon optimization techniques well known in the art (Gustafsson, C., et al., 2004, *Trends in Biotechnology,* 22:346-353; Chung, B. K.-S., et al., 2013, Journal of Biotechnology, 167:326-333; Gustafsson, C., et at, 2012, *Protein Expr Purif.* 83(1): 37-46). Sequence design software tools using such techniques are also well-known in the art, including but not limited to Codon optimizer (Fuglsang A. 2003, *Protein Expr Purif,* 31:247-249), Gene Designer (Villalobos A, et al., 2006, *BMC Bioinforma,* 7:285), and OPTIMIZER (Puigbò P, et al. 2007, *Nucleic Acids Research,* 35:W126-W131), among others.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "expression enhancing locus" refers to a locus in the genome of a cell that contains a sequence or sequences and exhibits a higher level expression as compared to other regions or sequences in the genome when a suitable gene or construct is exogenously added (i.e., integrated) in or near the sequence or sequences, or "operably linked" to the sequence or sequences.

The term "enhanced" when used to describe enhanced expression includes an enhancement of at least about 1.5-fold to at least about 3-fold enhancement in expression over what is typically observed by random integration of an exogenous sequence into a genome or by integration at a different locus, for example, as compared to a pool of random integrant of a single copy of the same expression construct. Fold-expression enhancement observed employing the sequences of the invention is in comparison to an expression level of the same gene, measured under substantially the same conditions, in the absence of a sequence of the invention, for example in comparison to integration at another locus into the same species genome. Enhanced recombination efficiency includes an enhancement of the ability of a locus to recombine (for example, employing recombinase-recognition sites ("RRS")). Enhancement refers to an efficiency of recombination over random recombination for example, without employing recombinase-recognition sites or the like, which is typically 0.1%. A preferred enhanced recombination efficiency is about 10-fold over random, or about 1%. Unless specified, the claimed invention is not limited to a specific recombination efficiency. Enhanced expression loci typically support high productivity of the protein of interest by the host cell. Hence, enhanced expression includes high production of the protein of interest (elevated titer in grams of protein) per cell, rather than attaining high titers simply by high copy number of cells in culture. Specific productivity Qp (pg/cell/day, i.e. pcd) is considered a measure of sustainable productivity. Recombinant host cells exhibiting Qp greater than 5 pcd, or greater than 10 pcd, or greater than 15 pcd, or greater than 20 pcd, or greater than 25 pcd, or even greater than 30 pcd are desirable. Host cells with a gene of interest inserted into an expression-enhancing locus, or "hotspot", exhibit high specific productivity.

Where the phrase "exogenously added gene", "exogenously added nucleic acid", or simply "exogenous nucleic acid", is employed with reference to a locus of interest, the phrase refers to any DNA sequence or gene not present within the locus of interest as the locus is found in nature. For example, an "exogenous nucleic acid" within a CHO locus (e.g., a locus comprising a sequence of SEQ ID NO: 1 or SEQ ID NO: 2), can be a hamster gene not found within the particular CHO locus in nature (i.e., a hamster gene from another locus in the hamster genome), a gene from any other species (e.g., a human gene), a chimeric gene (e.g., human/mouse), or any other gene not found in nature to exist within the CHO locus of interest.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. A typical heavy chain has, following the variable domain (from N-terminal to C-terminal), a CHI domain, a hinge, a CH2 domain, and a CH3 domain. The term "a fragment of a heavy chain" includes a peptide of at least 10, 20, 30, 40, 50, 60, 70, 80, 90, 100 or more amino acids of a heavy chain, and may include one or more CDRs, one or more CDRs combined with one or more FRs, one or more of CH1, hinge, CH2, or CH3, the variable region, the constant region, fragments of the constant region (e.g. CH1, CH2 CH3), or combinations thereof. Examples of an HCF include VHs, and full or parts of Fc regions. The phrase "a nucleotide sequence encoding an HCF" includes nucleotide sequences encoding a polypeptide consisting of an HCF and nucleotide sequences encoding a polypeptide containing an HCF, e.g., polypeptides that may contain additional amino acids in addition to a specified HCF. For example, a nucleotide sequence encoding an HCF includes nucleotide sequences encoding polypeptides consisting of a VH, consisting of a VH linked to a CH3, consisting of a full heavy chain, among others.

A "homologous sequence" in the context of nucleic acid sequences refers to a sequence that is substantially homologous to a reference nucleic acid sequence. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CURL-FR2-CDR2-FR3-CDR3-FR4, and a light chain constant domain. Light chains that can be used with this invention include those, e.g., that do not selectively bind either the first or second epitope selectively bound by a bispecific antibody. Suitable light chains also include those that can bind or contribute to the binding of, one or both epitopes that are bound by the antigen-binding regions of an antibody. The term "a fragment of a light chain" or "a light chain fragment" (or "LCF") includes a peptide of at least 10, 20, 30, 40, 50, 60, 70, 80, 90, 100 or more amino acids of a light chain, and may include one or more CDRs, one or more CDRs combined with one or more FRs, the variable region, the constant region, fragments of the constant region, or combinations thereof. Examples of an LCF include VLs and full or parts of light chain constant regions ("CLs"). The phrase "a nucleotide sequence encoding an LCF" includes nucleotide sequences encoding a polypeptide consisting of an LCF and nucleotide sequences encoding a polypeptide containing an LCF, e.g., polypeptides that may contain additional amino acids in addition to a specified LCF. For example, a nucleotide sequence encoding an LCF includes nucleotide sequences encoding polypeptides consisting of a VL, or consisting of a full light chain, among others.

The phrase "operably linked" refers to linkage of nucleic acids or proteins in a manner that the linked molecules function as intended. DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An expression-enhancing sequence of the locus of interest is operably linked to a gene of interest (GOI) where it is functionally related to the GOI, for example, where its presence results in enhanced expression of the GOI.

"Percent identity", when describing a locus of interest, such as SEQ ID NO: 1 or SEQ ID NO: 2, or a fragment thereof, is meant to include homologous sequences that display the recited identity along regions of contiguous homology, but the presence of gaps, deletions, or insertions that have no homolog in the compared sequence are not taken into account in calculating percent identity.

As used herein, a "percent identity" determination between, e.g., SEQ ID NO: 1, or fragment thereof, with a species homolog, would not include a comparison of sequences where the species homolog has no homologous sequence to compare in an alignment (i.e., SEQ ID NO: 1 or the fragment thereof has an insertion at that point, or the species homolog has a gap or deletion, as the case may be). Thus, "percent identity" does not include penalties for gaps, deletions, and insertions.

"Recognition site" or "recognition sequence" is a specific DNA sequence recognized by a nuclease or other enzyme to bind and direct site-specific cleavage of the DNA backbone. Endonucleases cleave DNA within a DNA molecule. Recognition sites are also referred to in the art as recognition target sites.

"Recombinase recognition site" (or "RRS") is the specific DNA sequence recognized by a recombinase, such as Cre recombinase (Cre) or flippase (flp). Site-specific recombinases can perform DNA rearrangements, including deletions, inversions and translocations when one or more of their target recognition sequences are placed strategically into the genome of an organism. In one example, Cre specifically mediates recombination events at its DNA target recognition site loxP, which is composed of two 13-bp inverted repeats separated by an 8-bp spacer. More than one recombinase recognition site may be employed, for example, to facilitate a recombination-mediated exchange of DNA. Variants or mutants of recombinase recognition sites, for example lox sites, may also be employed (Araki, N. et al, 2002, *Nucleic Acids Research,* 30:19, el03).

"Recombinase-mediated cassette exchange" or "RMCE" relates to a process for precisely replacing a. genomic target cassette with a donor cassette. The molecular compositions typically provided in order to perform this process include 1) a genomic target cassette flanked both 5' and 3' by recognition target sites specific to a particular recombinase, 2) a donor cassette flanked by matching recognition target sites, and 3) the site-specific recombinase. Recombinase proteins are well known in the art (Turan, S. and Bode J., 2011, *FASEB J.,* 25, pp. 4088-4107) and enable precise cleavage of DNA within a specific recognition target site (sequence of DNA) without gain or loss of nucleotides. Common recombinase/site combinations include, but are not limited to, Cre/lox and Flp/frt. Commercially available kits also provide vectors containing the R4-attP site and a vector encoding the phiC31 integrase for RMCE. (See also, e.g. U.S. Published Application No. US20130004946.)

"Site-specific integration" or "targeted insertion" refers to gene targeting methods employed to direct insertion or integration of a gene or nucleic acid sequence to a specific location in the genome, i.e., to direct the DNA to a specific site between two nucleotides in a contiguous polynucleotide chain. Site-specific integration or targeted insertion may also be done for a particular nucleic acid that includes multiple expression units or cassettes, such as multiple genes, each having their own regulatory elements (such as promoters, enhancers, and/or transcriptional termination sequences). "Insertion" and "integration" are used interchangeably. It is understood that insertion of a gene or nucleic acid sequence (for example a nucleic acid sequence comprising an expression cassette) may result in (or may be engineered for) the replacement or deletion of one or more nucleic acids depending on the gene editing technique being utilized.

"Stable integration" means that an exogenous nucleic acid integrated in the genome of a host cell remains integrated for an extended period of time in cell culture, for example, at least 7 days, at least 10 days, at least 15 days, at least 20 days, at least 25 days, at least 30 days, at least 35 days, at least 40 days, at least 45 days, at least 50 days, at least 55 days, at least 60 days, or longer. It is understood that making bispecific antigen-binding proteins for manufacturing and purification at large-scale is a challenging task. Stability and clonality are essential to the reproducibility of any biomolecule, especially one to be used therapeutically. The stable clones expressing bispecific antibodies made by the methods of this disclosure provide a consistent and reproducible way to generate therapeutic biomolecules.

General Description

This disclosure provides for compositions and methods for improved expression of multiple polypeptides in a host cell particularly Chinese hamster (*Cricetulus griseus*) cell lines, by employing multiple (e.g., two) expression-enhancing loci in the host cell. More specifically, the disclosure provides compositions and methods designed to integrate multiple exogenous nucleic acids that together encode an antigen-binding protein into multiple expression-enhancing loci in a host cell such as a CHO cell in a site-specific manner. In particular, this disclosure provides cells containing multiple exogenous nucleic acids integrated within multiple expression-enhancing loci wherein the multiple exogenous nucleic acids together encode an antigen-binding protein. This disclosure further provides nucleic acid vectors designed for site-specific integration of multiple exogenous nucleic acids into multiple expression-enhancing loci. This disclosure additionally provides systems that include a host cell containing multiple recombinase recognition sites (RRSs) at each of multiple expression-enhancing loci, and a set of vectors containing matching RRSs and multiple exogenous nucleic acids, for site-specific integration of the multiple exogenous nucleic acids from the vectors into the multiple expression-enhancing loci. Further, this disclosure provides methods for making an antigen-binding protein using the cells, vectors and systems disclosed herein.

Cells Having Multiple Exogenous Nucleic Acids Integrated Site-Specifically Within Multiple Expression Enhancing Loci In one aspect, this disclosure provides a cell that contains multiple exogenous nucleic acids integrated site-specifically in two expression-enhancing loci wherein the multiple exogenous nucleic acids together encode an antigen-binding protein. The antigen-binding protein can be a bispecific antigen-binding protein, or a conventional (i.e., monospecific) antigen-binding protein.

The cells provided herein are capable of producing a desired antigen-binding protein with high titers and/or high specific productivity (pg/cell/day). In some embodiments, a cell produces an antigen-binding protein at a titer of at least 1 g/L, 1.5 g/L, 2.0 g/L. 2.5 g/L, 3.0 g/L, 3.5 g/L, 4.0 g/L, 4.5 g/L, 5.0 g/L, 10 g/L, or greater. In some embodiments, a cell that produces an antigen-binding protein has a specific productivity of at least 5, 6, 7, 8, 9, 10, 11, 12, 13, 14, 15 picogram/cell/day, or higher, determined based on total antigen-binding proteins (in pg) produced per cell per day.

The host cells comprising exogenous nucleic acids which together encode an antigen-binding protein and are integrated within two enhanced expression loci exhibit high cell density in a production culture, e.g. 1 to $10\times10^6$ cells/mL, In other embodiments, the antigen-binding protein-encoding host cell reaches a final cell density of at least $5\times10^6$ cells/mL, $6\times10^6$ cells/mL, $7\times10^6$ cells/mL, $8\times10^6$ cells/mL, $9\times10^6$ cells/mL, or $10\times10^6$ cells/mL (in production culture).

In some embodiments, a cell is provided that is capable of producing a bispecific antigen-binding protein at a ratio of the bispecific antigen-binding protein titer versus the total antigen-binding protein titer of at least 5%, 10%, 15%, 20%, 25%, 30%, 35%, 40%, 50%, 60%, or higher. In some embodiments, a cell is provided that is capable of producing a bispecific antigen-binding protein, wherein the ratio of the bispecific antigen-binding protein titer is at least 50% of the total antigen-binding protein titer produced by the cell.

In other embodiments, a cell is provided that is capable of producing an antigen-binding protein wherein the total antigen-binding protein titer produced by expression in two loci compared with the total antigen-binding protein titer produced by expression in one loci is at least 5%, 10%, 15%, 20%, 25%, 30%, 35%, 40%, 50%, 60%, or higher. In certain embodiments, a cell is provided that is capable of producing an antigen-binding protein wherein the total antigen-binding protein titer produced by expression in two loci compared with the total antigen-binding protein titer produced by expression in one loci is at least 0.5 fold, 0.75 fold, 1 fold, 1.5 fold, 1.75 fold, 2 fold, or higher.

In some embodiments, the cell contains a first exogenous nucleic acid integrated at a specific site within a first enhanced expression locus; and a second exogenous nucleic acid integrated at a specific site within a second enhanced expression locus; wherein the first and second exogenous nucleic acids together encode an antigen-binding protein. The first and second exogenous nucleic acids together include multiple nucleotide sequences encoding HCF(s) or LCF(s) (e.g., variable regions) of the antigen-binding protein. For instance, for monospecific antibodies, there can be one nucleotide sequence encoding a HCF (e.g., a VH) and one nucleotide sequence encoding a LCF (e.g., a VL) for a monospecific antigen-binding protein, or multiple copies (e.g., two copies) of each. For bispecific antibodies, there can be two nucleotide sequences each encoding a HCF (typically the two HCFs being different from each other), one or two copies of a nucleotide sequence encoding a LCF, or two nucleotide sequences encoding two different LCFs. Depending on whether the antigen-binding protein is monospecific or bispecific, nucleotide sequences encoding HCF(s) or LCF(s) (e.g., variable regions) can be integrated in different variations or combinations at two enhanced expression loci. For example, for monospecific antigen-binding proteins, in one instance, a nucleotide sequence encoding a HCF and a nucleotide sequence encoding a LCF can be integrated separately in two loci, one at each locus; whereas in another instance, a nucleic acid encoding a HCF and a LCF is integrated at one locus, and a separate nucleic acid encoding the same HCF and the same LCFs is integrated at another locus. For bispecific antigen-binding proteins, in one instance, a nucleotide sequence encoding a first HCF and a LCF can be integrated in a first locus, and a nucleotide sequence encoding a second HCF is integrated in a second locus, wherein the two HCFs are different, and the LCF is the common LCF of the bispecific antigen-binding protein; and in another instance, a nucleotide sequence encoding a first HCF and a LCF is integrated in a first locus, and a nucleotide sequence encoding a second HCF and the same LCF is integrated in a second locus.

In some embodiments, the nucleotide sequence encoding a HCF or a LCF can encode amino acids from a constant region. For example, the nucleotide sequence encoding a HCF or LCF can encode one or more of CL, CH1, CH2, CH3, or a combination of CH1, CH2 or CH3, or can encode an entire constant region. In some embodiments, a nucleotide sequence encoding a HCF encodes a CH3 domain. In specific embodiments, a nucleotide sequence encoding a HCF encodes a heavy chain. In sonic embodiments, a nucleotide sequence encoding a LCF encodes a light chain.

In embodiments where two HCFs are involved, the nucleotide sequence encoding a first HCF can encode amino acids from a first constant region, and the nucleotide sequence encoding a second HCF can encode amino acids from a second constant region, wherein the amino acids from the two constant regions can be the same or different in at least one position (such as positions resulting in a different Protein A binding characteristics, or other positions described hereinbelow for various bispecific antigen-binding proteins). Independent of the differences in amino acids, the two nucleotide sequences encoding amino acids from two constant regions can be differentiated by modifying one or more codons of one nucleotide sequence, which provides a convenient basis to differentiate the two nucleotide sequences in a nucleic acid-based assay.

In some embodiments, each HCF- or LCF-coding nucleotide sequence is independently and operably linked to a transcriptional regulatory sequence that contains a promoter. By “independently”, it means that each coding sequence is operably linked to a separate transcriptional regulatory sequence such as a promoter, so that transcription of the coding sequences is under separate regulation and control. In some embodiments, the promoters directing transcription of the two HCF-containing polypeptides are the same. In some embodiments, the promoters directing transcription of the two HCF-containing polypeptides, as well as the promoter directing transcription of the VL-containing polypeptide, are all the same, e.g., a CMV promoter. In some embodiments, each HCF- or LCF-coding nucleotide sequence is independently and operably linked to an inducible or repressible promoter. Inducible and repressible promoters allow production to occur only in production phase (fed-batch culture) and not during growth phase (seed train culture); or to differentially control expression of antibody components (HCF and LCF) in different loci with precision. Fine control of production (expression) of each gene product may be achieved by way of different promoters.

In one such example, cells are first engineered to express the tetracycline repressor protein (TetR) and each HCF- and LCF-coding nucleotide sequence is placed under transcriptional control of a promoter whose activity is regulated by TetR. Two tandem TetR operators (TetO) are placed immediately downstream of the CAW promoter. In some embodiments, each HCF- and/or LCF-coding nucleotide sequence is independently and operably linked to a promoter upstream of at least one TetR operator (TetO) or Arc operator (Arco). In other embodiments, each HCF- and/or UT-coding nucleotide sequence is independently and operably linked to a CMV/TetO or CMV/ArcO hybrid promoter. Additional suitable promoters are described herein below.

In some embodiments, the multiple exogenous nucleic acids integrated at two loci are flanked by RRSs. For example, a first RRS and a second RRS are positioned 5' and 3', respectively, relative to a first exogenous nucleic acid integrated at a first locus, and a third RRS and a fourth RRS are positioned 5' and 3', respectively, relative to a second exogenous nucleic acid integrated at a second locus, wherein the first and second RRSs are different, and the third and fourth RRSs are different. In some embodiments, the first, second, third and fourth RRS are all different from each other. In other embodiments, the first and third RRSs are the same, and the second and fourth RRS' are the same, where the first exogenous nucleic acid encodes a HCF and a LCF, and the second exogenous nucleic acid encodes the same HCF and LCF.

In some embodiments, where an exogenous nucleic acid integrated at a locus includes two HCF or LCF-coding nucleotide sequences, an additional RRS can be included between the two nucleotide sequences. Such additional RRS should be different from the two RRSs flanking the exogenous nucleic acid. In some embodiments, the additional RRS is inserted into an intron of a selectable marker gene that is included in the integrated exogenous nucleic acid and positioned between the two HCF or LCF-coding nucleotide sequences. After transcription and post transcriptional processing, the intron will be excised giving rise to mRNA encoding the selectable marker. In embodiments where both the exogenous nucleic acid integrated at a first locus and the exogenous nucleic acid integrated at a second locus include two HCF or LCF-coding sequences (e.g., LCF-HCF1 and LCF-HCF2), an additional RRS can be included in only one, or both, of the first and second exogenous nucleic acids between the two HCF or LCF-coding sequences at each locus. The additional RRS in the first locus can be the same or different from the additional RRS in the second locus. Each additional RRS should be different from the two RRSs flanking the exogenous nucleic acid integrated at that locus. Each additional RRS can be optionally inserted within an intron of a selectable marker gene, and the selectable marker genes having an intron in the two loci can be different.

Where multiple HCF or LCF-coding sequences are included within an exogenous nucleic acid integrated at a locus, the relative positions of the multiple coding sequences within the locus can vary. For example, in embodiments where an integrated exogenous nucleic acid includes a LCF-encoding nucleotide sequence and a HCF-encoding nucleotide sequence, the LCF-encoding nucleotide sequence can be located upstream or downstream relative to the HCF-encoding nucleotide sequence. In specific embodiments, the LCF-encoding nucleotide sequence is located upstream relative to the HCF-encoding nucleotide sequence. Where both loci include a LCF-encoding nucleotide sequence and a HCF-encoding nucleotide sequence, in specific embodiments, the LCF-encoding nucleotide sequence is located upstream relative to the HCF-encoding nucleotide sequence in both loci.

In further embodiments, cells are provide that contains a first pair of RRSs integrated within a first enhanced expression locus, and a second pair of RRSs integrated within a second enhanced expression locus, wherein the two RRSs within each pair are different. Such cells are useful for receiving multiple exogenous nucleic acids to be integrated that together encode an antigen-binding protein.

In some embodiments, a first exogenous nucleic acid is present between the two RRSs at the first locus, and a second exogenous nucleic acid is present between the two RRSs at the second locus. The first and second exogenous nucleic acids can each encode one or more selectable marker genes. The selectable marker genes can differ from each other.

In some embodiments, an additional RRS is present between the two RRSs in the pair (i.e., the 5' RRS and the 3' RRS) at a locus, wherein the additional RRS is different from both the 5' RRS and the 3' RRS at the locus. In some embodiments, an additional RRS is present between the 5' RRS and the 3' RRS at one of the two loci; and in other embodiments, an additional RRS is present between the 5' RRS and the 3' RRS at each of the two loci. Where an additional RRS is present between the 5' RRS and the 3' RRS, a selectable marker gene can be included between the 5' RRS and the additional RRS, and another selectable marker gene can be included between the additional RRS and the 3' RRS, and the two selectable markers are different.

In many of the embodiments described, the cell is a CHO cell, wherein one of two enhanced expression loci is selected from the group consisting of a nucleotide sequence at least 90% identical to SEQ ID NO: 1, a nucleotide sequence at least 90% identical to SEQ ID NO: 2, and a nucleotide sequence at least 90% identical to SEQ ID NO: 3.

Bispecific Antigen-Binding Proteins

Bispecific antigen-binding proteins, such as bispecific antibodies, suitable for cloning and production in the cells, vectors, and systems described in this disclosure are not limited to any particular format of bispecific antigen-binding proteins.

In various embodiments, the bispecific antigen-binding protein includes two polypeptides, each containing an antigen-binding moeity (e.g., a HC) and a CH3 domain, wherein the antigen-binding moeity of the two polypeptides have different antigen specificities, and wherein the two CH3 domains are heterodimeric in respect to each other in that one of the CH3 domains has been modified in at least one amino acid position to give rise to differential Protein A binding characteristics between the two polypeptides. See, e.g., the bispecific antibodies described in U.S. Pat. No. 8,586,713. In this way, a differential protein A isolation scheme can be employed to readily isolate the heterodimeric bispecific antigen-binding proteins from homodimers.

In some embodiments, the bispecific antigen-binding protein includes two heavy chains having different antigen specificities and differing in at least one amino acid position in the CH3 domain to give rise to differential Protein A binding characteristics between the two heavy chains.

In some embodiments, the two polypeptides contain CH3 domains of human IgG, wherein one of the two polypeptides contains the CH3 domain of a human IgG selected from IgG1, IgG2 and IgG4, and the other one of the two polypeptides contains a modified CH3 domain of a human IgG selected from IgG 1, IgG2 and IgG4 wherein the modification reduces or eliminates the binding of the modified CH3 region to Protein A. In specific embodiments, one of the two polypeptides contains the CH3 domain of human IgG1, and the other one of the two polypeptides contains a modified CH3 domain of human IgG1 wherein the modification is selected from the group consisting of (i) 95R and (ii) 95R and 96F in the IMGT exon numbering system. In other specific embodiments, the modified CH3 domain comprises one to five additional modifications selected from the group consisting of 16E, 18M, 44S, 52N, 57M, and 821 in the IMGT exon numbering system.

In other various embodiments, the two polypeptides contain CH3 domains of mouse IgG, wherein one of the two polypeptides contains the CH3 domain of an unmodified mouse IgG, and the other one of the two polypeptides contains a modified CH3 domain of the mouse IgG wherein the modification reduces or eliminates the binding of the modified CH3 region to Protein A. In various embodiments, a mouse IgG CH3 region is modified to comprise particular amino acids at particular positions (EU numbering), selected from the group consisting of: 252T, 254T, and 256T; 252T, 254T, 256T, and 258K; 247P, 252T, 254T, 256T, and 258K; 435R and 436F; 252T, 254T, 256T, 435R, and 436F; 252T, 254T, 256T, 258K, 435R, and 436F; 24tP, 252T, 254T, 256T, 258K, 435R, and 436F; and, 435R. In a specific embodiment, a particular group of modifications is made, selected from the groups consisting of: M252T, S254T, S256T;

M252T, S254T, S256T, 1258K;1247P, M252T, S254T, S256T, I258K; H435R, H436F; M252T, S254T, S256T, H435R, H436F; M252T, S254T, S256T, I258K, H435R, H436F; I247P, M252T, S254T, S2567T, 1258K, H435R, H436F; and, H435R.

In various embodiments, a bispecific antigen-binding protein is a hybrid of a mouse and a rat monoclonal antibody or antigen-binding protein, e.g., a hybrid of mouse IgG2a and rat IgG2b. According to these embodiments, a bispecific antibody is composed of a heterodimer of the two antibodies comprising one heavy/light chain pair of each, associating via their Fc portions. The desired heterodimer can be easily purified from a mixture of two parental antibody homodimers and the bispecific heterodimer, because the binding properties of the bispecific antibody to Protein A are different from those of the parental antibodies: rat IgG2b does not bind to protein A, whereas the mouse IgG2a does. Consequently, the mouse-rat heterodimer binds to Protein A but elutes at a higher pH than the mouse IgG2a homodimer, and this makes selective purification of the bispecific heterodimer possible.

In other various embodiments, a bispecific antigen-binding protein is of a format that is referred to as "knobs-into-holes" in the art (see, e.g., U.S. Pat. No. 7,183,076). In these embodiments, the Fc portions of two antibodies are engineered to give one a protruding "knob", and the other a complementary "hole." When produced in the same cell, the heavy chains are said to preferentially form heterodimers rather than homodimers, by association of the engineered "knobs" with the engineered "holes."

In another embodiment, the first heavy chain and the second heavy chain comprises one or more amino acid modifications in the CH3 domain to enable interaction between two heavy chains. CH3-CH3 interface amino acid residues can be replaced with charged amino acid to provide electrostatically unfavorable homodimer formation. (See, e.g. PCT Publication No. WO2009089004; and European Publication No. EP1870459.)

In other embodiments, the first heavy chain comprises a CH3 domain of the isotype and the second heavy chain comprises a CH3 domain of IgG (or vice versa) to promote preferential formation of heterodimers. (See e.g. PCT Publication No. WO2007110205.)

In other embodiments, various formats can be incorporated with immunoglobulin chains by engineering methods to foster formation of heterodimers, such as Fab-arm exchange (PCT Publication No. PCT Publication No. WO2008119353; PCT Publication No. WO2011131746), coiled-coil domain interaction (PCT Publication No. W02011034605) or leucine zipper peptides (Kostelny, et al. *J Immunol.* 1992, 148(5):1547-1553).

Immunoglobulin heavy chain fragments (e.g., variable regions) that can be used to generate bispecific antigen binding proteins can be generated using any method known in the art. For example, a first heavy chain comprises a variable region that is encoded by a nucleic acid that is derived from the genome of a mature B cell of a first animal that has been immunized with a first antigen, and the first heavy chain specifically recognizes the first antigen; and a second heavy chain comprises a variable region that is encoded by a nucleic acid that is derived from the genome of a mature B cell of a second animal that has been immunized with a second antigen, and the second heavy chain specifically recognizes the second antigen. Immunoglobulin heavy chain variable region sequences can also be obtained by any other method known in the art, e.g., by phage display. In other examples, nucleic acids encoding the heavy chain variable regions include those of antibodies that have been described or otherwise available in the art. In some embodiments, one of the two heavy chain coding sequences have been codon modified in order to provide a convenient basis to differentiate the two coding sequences in nucleic acid based assays.

Bispecific antibodies comprising two heavy chains that recognize two different epitopes (or two different antigens) are more easily isolated where they can pair with the same light chain (i.e., light chains having identical variable and constant domains). A variety of methods are known in the art for generating light chains that can pair with two heavy chains of differing specificity, while not interfering or not substantially interfering with the selectivity and/or affinity of the heavy chain variable domain with its target antigen, as described in e.g., U.S. Pat. No. 8,586,713 and the art disclosed therein.

The bispecific antigen-binding proteins can have a variety of dual antigen specificities and associated useful applications.

In some examples, bispecific antigen-binding proteins that comprise binding specificity toward a tumor antigen and a T-cell antigen can be made that target an antigen on a. cell, e.g., CD20, and also target an antigen on a T-cell, e.g., a T cell receptor such as CD3. In this way, the bispecific antigen-binding protein targets both a cell of interest in a patient (e.g., B cell in a lymphoma patient, via CD20 binding) as well as a T-cell of the patient. The bispecific antigen-binding protein, in various embodiments, is designed so as to activate the T-cell upon binding CD3, thus coupling T-cell activation to a specific, selected tumor cell.

In the context of bispecific antigen-binding proteins wherein one moiety binds to a T cell receptor such as binding to CD3 and the other moiety binds a target antigen, the target antigen can be a tumor-associated antigen. Non-limiting examples of specific tumor-associated antigens include, e.g., AFP, ALK, BAGE proteins, BIRC5 (survivin), BIRC7, β-catenin, brc-abl, BRCA1, BCMA, BORIS, CA9, carbonic anhydrase DC, caspase-8, CALR, CCR5, CD19, CD20(MS4A1), CD22, CD30, CD40, CDK4, CEA, CLEC-12, CTLA4, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp1.00, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, MI, IAP, .Muc 1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAXS, PCTA-1, PLAC1, PRLR, PRAMS, PSMA (FOLH1), RAGE proteins, Ras, RGS5, Rho, SART-1, SART-3, Steap-1, Steap-2, TAG-72, TGF-β, TMPRSS2, Thompson-nouvelle antigen (Tn), TRP-1, TRP-2, tyrosinase, and uroplakin-3. In some embodiments, the bispecific antigen-binding protein comprises one moiety that binds CD3. Exemplified anti-CD3 antibody moieties are described in U.S. Pat. Appln. Pub. Nos. US2014/0088295M. and US20150266966A1, and in international Publication No. WO 2017/053856 published on Mar. 30, 2017, all of which are incorporated herein by reference). In other embodiments, the bispecific antigen-binding protein comprises one moiety that binds to CD3 and one moiety that binds to BCMA, CD19, CD20, CD28, CLEC-12, Her2, HLA protein, MAGE protein, Muc16, PSMA, or Steap-2. In still other embodiments, the bispecific antigen-binding protein is selected from the group consisting of an anti-CD3 x anti-CD20 bispecific antibody (as described in U.S. Pat. Appln. Pub. Nos. US2014/0088295A1 and US20150266966A1, herein incorporated by reference), an anti-CD3 x anti-Mucin 16 bispecific antibody (e.g., an anti-CD3 x anti-Muc16 bispecific antibody), and an anti-CD3 x anti- Prostate-specific membrane antigen bispecific antibody (e.g., an anti-CD3 x anti-PSMA bispecific antibody).

In the context of bispecific antigen-binding proteins wherein one moiety binds to a T cell receptor such as binds to CD3 and the other moiety binds a target antigen, the target antigen can be an infectious disease-associated antigen. Non-limiting examples of infectious disease-associated antigens include, e.g., an antigen that is expressed on the surface of a virus particle, or preferentially expressed on a cell that is infected with a virus, wherein the virus is selected from the group consisting of REV, hepatitis (A, B or C), herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillorna:virus, molluscum virus, poliovirus, rabies virus, JC virus, and arboviral encephalitis virus. Alternatively, the target antigen can be an antigen that is expressed on the surface of a bacterium, or preferentially expressed on a cell that is infected with a bacterium, wherein the bacterium is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacteria. In certain embodiments, the target antigen is an antigen that is expressed on the surface of a fungus, or preferentially expressed on a cell that is infected with a fungus, wherein the fungus is selected from the group consisting of *Candida* (*albicans, krusei, glabrata, tropicalis*, etc.), *Crytococcus neoformans, Aspergillus* (*fumigatus, niger*, etc.), *Mucorales* (*mucor, absidia, rhizopus*, etc.), *Sporothrix schenkii, Blastomyces dermatitidis, Paracoccidioides brasiliensis, Coccidioides immiti*s, and *Flistoplasma capsulatum*. In certain embodiments, the target antigen is an antigen that is expressed on the surface of a parasite, or preferentially expressed on a cell that is infected with a parasite, wherein the parasite is selected from the group consisting of *Entamoeba histolytica, Balantidium coli, Naegleriafowleri, Acanthamoeba* sp., *Giardia lambia, Cryptosporidium* sp., *Pneumocystis carinii, Plasmodium vivax, Babesia rnicroti, T rypanosoma brucei, Trypanosoma cruzi, Leishmania donovani, Toxoplasma gondii, Nippostrongylus brasiliensis, Taenia crassiceps*, and *Brugia malayi*. Non-limiting examples of specific pathogen-associated antigens include, e.g., HIV gp120, HIV CD4, hepatitis B glucoprotein L, hepatitis B glucoprotein M, hepatitis B glucoprotein S, hepatitis C E1, hepatitis C E2, hepatocyte-specific protein, herpes simplex virus gB, cytomegalovirus gB, and HTLV envelope protein.

Bispecific binding proteins that comprise two binding moieties that are each directed to a binding partner (i.e., each directed to a different target) on the surface of the same cell can also be made. This design is particularly suited to targeting specific cells or cell types that express both targets on the surface of the same cell. Although targets might appear individually on other cells, the binding moieties of these binding proteins are selected such that each binding moiety binds its target with a relatively low affinity (e.g., low micromolar, or high nanomolar—e.g., over a hundred nanomolar KD, e.g., 500, 600, 700, 800 nanomolar). In this way, prolonged target binding is favored only in situations where the two targets are in proximity on the same cell.

Bispecific binding proteins that comprise two binding moieties that bind the same target, each at a different epitope of the same target, can be made. This design is particularly suited for maximizing the probability of successfully blocking a target with binding protein. Multiple extracellular loops, e.g., of a transmembrane channel or a cell surface receptor, can be targeted by the same bispecific binding molecule.

Bispecific binding proteins that comprise two binding moieties that cluster and activate negative regulators of immune signaling to result in immune suppression can be made. Repression in cis can be achieved where the targets are on the same cell; repression in trans can be achieved where the targets are on different cells. Repression in cis, e.g., can be achieved with a bispecific binding protein having an anti-IgGRIIb binding moiety and an anti-FelD1 binding moiety, such that the IgGRIIb is clustered only in the presence of FelD1, in order to down-regulate an immune response to FelD1. Repression in trans, e.g., can be achieved with a bispecific binding protein having an anti-BTLA binding moiety and a binding moiety that specifically binds a tissue-specific antigen of interest, such that clustering of the inhibitory BMA molecule occurs only in the selected target tissue, which potentially addresses auto-immune diseases.

Bispecific binding proteins that activate multi-component receptors can be made. In this design, two binding moieties directed to two components of a receptor bind, cross-link the receptor, and activate signaling from the receptor. This can be done, e.g., using a. bispecific binding protein with a binding moiety that binds IFNAR1 and a binding moiety that binds IFNAR2, where binding cross-links the receptor. Such a bispecific binding protein can provide an alternative to interferon treatment.

Bispecific binding proteins that transport binding moieties across a semi-permeable barrier, e.g., the blood-brain barrier, can be made. In this design, one binding moiety binds a target that can transit a particular selective barrier; the other binding moiety targets a molecule with a therapeutic activity, wherein the target molecule with therapeutic activity cannot normally traverse the barrier. This kind of bispecific binding protein is useful for bringing therapeutics to tissues that the therapeutic would not otherwise reach. Some examples include targeting the pIGR receptor to transport a therapeutic into the gut or lung, or targeting the transferrin receptor to transport a therapeutic across the blood-brain barrier.

Bispecific binding proteins that transport binding moieties into specific cells or cell types can be made. In this design, one binding moiety targets a cell surface protein (e.g., a receptor) that is readily internalized into the cell. The other binding moiety targets an intracellular protein, where binding of the intracellular protein results in a therapeutic effect.

Bispecific binding proteins that bind a surface receptor of a phagocytic immune cell and a surface molecule of an infectious pathogen (e.g., a yeast or bacterium), to bring the infectious pathogen in the vicinity of a phagocytic immune cell to facilitate phagocytosis of the pathogen. An example of such a design would be a bispecific antibody that targets a CD64 or CD89 molecule and also a pathogen.

Bispecific binding proteins that have an antibody variable region as one binding moiety and a non-Ig moiety as a second binding moiety. The antibody variable region achieves targeting, whereas the non-Ig moiety is an effector or a toxin linked to an Fc. In this way, the ligand (e.g., an effector or toxin) is delivered to the target bound by the antibody variable region.

Bispecific binding proteins that have two moieties each bound to an Ig region (e.g., an Ig sequence containing a CH2 and CH3 region) such that any two protein moieties can be brought in each other's vicinity in the context of the Fe. Examples of this design include traps, e.g., homo- or heterodimeric trap molecules.

Expression-Enhancing Loci

Expression-enhancing loci suitable for use in this invention include for example, a locus that comprises a nucleotide sequence having substantial homology to SEQ ID NO: 1 as described in U.S. Pat. No. 8,389,239 (also referred to herein as the "EESYR® locus" or "Locus 1"), a locus that comprises a nucleotide sequence having substantial homology to SEQ ID NO: 2 or SEQ ID NO: 3 as described in U.S. application Ser. No. 14/919,300 (also referred to herein as "the YARS locus" or "Locus 2"), and other expression-enhancing loci and sequences documented in the art (e.g., US 20150167020A1, and U.S. Pat. No. 6,800,457).

In some embodiments, the two expression-enhancing loci used in this invention are selected from the group consisting of a locus that comprises a nucleotide sequence having substantial homology to SEQ ID NO: 1, a locus that comprises a nucleotide sequence having substantial homology to SEQ ID NO: 2, and a locus that comprises a nucleotide sequence having substantial homology to SEQ ID NO: 3. These loci contain sequences that not only provide for enhanced expression of genes integrated in operable linkage to the sequences within the sequences or within close proximity to the sequences), but also exhibit greater recombination efficiency and improved integration stability, as compared to other sequences in the genome.

SEQ ID NO: 1, SEQ ID NO: 2 and SEQ ID NO: 3 have been identified from CHO cells. Other mammalian species (such as, for example, humans or mice), were found to have limited homology to the identified expression-enhancing region; however, homologous sequences may be found in cell lines derived from other tissue types of *Cricetulus griseus*, or other homologous species, and can be isolated by techniques that are well-known in the art. For example, one may identify other homologous sequences by cross-species hybridization or PCR-based techniques. In addition, changes can be made in the nucleotide sequence set forth in SEQ ID NO: 1, SEQ ID NO: 2, or SEQ ID NO: 3, by site-directed or random mutagenesis techniques that are well known in the art. The resulting sequence variants can then be tested for expression-enhancing activity. DNAs that are at least about 90% identical in nucleic acid identity to SEQ ID NO: 1, SEQ ID NO: 2, or SEQ ID NO: 3, having expression-enhancing activity are isolatable by routine experimentation, and are expected to exhibit expression-enhancing activity.

The integration site, the site or nucleotide position of insertion of one or more exogenous nucleic acids, can be at any position that is within or adjacent to any of the expression enhancing sequences (such as SEQ ID NO: 1, SEQ ID NO: 2, SEQ ID NO: 3). Whether a specific chromosomal location within or adjacent to the locus of interest supports stable integration and efficient transcription of an integrated exogenous gene can be determined in accordance with standard procedures well known in the art, e.g., as described U.S. Pat. No. 8,389,239 and U.S. application Ser. No. 14,919,300.

The integration sites considered herein are located within the expression enhancing sequences, or within close proximity to the sequences, e.g., less than about 1 kb, 500 base pairs (bp), 250 bp, 100 bp, 50 bp, 25 bp, 10 bp, or less than about 5 bp upstream (5') or downstream (3') with respect to the location of an expression enhancing sequence on the chromosomal DNA. In still some other embodiments, the employed integration site is located at about 1000, 2500, 5000 or more base pairs upstream (5') or downstream (3') with respect to the location of an expression enhancing sequence on the chromosomal DNA.

It is understood in the art that large genomic regions, such as scaffold/matrix attachment regions, are employed for efficient replication and transcription of chromosomal DNA. A scaffold/matrix attachment region (S/MAR), also known as called scaffold-attachment region (SAR), or matrix-associated or matrix attachment region (MAR), is a eukaryotic genomic DNA region where the nuclear matrix attaches. Without being bound by any one theory, S/MARs typically map to non-coding regions, separate a given transcriptional region (e.g. chromatin domain) from its neighbors, and also provide platforms for the machinery and/or binding of factors that enable transcription, such as recognition sites for DNAses or polymerases. Some S/MARs have been characterized at about 14-20 kb in length (Klar, et al. 2005, Gene 364:79-89). As such, integration of genes at an expression enhancing locus (e.g., within or near SEQ ID NO: 1, or SEQ ID NO: 2, or SEQ ID NO: 3) is expected to confer enhanced expression. In some embodiments, the host cells comprising an exogenous nucleic acid sequence encoding a bispecific antigen-binding protein integrated at a specific site within an enhanced expression locus exhibits high specific productivity. In other embodiments, the bispecific antigen-binding protein-encoding host cell has a specific productivity of at least 5, 6, 7, 8, 9, 10, 11, 12, 13, 14, 15, 20, 25, or 30 picogram/cell/day (pcd).

In some embodiments, an exogenous nucleic acid is integrated at a site within a locus that comprises the nucleotide sequence of SEQ ID NO: 1. In specific embodiments, the integration site is within, or within close proximity to, the nucleotide sequence of SEQ ID NO: 1. In particular embodiments, the integration site is at a position within SEQ II) NO: 1 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In other embodiments, the integration site is in a sequence that is selected from the group consisting of nucleotides 5,000-7,400, 5,000-6,500, 6,400-7,400 of SEQ ID NO: 1; and nucleotides 6,400-6,500 of SEQ ID NO: 1. In a specific embodiment, the integration site before, after, or within the "act" triplet of nucleotides 6471 to 6473 of SEQ II) NO: 1.

In some embodiments, an exogenous nucleic acid is integrated at a site within a locus that comprises the nucleotide sequence of SEQ II) NO: 2 or SEQ ID NO: 3. In specific embodiments, the integration site is within, or within close proximity to, the nucleotide sequence of SEQ ID NO: 2. In particular embodiments, the integration site is within, or within close proximity to, the nucleotide sequence of SEQ ID NO: 3. In some embodiments, the integration site is within nucleotides 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, 2020-2021 or 2021-2022 of SEQ ID NO: 3. In specific embodiments, the integration is at or within nucleotides 2001-2022 of SEQ ID NO: 3. In some embodiments, the exogenous nucleic acid is inserted at or within nucleotides 2001-2002 or nucleotides 2021-2022 of SEQ ID NO: 3 and nucleotides 2002-2021 of SEQ ID NO: 3 are deleted, as a result of the insertion.

Site-Specific Integration Into an Expression-Enhancing Locus

Integration of one or more exogenous nucleic acids into an expression-enhancing locus in a site-specific manner, i.e., into one specific site within an expression-enhancing locus as disclosed herein, can be achieved in several ways including, e.g., by homologous recombination, and recombinase mediated cassette exchange, as described in the art (see e.g., U.S. Pat. No. 8,389,239 and the art disclosed therein).

In some embodiments, cells are provided that contain at least two, i.e., two or more, different recombinase recognition sequences (RRS) within an expression-enhancing locus convenient for integrating an nucleic acid sequence containing one or more exogenous nucleic acids or genes of interest. Such cells can be obtained by introducing an exogenous nucleic acid sequence containing two or more RRS into a desirable locus by various means including homologous recombination, as described hereinbelow and in the art, e.g., U.S. Pat. No. 8,389,239 and the art disclosed therein.

In specific embodiments, cells are provided that contain more than two different recombinase recognition sequences (RRS) within an expression-enhancing locus convenient for integrating multiple exogenous nucleic acids. In particular embodiments, cells are provided that contain three different recombinase recognition sequences (RRS) within an expression-enhancing locus which can mediate integration of two separate exogenous nucleic acids, for example, wherein the 5' RRS and the middle RRS in the genome match the 5' RRS and the 3' RRS flanking the first exogenous nucleic acid to be integrated, and the middle RRS and 3' RRS in the genome match the 5' RRS and the 3' RRS flanking the second exogenous nucleic acid to be integrated.

Suitable RRSs can be selected from the group comprising LoxP, Lox511, Lox5171, Lox2272, Lox2372, Loxm2, Lox-FAS, Lox71, Lox66 and the mutants thereof, where the site specific recombinase is Cre recombinase or its derivative is used to achieve recombinase-mediated cassette exchange (RMCE). In other examples, suitable RRS can be selected from the group comprising FRT, F3, F5, FRT mutant-10, FRT mutant+10 and the mutants thereof, and in this scenario, the site-specific recombinase Flp recombinase or its derivative is used to achieve RMCE. In yet another example, RRSs can be selected from the group comprising attB, attP and the mutants thereof, and in this case where the site-specific recombinase phiC31 integrase or its derivative is used to achieve RMCE.

In other embodiments, native cells are modified by a homologous recombination technique to integrate a nucleic acid sequence containing one or more exogenous nucleic acids into a specific site within an expression-enhancing locus.

For homologous recombination, homologous polynucleotide molecules (i.e. homologous arms) line up and exchange a stretch of their sequences. A transgene can be introduced during this exchange if the transgene is flanked by homologous genomic sequences. In one example, a recombinase recognition site can be introduced into the host cell genome at the integration sites via homologous recombination. In other examples, a nucleic acid sequence containing one or more exogenous nucleic acids of interest, e.g., one or more nucleic acids each encoding an HCF or LCF (such as a variable region), wherein the nucleic sequence is flanked by sequences homologous to the sequences at the target locus ("homologous arms"), is inserted into the host genome.

Homologous recombination in eukaryotic cells can be facilitated by introducing a break in the chromosomal DNA at the integration site. This may be accomplished by targeting certain nucleases to the specific site of integration. DNA-binding proteins that recognize DNA sequences at the target locus are known in the art. Gene targeting vectors are also employed to facilitate homologous recombination.

Gene targeting vector construction and nuclease selection to achieve homologous recombination are within the skill of the artisan to whom this invention pertains. In some examples, zinc finger nucleases (ZFNs), which have a modular structure and contain individual zinc finger domains, recognize a particular 3-nucleotide sequence in the target sequence (e.g. site of targeted integration). Some embodiments can utilize ZFNs with a combination of individual zinc finger domains targeting multiple target sequences. Transcription activator-like (TAL) effector nucleases (TALENS) may also be employed for site-specific genome editing. TAL effector protein DNA-binding domain is typically utilized in combination with a non-specific cleavage domain of a restriction nuclease, such as FokI. In some embodiments, a fusion protein comprising a TAL effector protein DNA-binding domain and a restriction nuclease cleavage domain is employed to recognize and cleave DNA at a target sequence within the locus of the invention (Boch J et al., 2009 *Science* 326:1509-1512). RNA-guided endonucleases (RGENs) are programmable genome engineering tools that were developed from bacterial adaptive immune machinery. In this system—the clustered regularly interspaced short palindromic repeats (CRISPR)/CRISPR-associated (Cas) immune response—the protein Cas9 forms a, sequence-specific endonuclease when complexed with two RNAs, one of which guides target selection. RGENs consist of components (Cas9 and tracrRNA) and a target-specific CRISPR RNA (crRN.A). Both the efficiency of DNA target cleavage and the location of the cleavage sites vary based on the position of a protospacer adjacent motif (PAM), an additional requirement for target recognition (Chen, H. et al, *J. Biol. Chem.* published online Mar. 14, 2014, as Manuscript M113.539726). Sequences unique for a specific targeting locus (such as SEQ ID NO: 1, SEQ ID NO: 2, or SEQ ID NO: 3) can be identified by aligning many of these sequences to the CHO genome which can reveal potential off-target sites with 16-17 base pair match.

In some embodiments, a targeting vector carrying a nucleic acid of interest (e.g., a nucleic acid containing one or more RRSs optionally flanking one or more selectable marker genes, or a nucleic acid containing one or more exogenous nucleic acids each encoding an HCF or LCF (such as a variable region), flanked by 5' and 3' homology arms, is introduced into a cell with one or more additional vectors or mRNA. In one embodiment, the one or more additional vectors or mRNA contain a nucleotide sequence encoding a site-specific nuclease, including but not limited to a zinc finger nuclease (ZFN), a ZFN dimer, a transcription activator-like effector nuclease (TALEN), a TAL effector domain fusion protein, and an RNA-guided DNA endonuclease. In certain embodiments, the one or more vectors or mRNA include a first vector comprising a guide RNA, a tracrRNA and a nucleotide sequence encoding a Cas enzyme, and a second vector comprising a donor (exogenous) nucleotide sequence. Such donor sequence contains a nucleotide sequence coding for the gene of interest, or the recognition sequence, or the gene cassette comprising any one of these exogenous elements intended for targeted insertion. Where snRNA is used, the mRNA can be transfected into the cell by means of common transfection methods known to the skilled person and may encode an enzyme, for example a transposase or endonuclease. Although an mRNA introduced into the cells may be transient and does not integrate into the genome, the mRNA may carry an exogenous nucleic acid necessary or beneficial for the integration to take place. In some instances, mRNA is chosen in order to eliminate any risk of long-lasting side effects of an accessory polynucleotide, where only short-term expression is required to achieve the desired integration of a nucleic acid.

Vectors for Site Specific Integration

Nucleic acid vectors are provided herein for introducing exogenous nucleic acids into two expression enhancing loci via site-specific integration. Suitable vectors include vectors designed to contain an exogenous nucleic sequence flanked by RRSs for integration via RMCE, and vectors desigmed to contain an exogenous nucleic sequence of interest flanked by homology anus for integration via homologous recombination.

In various embodiments, vectors are provided to achieve site-specific integration via RMCE. In some embodiments, vectors are designed to achieve simultaneous integration of multiple nucleic acids into two target loci. In contrast to sequential integration, simultaneous integration permits efficiency and rapid isolation of desirable clones that produce antigen-binding proteins, or other multimeric proteins of interest, suitable for large scale production (manufacturing).

In some embodiments, a set of vectors is provided for expressing a bispecific antigen-binding protein in a cell.

In some embodiments, a vector set can include two "HCF vectors", each containing a nucleic acid flanked by a 5' RRS and a 3' RRS, where the nucleic acid includes a nucleotide sequence encoding a HCF and wherein the two HCFs are different. The RRS on the two HCF vectors are different from each other, and are designed to integrate HCF-encoding nucleotide sequences to two expression-enhancing loci. The vector set also includes a nucleotide sequence encoding a LCF, which can be included in one of the HCF vectors, or in both HCF vectors (thereby providing two copies of the same LCF), or alternatively, provided in a separate "LCF vector" and flanked by a 5' RRS and a 3' RRS.

In some embodiments, the LCF-coding nucleotide sequence is included in one of the HCF vectors and positioned between the 5' RRS and the 3' RRS on that HCF vector. The LCF-coding sequence can be placed upstream or downstream of the HCF-coding sequence.

In some embodiments, the LCF-coding nucleotide sequence is included both of the HCF vectors and positioned between the 5' RRS and the 3' RRS on each HCF vector. Similarly, the LCF-coding sequence can be placed upstream or downstream of the HCF-coding sequence in each vector.

In some embodiments, the LCF-coding nucleotide sequence is provided in a separate vector, a "LCF" vector, and is flanked by a 5' RRS and a 3' RRS, with the two RRS being different from each other. The RRSs in the vector set can be designed such that the LCF-coding sequence can be "joined" with one of the HCF-coding sequences through a common RRS during RMCE with a target locus that also contains the common RRS. For example, the 3' RRS of the LCF vector can be the same as the 5' RRS of one the HCF vectors, giving rise to a LCF-HCF arrangement after integration at a target locus via RMCE. In another example, the 3' RRS of a HCF vector can be the same as the 5' RRS of the LCF vector, giving rise to a HCF-LCF arrangement after integration at a target locus via RMCE. In some embodiments, the common RRS is designed in a split selectable marker format—that is, it is included at the 3' end of a 5' portion of a selectable marker gene included in one vector, and also included at the 5' end of the remaining, 3' portion of the same selectable marker gene included in another vector, such that upon "joining" and integration into a target locus, the properly integrated nucleic acid includes the entire selectable marker gene to allow for convenient identification of transfectants. In some embodiments, the common RRS is designed in a split gene format, i.e., included at the 3' end of a 5' portion of an gene or intron within such split gene as part of a 5' portion of said gene on one vector, and at the 5' end of the remaining portion of the gene or intron within such split gene as part of the remaining 3' portion of said split gene. In still other embodiments, the third or middle RRS in a first vector is designed to be between a promoter and the selectable marker gene to which it is operably linked (but it is separated from on the other vector); the third or middle RRS in the first vector is designed to be 3' of a promoter; and the third or middle RRS in the second vector is designed to be 5' of the selectable marker gene.

Figure 3:
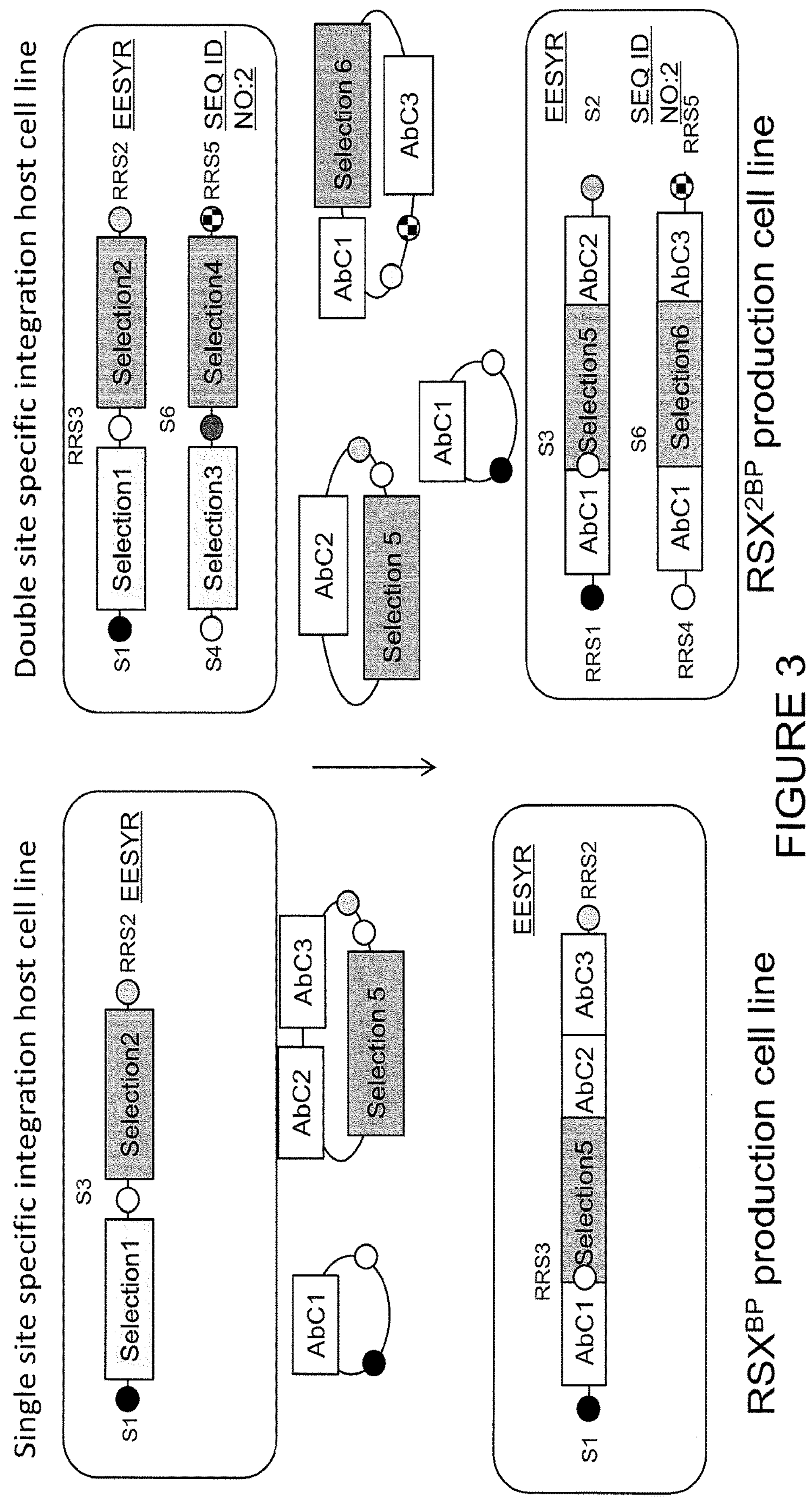
FIG. 3. An exemplary antibody cloning strategy for integration within one expression enhancing locus compared to integration within two separate expression enhancing loci for a bispecific antibody encoded by three antibody chains. Three vectors were utilized for this bispecific strategy, a first vector carrying a nucleic acid encoding antibody chains 1 (AbC1), for example a common light chain, flanked by RRS1 and RRS3, for integration into EESYR®, (SEQ ID NO:1; Locus 1); a second vector carrying antibody chain 2 (AbC2), for example a heavy chain, having an upstream selection marker, flanked by RRS4 and RRS6, for integration into the SEQ ID NO:2 locus; and additionally a third vector carrying a nucleic acid encoding a second copy AbC1 linked to a different selection marker than in the second vector and linked to antibody chain 3 (AbC3), for example a second (different) heavy chain, flanked 5' by RRS4 and 3' by RRS5 in the vector cassette (5' and 3' RRSs matched to the RRS sites in the host cell at the locus comprising SEQ ID NO:2). The two vector system as shown may be utilized for site-specific integration at a single locus, such as the EESYR® locus (comprising SEQ NO:1; Locus 1). Titers from the respective production cell lines were analyzed, see FIG. 5.
Figure 4:
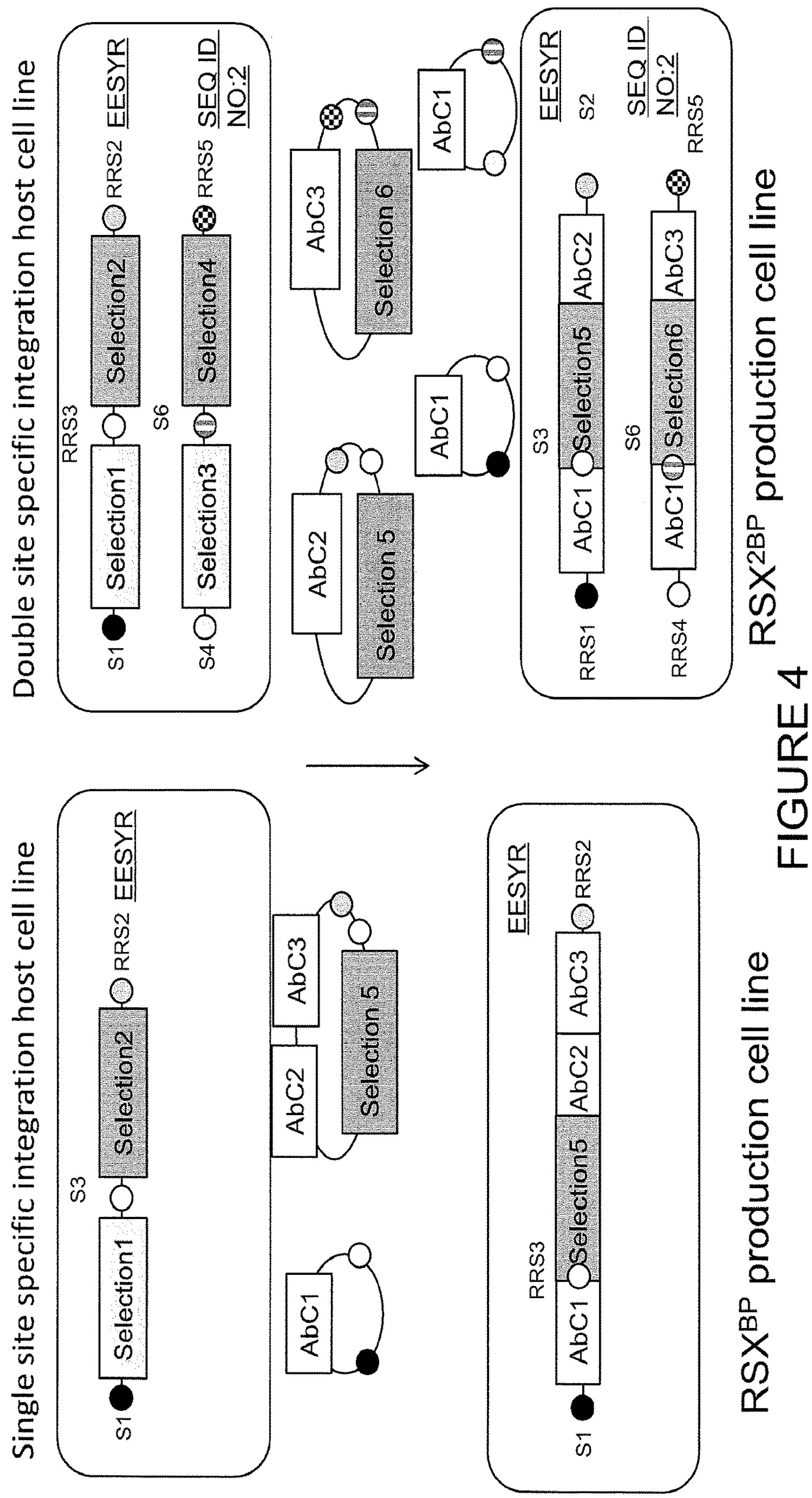
FIG. 4. An exemplary antibody cloning strategy for integration within one expression enhancing locus compared to integration within two separate expression enhancing loci for a bispecific antibody encoded by three or four antibody chains. Four vectors are utilized for this bispecific strategy, a first vector carrying a nucleic acid encoding antibody chain 1 (AbC1), for example a first light chain, flanked by RRS1 and RRS3, for integration into EESYR® (SEQ ID NO:1; Locus 1); a second vector carrying antibody chain 2 (AbC2), for example a heavy chain, having an upstream selection marker, flanked 5' by RRS3 and 3' by RRS2, for integration also into the EESYR® locus (comprising (SEQ ID NO:1; Locus 1); and a third vector carrying a nucleic acid encoding a different selection marker than in the second vector and linked to antibody chain 3 (AbC3), for example a second (different) heavy chain, flanked 5' by RRS6 and 3' by RRS5 in the vector cassette (5' and 3' RRSs matched to the RRS sites in the host cell at the locus comprising SEQ ID NO: 2; Locus 2); and additionally a fourth vector carrying a nucleic acid encoding a second light chain, for example antibody chain 1 (AbC1) (however may be the same or different than first light chain). The four vector system as shown may be utilized for site-specific integration at two loci, such as the EESYR® locus (comprising SEQ ID NO:1; Locus 1) and a locus comprising SEQ ID NO:2 or 3. The four vector system is compared to a two vector system integration at one locus (the EESYR® locus; Locus 1).

In some embodiments, the vector set can include an additional nucleotide sequence encoding a LCF. That is, the vector set can include two HCF vectors, and two LCF-encoding nucleotide sequences. The two LCF-encoding sequences can encode the same or different LCF. In some embodiments, the two LCF-encoding sequences can be each included into a HCF vector, resulting in two vectors, each containing a HCF-coding sequence and a LCF-coding sequence. The two vectors can be designed to have RRSs suitable for targeting the two vector sequences into two loci. In other embodiments, one of the two LCF-encoding sequences is included into a HCF vector and positioned between the 5' RRS and the 3' RRS on that HCF vector, and the other LCF-encoding sequence is provided on a separate vector—that is, one vector having both LCF and HC (in LCF-HCF or HCF-LCF arrangement, or in short a "LCF/HCF vector"), one HCF vector, and one LCF vector. In some of these other embodiments, the vector RRSs can be designed to permit joining of the HCF-coding sequence on the HCF vector and the LCF-coding sequence on the LCF vector at a target locus via RMCE. For example, the 3' RRS of the LCF vector can be the same as the 5' RRS of the HCF vector, and the common RRS can be designed in a split selectable marker or split intron format to facilitate selection and identification of transthetants. In still other embodiments, where the two LCFs are different, the two LCF-coding nucleotide sequences can each be provided on a separate vector—that is, the vector set includes two HCF vectors, and two LCF vectors. RRSs can be designed to permit proper "joining" of one LCF-coding sequence with one HCF-coding sequence at one target locus, and the other LCF-coding sequence with the other HCF-coding sequence at a second target locus. FIGS. 1, 3 and 4 are illustrative of different formats of vectors and RRS/loci combinations and not meant to be limiting. Each given vector system provides a means for simultaneously integrating each nucleotide sequence in the presence of a recombinase for the rapid and convenient selection of positive integrants (desired clones).

The nucleotide sequences encoding an HCF or LCF can encode amino acids or domain(s) from a constant region, or encode an entire constant region. In specific embodiments, a nucleotide sequences encoding an HCF or La can encode one or more constant domains, such as CL, CH1, hinge, CH2, CH3, or combinations thereof. In certain embodiments, a nucleotide sequence encoding a HCF domain can encode a CH3 domain. For example, the nucleotide sequence encoding the first HCF can encode a first CH3 domain, and the nucleotide sequence encoding the second HCF can encode a second CH3 domain. The first and second CH3 domains can be the same, or differ in at least one amino acid. The differences in the CH3 domains or in the constant regions can take any of the formats for bispecific antigen-binding proteins described herein, e.g., differences that result in different Protein A binding characteristics, or in a "knob-and-hole" format. Independent of any amino acid sequence differences, the two HCF-coding nucleotide sequences can also differ in that one of the two nucleotide sequences has been codon modified.

In some embodiments, each HCF or LCF-coding nucleotide sequence is independently and operably linked to a transcriptional regulatory sequence including e.g., a promoter. In some embodiments, the promoters directing transcription of the two -HCF-containing polypeptides are the same. In some embodiments, the promoters directing transcription of the two HCF-containing polypeptides, as well as the promoter directing transcription of the LCF-containing polypeptide, are all the same (e.g., a CMV promoter, or any other suitable promoter described herein). In some embodiments, each HCF- or LCF-coding nucleotide sequence is independently and operably linked to an inducible or repressible promoter. Inducible or repressible promoters allow production to occur, for example, only in production phase (fed-batch culture) and not during growth phase (seed train culture). Inducible or repressible promoters also allow for differential expression of one or more genes of interest. In some embodiments, each HCF- and/or LCF-coding nucleotide sequence is independently and operably linked to a promoter upstream of at least one TetR operator (TetO) or Arc operator (ArcO). In still other embodiments, each HCF- and/or LCF-coding nucleotide sequence is independently and operably linked to a CMV/TetO or CMV/ArcO hybrid promoter. Examples of hybrid promoters (also referred to as regulatory fusion proteins) may be found in international Publication No. WO03101189A1, published Dec. 11, 2003 (herein incorporated by reference).

In some embodiments, the vector set includes a nucleotide sequence encoding a recombinase that recognizes one or more RRSs, which can be included in one of the HCF or LCF-coding vectors, or provided in a separate vector.

In various other embodiments, vectors are provided to achieve site-specific integration via homologous recombination.

In some embodiments, a vector set is provided that includes two vectors, each containing an exogenous nucleic acid, flanked by a 5' homology arm and a 3' homology arm, for site-specific integration into two expression enhancing loci in a cell, wherein the exogenous nucleic acids from the two vectors together encode an antigen binding protein. Thus, the homology arms on one vector are designed for integration into one of the two loci, and the homology arms on the other vector are designed for integration into the other locus. In these embodiments, the antigen-binding protein can be monospecific or bispecific.

It is well within the skill of the artisan to select sequences homologous to sequences within an expression enhancing locus and include the selected sequences as homology arms in a targeting vector. In some embodiments, the vector or construct comprises a first homologous arm and a second homologous arm, wherein the first and second homologous aims combined comprise a targeted sequence which replaces an endogenous sequence within the locus. In other embodiments, the first and second homologous arms comprise a targeted sequence which integrates or inserts within an endogenous sequence within the locus. In some embodiments, the homology arms contain a nucleotide sequence homologous to a nucleotide sequence present in SEQ ID NO: 1, SEQ ID NO: 2, or SEQ ID NO: 3. In specific embodiments, the vector contains a 5' homology arm having the nucleotide sequence corresponding to nucleotides 1001-2001 of SEQ ID NO: 3, and a 3' homology arm having the nucleotide corresponding to nucleotides 2022-3022 of SEQ ID NO: 3. Homologous arms, for example a first homologous arm (also called 5' homology arm) and a second homologous arm (also called 3' homology arm) are homologous to a targeted sequence within the locus. The homologous arms from 5' to 3' may expand a region or targeted sequence within the locus that comprises at least 1 kb, or at least about 2 kb, or at least about 3 kb, or at least about 4 kb, or at least 5 kb, or at least about 10 kb. In other embodiments, the total number of nucleotides of a targeted sequence selected for a first and second homologous arm comprises at least 1 kb, or at least about 2 kb, or at least about 3 kb, or at least about 4 kb, or at least 5 kb, or at least about 10 kb. In some instances, the distance between the 5' homology arm and the 3' homology arm (homologous to the targeted sequence) comprises at least 5 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 hp, 800 bp, 900 bp, or at least 1 kb, or at least about 2 kh, or at least about 3 kb, or at least about 4 kb, or at least 5 kb, or at least about 10 kb. In instances where nucleotides 1001-2001 and 2022-3022 of SEQ ID NO: 3 are chosen as 5' and 3' homology arms, the distance between the two homology arms can be 20 nucleotides (corresponding to nucleotides 2002-2021 of SEQ ID NO: 3); and such homology arms can mediate integration of an exogenous nucleic acid sequence within a locus comprising SEQ ID NO: 3, e.g., within nucleotides 1990-2021 or 2002-2021 of SEQ ID NO: 3, and a simultaneous deletion of nucleotides 2002-2021 of SEQ ID NO: 3.

The vectors disclosed herein for introducing exogenous nucleic acids for site-specific integration into an expression enhancing locus can include additional genes and sequences for directing the expression of exogenous nucleic acids of interest and encoded polypeptides and for the selection and identification of cells into which the exogenous nucleic acids of interest have successfully integrated. Such additional sequences include, for example, transcriptional and translational regulatory sequences selectable marker genes, and the like, also described hereinbelow.

Regulatory Sequences

The vectors disclosed herein for introducing exogenous nucleic acids into an expression enhancing locus in a site-specific manner, and the cells obtained as a result of site-specific integration, can include regulator sequences for directing the expression of exogenous nucleic acids of interest and encoded polypeptides. Regulatory sequences include transcriptional promoters, enhancers, sequences encoding suitable mRNA ribosomal binding sites, and sequences that control the termination of transcription and translation. Transcriptional and translational control sequences may be provided by viral sources. For example, commonly used promoters and enhancers are derived from viruses such as polyoma, adenovirus 2, simian virus 40 (SV40), mouse or human cytomegalovirus (CMV), CMV immediate early (CMV-IE) or CMV major IE (CMV-MIE) promoter, as well as RSV, SV40 late promoter, SL3-3, MMTV, ubiquitin (Ubi), ubiquitin C (UbC), and HIV LTR promoters. Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the proteins of interest are to be expressed. DNA sequences derived from the SV40 viral genome, for example, the SV40 origin, early and late promoter, enhancer, splice, and polyadenylation sites may be used to provide other genetic elements useful for expression of a exogenous DNA sequence. Early and late promoters are particularly useful because both are obtained easily from the SV40 virus as a fragment that also comprises the SV40 viral origin of replication (Tiers et al., *Nature* 273:113, 1978). Smaller or larger SV40 fragments may also be used. Typically, the approximately 250 by sequence extending from the Hind III site toward the BglI site located in the SV40 origin of replication is included. Inducible (induced by a chemical compound, cofactor, regulatory protein, for example) and/or repressible (repressed by a chemical compound, cofactor, regulatory protein, for example) promoters can be used and are particularly useful for allowing the production of antigen binding proteins to occur only in production phase (fed-batch culture) and not during growth phase (seed train culture), or to differentially control expression of antibody components in different loci with precision. Examples of inducible promoters include alcohol dehydrogenase I gene promoters, tetracycline-responsive promoter systems, glucocorticoid receptor promoters, estrogen receptor promoter, ecdysone receptor promoters, rnetallothionein-based promoters, and T7-polymerase based promoters. Examples of repressible promoters include hybrid promoters (also referred to as regulatory fusion proteins comprising a CMV or other promoter operably linked to at least one TetR operator (TetO) or Arc operator (ArcO), and are described in International Publication No. WO03101189A1, published Dec. 11, 2003 (herein incorporated by reference). Sequences suitable for the expression of multiple transcripts via a bicistronic vector have been described previously (Kim S. K. and Wold B. J., *Cell* 42:129, 1985) and can be used this invention. Examples of suitable strategies for multicistronic expression of proteins include the use of a 2A peptide (Szymczak et al., *Expert Opin Biol Ther* 5: 627-638 (2005)) and the use of an internal ribosome entry site ("IRES"), both well known in the art. Other types of expression vectors will also be useful, for example, those described in U.S. Pat. No. 4,634,665 (Axel et al.) and U.S. Pat. No. 4,656,134 (Ringold et al.).

Selectable Markers

The vectors disclosed herein for introducing exogenous nucleic acids into an expression enhancing locus in a site-specific manner, and the cells obtained as a result of site-specific integration, can include one or more selectable markers genes.

In some embodiments, a selectable marker gene confers drug resistance, such as, for example, those described in Table 1 of Kaufman, R. J. (1988) *Meth. Enzymology* 185: 537, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin. Other dominant selectable markers include microbially derived antibiotic resistance genes, for example neomycin, kanamycin or hygromycin resistance. Several suitable selection systems exist for mammalian hosts (Sambrook supra, pgs 16.9-16.15). Co-transfection protocols employing two dominant selectable markers have also been described (Okayama, and Berg, *Mol. Cell Biol* 5:1136, 1985).

In other embodiments, a selectable marker gene encodes a polypeptide that provides or is capable of generating a detectable signal for the recognition of gene cassettes that have or have not been successfully inserted and/or replaced, as the case may be. Suitable examples include a fluorescent marker or protein, an enzyme that catalyzes a chemical reaction that generates a detectable signal, among others. Examples of fluorescent markers are well-known in the art, including, but not limited to *Discosoma* coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson. See also, e.g., Nagai, T., et al. 2002 *Nature Biotechnology* 20:87-90; Heim, R. et al. 23 Feb. 1995 *Nature* 373:663-664; and Strack, R. L. et al. 2009 *Biochemistry* 48:8279-81.

Systems for Making Antigen-Binding Proteins

In a further aspect, this disclosure provides systems that include a combination of a cell (e.g., a CHO cell) with one or more vectors, and that can be utilized to make cells having integrated within two expression enhancing loci exogenous nucleic acids that together encode an antigen binding protein, either a monospecific protein or a bispecific protein. The systems can be provided in the form of a kit, for example.

In some embodiments, a system is designed to permit efficient vector construction and simultaneous integration of multiple exogenous nucleic acids via RMCE into specific sites within two enhanced expression loci. Simultaneous integration permits rapid isolation of desirable clones, and the use of two enhanced expression loci is also important for creation of a stable cell line suitable for protein production (e.g. commercially-enabled cell line).

The system provided herein includes a cell and a set of vectors. The cell contains a pair of RRSs (a 5' RRS and a 3' RRS) integrated within each of two enhanced expression loci. In some embodiments, an exogenous nucleic acid is present between the 5' RRS and the 3' RRS at each locus, and can include, e.g., one or more selectable marker genes. The vector set includes at least two vectors, with each vector containing a pair of RRSs (a 5' RRS and a 3' RRS) flanking a nucleotide sequence encoding an HCF or LCF, and with the nucleotide sequence on one of the two vectors encoding an HCF (an HCF vector), and the nucleotide sequence on the other of the two vectors encoding an LCF (an LCF vector), and wherein the HCF and LCF are regions of an antigen-binding protein. The 5' RRS and 3' RRS within each pair of RRSs are different, and the RRSs in the system are designed such that upon introduction of the vectors into the cell, the HCF or LCF-encoding nucleotide sequences in the vectors integrate into the two enhanced expression loci through RMCE mediated by the RRSs to express the antigen-binding protein. Depending on whether the antigen-binding protein, the number of vectors, the placement of HCF or LCF-coding sequences, and the relationship among the RRSs, can be designed differently.

In some embodiments, the system is designed for integration into two expression enhancing loci and expression of monospecific antigen-binding proteins. In some embodiments, the 5' RRS and the 3' RRS on one of the two vectors (i.e., an HCF vector and an LCF vector) are identical to the 5' RRS and the 3' RRS in one of the two loci, respectively, and the 5' RRS and the 3' RRS on the other vector are identical to the 5' RRS and the 3' RRS in the other locus, respectively, essentially targeting the HCF and LCF nucleic acids separately to the two loci, one to each. In other embodiments, the HCF coding sequence and the LCF coding sequence, while on separate vectors, are designed for integration jointly into each of the two loci. According to these embodiments, the 5' RRS and the 3' RRS in the first locus are the same as the 5' RRS and the 3' RRS in the second locus, respectively; and each locus also contains an additional RRS between the 5' and 3' RRSs ("middle RRS"). In addition, the 5' RRS in a first the two vectors is the same as the 5' RRS in the first and second loci, the 3' RRS in that first vector is the same as the 5' RRS in the second vector and as the middle RRS in the first and second loci, and the 3' RRS is the second vector is the same as the 3' RRS in both loci. The vectors can be designed to have a split promoter and selection marker format (the promoter on one vector and the selection marker to which the promoter is operably linked on another vector). The vectors can be designed to have a split selectable marker format, or a split intron format, as described above, to facilitate selection of transfectants with proper integration. Further, the system can be designed to allow different relative positions of the LCF-coding sequence and the HCF-coding sequence after integration. In some embodiments, the system is designed to have the LCF-coding sequence integrated upstream of the HCF-coding sequence. In other embodiments, the system is designed to have the LCF-coding sequence integrated upstream of the HCF-coding sequence.

In some embodiments, the system is designed for integration into two expression enhancing loci and expression of bispecific antigen-binding proteins.

In some embodiments, in addition to a HCF vector (encoding a first HCF) and a LCF vector (encoding a first LCF), the system also includes a nucleotide sequence encoding a second HCF that is different from the first HCF. The nucleotide sequence encoding the second HCF can be included, for example, in the LCF vector, or in a separate vector, i.e., a second HCF vector. In some embodiments, the second HCF-coding sequence is included in the LCF vector between the 5' RRS and 3' RRS on the LCF vector, in which case, the system includes a HCF vector and a LCF/HCF vector. The system, especially the RRSs, can be designed to integrate the HCF-coding sequence into one of the two loci, and the sequence that encodes both HCF and LCF into the other locus. In other embodiments, the nucleotide sequence encoding the second HCF is on a separate vector, flanked by a 5' RRS and a 3' RRS, in which case the system includes two HCF vectors and one LCF vector. In these other embodiments, the RRSs in the system can be designed such that the LCF-coding sequence can be "joined" via RMCE with one of the HCF-coding sequences through a common RRS which is also present in one of the two loci between the 5' RRS and the 3' RRS in that locus, and the other HCF-coding sequence will integrate into the other of the two loci. For example, the 3' RRS of the LCF vector can be the same as the 5' RRS of one the HCF vectors and also as a middle RRS on one of the two loci—this design will give rise to a LCF-HCF arrangement after integration into the locus having the middle RRS. In another example, the 3' RRS of a HCF vector can be the same as the 5' RRS of the LCF vector and as a middle RRS on one of the two loci, giving rise to a HCF-LCF arrangement after integration at the locus having the middle RRS. In some embodiments, the common RRS is designed in a split selectable marker format or a split intron format, as described hereinabove.

In some embodiments, the system also includes a nucleotide sequence encoding a. second LCF, in addition to a HCF vector (encoding a first HCF) and a LCF vector (encoding a first LCF), and a nucleotide sequence encoding a second HCF that is different from the first HCF. That is, the system includes four, separate coding sequences, two encoding HCF and two encoding LCF. The two LCFs can be the same or different. The four coding sequences can be placed in vectors in different designs. In some embodiments, the four sequences are placed in two vectors: LCF/HCF, and LCF/HCF, with LCF either upstream or downstream of HCF in either vector. The system (RRSs) can be designed such that one vector sequence integrates into one locus, and the other vector sequence integrates into the other locus. In some embodiments, the four sequences are placed in three vectors: LCF, HCF, and LCF/HCF (with LCF either upstream or downstream of HCF). The RRSs in the system can be designed such that the sequences in the LCF/HCF vector integrate into one locus, and the LCF coding sequence in the LCF vector and the HCF coding sequence in the HCF vector integrate into the other locus by utilizing a common RRS shared by the LCF vector, the HCF vector and this other locus. Similarly, the common RRS can be designed in a split marker or split intron format. In some embodiments, the four sequences are placed in four vectors: LCF, LCF, and HCF. The RRSs in the system can be designed such that the LCF coding sequence in one of the LCF vectors and the HCF coding sequence in one of the HCF vectors integrate jointly into one locus by utilizing a common RRS, and the LCF coding sequence in the other of the LCF vectors and the HCF coding sequence in the other of the HCF vectors integrate jointly into one locus by utilizing a common RRS.

In various embodiments of the system provided herein, the nucleotide sequences encoding an HCF or LCF can encode amino acids, e.g., amino acids or domain(s) from a constant region, or encode an entire constant region. In specific embodiments, a nucleotide sequences encoding an HCF or LCF can encode one or more constant domains, such as CL, CH1, CH2, CH3, or combinations thereof. In certain embodiments, a nucleotide sequence encoding a HCF domain can encode a CH3 domain. For example, the nucleotide sequence encoding the first HCF can encode a first CH3 domain, and the nucleotide sequence encoding the second HCF can encode a second CH3 domain. The first and second CH3 domains can be the same, or differ in at least one amino acid. The differences in the CH3 domains or in the constant regions can take any of the formats for bispecific antigen-binding proteins described herein, e.g., differences that result in different Protein A binding characteristics, or in a "knob-and-hole" format. Independent of any amino acid sequence differences, the two HCF-coding nucleotide sequences can also differ in that one of the two nucleotide sequences has been codon modified.

In various embodiments of the system provided herein, each HCF or LCF-coding nucleotide sequence is independently and operably linked to a transcriptional regulatory sequence including e.g., a promoter. In some embodiments, the promoters directing transcription of the two HCF-containing polypeptides are the same. In some embodiments, the promoters directing transcription of the two HCF-containing polypeptides, as well as the promoter directing transcription of the LCF-containing polypeptide, are all the same (e.g., a CMV promoter, an inducible promoter, a repressible promoter, or any other suitable promoter described herein)

In some embodiments, the present system further includes a nucleotide sequence encoding a recombinase that recognizes one or more RRSs, which can be included in one of the variable region-coding vectors, or provided in a separate vector.

The systems disclosed herein are designed to permit efficient construction of vectors and rapid isolation of desirable clones, and the use of two enhanced expression loci is also important for creation of a stable cell line. In some embodiments, a system is designed to utilize negative selection for identifying transformants having intended site-specific integration (e.g., lack of fluoresence resulting from one or more fluroscent marker genes in the host genome being removed following RMCE). One round of negative selection may take only two weeks; however, the efficiency of isolating clones with intended recombination may be limited (about 1%). If negative selection is combined with positive selection based on a new selection marker provided by an integrated nucleic acid(s) (such as a a new fluorescence marker, or resistance to a drug or antibiotic, in a split format for example), the efficiency of isolating clones with intended recombination can be significantly improved (to about 40% up to about 80%). The systems can include additional components, reagents, or information, for examples, protocols for introducing the vector(s) in a system into the cell of the system by transfection. Non-limiting transfection methods include chemical-based transfection methods include the use of liposomes; nanoparticles; calcium phosphate (Graham et al. (1973) *Virology* 52 (2): 456-67, Bacchetti et al. (1977) *Proc Natl Acad Sci USA* 74 (4): 1590-4 and, Kriegler, M (1991) Transfer and Expression: A Laboratory Manual. New York: W. H. Freeman and Company. pp. 96-97); dendrimers; or cationic polymers such as DEAE-dextran or polyethylenimine. Non chemical methods include electroporation; sono-poration; and optical transfection. Particle-based transfection include the use of a gene gun, magnet assisted transfection (Bertram, J. (2006) *Current Pharmaceutical Biotechnology* 7, 277-28). Viral methods can also be used for transfection. MRNA delivery includes methods using TransMessenger™ and TransIT® (Bire et al. *BMC Biotechnology* 2013, 13:75). One commonly used method of introducing heterologous DNA into a cell is calcium phosphate precipitation, for example, as described by Wigler et al. (*Proc. Natl. Acad. Sci. USA* 77:3567, 1980). Polyethylene-induced fusion of bacterial protoplasts with mammalian cells (Schaffner et al., (1980) *Proc. Natl. Acad. Sci. USA* 77:2163) is another useful method of introducing heterologous DNA. Electroporation can also be used to introduce DNA directly into the cytoplasm of a host cell, for example, as described by Potter et al. (*Proc. Natl. Acad. Sci. USA* 81:7161, 1988) or Shigekawa et al. (BioTechniques 6:742, 1988). Other reagents useful for introducing heterologous DNA into a mammalian cell have been described, such as Lipofectin™ Reagent and Lipofectamine™ Reagent (Gibco BRL, Gaithersburg, Md.). Both of these commercially available reagents are used to form lipid-nucleic acid complexes (or liposomes) which, when applied to cultured cells, facilitate uptake of the nucleic acid into the cells.

Methods for Making Antigen-Binding Proteins

This disclosure also provides methods of making bispecific antigen-binding proteins. By utilizing the methods disclosed herein, a desired antigen-binding protein can be produced at high titers and/or high specific productivity (pgicelliday). In some embodiments, an antigen-binding protein is produced at a titer of at least 1 g/L, 1.5 g/L, 2.0 g/L. 2.5 g/L, 3.0 g/L, 3.5 g/L, 4.0 g/L, 4.5 g/L, 5.0 g/L, 10 g/L, or greater. In some embodiments, an antigen-binding protein is produced at a specific productivity of at least 5, 6, 7, 8, 9, 10, 11, 12, 13, 14, 15 picogram/cell/day (pcd), or higher, determined based on total antigen-binding proteins (in pg) produced per cell per day. In some embodiments, a bispecific antigen-binding protein is produced at a ratio of the bispecific antigen-binding protein titer versus the total antigen-binding protein titer of at least 5%, 10%, 15%, 20%, 25%, 30%, 35%, 40%, 50%, 60% or higher.

In one embodiment, the method utilizes a system disclosed herein and introduces the vectors in the system into the cell of the system by transfection. Transfected cells where the exogenous nucleic acids have been properly integrated into two enhanced expression loci of the cell through RMCE can be screened and identified. In some embodiments, identification of transfected cells is achieved by negative selection against one or more selection markers present in a host cell before the transfection. In other embodiments, identication of transfected cells is achieved by negative selection against one or more selection markers present in a host cell before the transfection, in combination with positive selection based on one or more selection markers provided by the nucleic acids in the vectors that are designed to be integrated. HCE-containing polypeptides and LCF-containing polypeptides can be expressed from the integrated nucleic acids, and the antigen-binding protein of interest can be obtained from the identified transfected cell, and purified using known methods.

In another embodiment, the method simply utilizes a cell described hereinabove, which contains exogenous nucleic acids integrated at two enhanced expression loci that together encode an antigen-binding protein, and expresses the antigen-binding protein from the cell. Each cloned expression cassette(s) is contiguous within each specific integration site.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1

Expression of Monospecific Antibodies (Abs) in Two Specific Expression Enhancing Loci (via Site-Specific Integration)

Ab chains (AbC1, AbC2) were cloned into vectors in which RSS sites are flanking the Ab expression cassettes and the expression cassette for the selectable marker as depicted in FIG. 1. Two Ab chains could be cloned into separate vectors or combined into one vector in which 2 expression cassettes are arranged in tandem in any one of the possible orders: AbC1, AbC2, and the selectable marker, for example AbC1 is equivalent to a conventional LC and AbC2 is equivalent to a conventional heavy chain.

Figure 2:
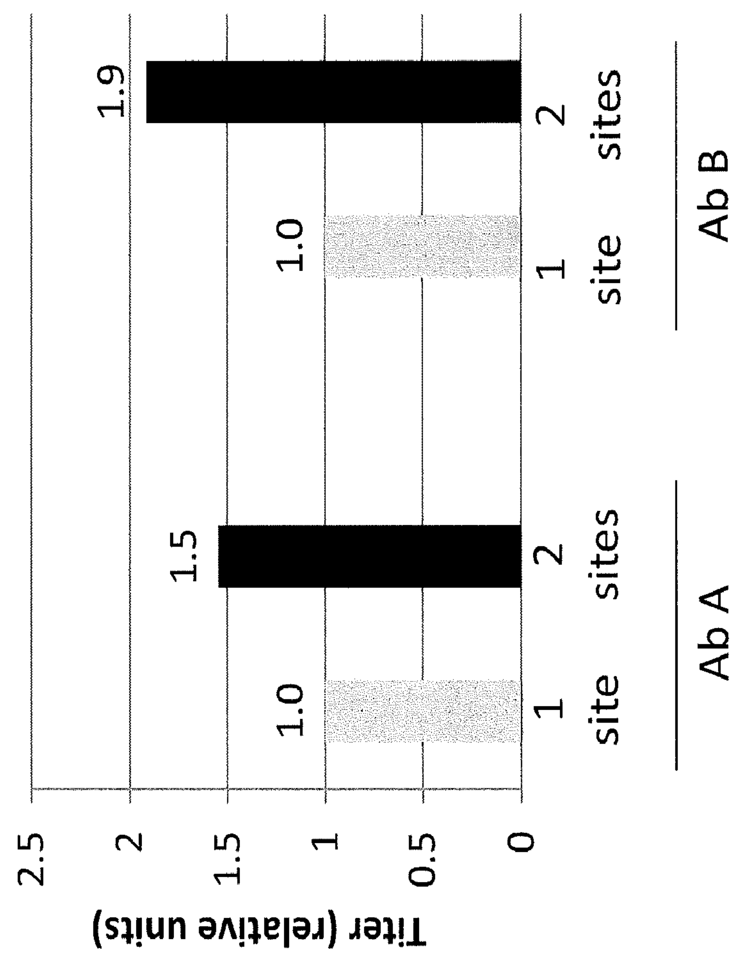
FIG. 2. Using the two vector cloning strategy for integration within one expression enhancing locus versus two loci, antibody A and antibody B were cloned into the loci as depicted in FIG. 1. Cells expressing antibody were isolated and subjected to 12 day fed batch culture, followed by harvest and an Octet titer assay using Protein A sensors. The cells were also observed to be isogenic and stable. Overall titer was observed to increase of 0.5 to 0.9 fold from utilization of the two site integration method.

Briefly, DNA encoding VH and VL domains may be isolated directly from single antigen positive B cells by PCR. Heavy chain and light chain PCR products were cloned into Sap I-linearized antibody vector containing IgG heavy chain constant region and kappa light chain constant region, respectively. The heavy chain plasmid (AbC2) has an RRS3 and an RRS2 site flanking the heavy chain expression cassettes. In addition, immediately downstream of the RRS3 in the heavy chain plasmid there is a split selection marker gene (e.g. U.S. Pat. No. 7,582,298). The light chain plasmid has a RRS1 and RRS3 site flanking the light chain expression cassette. In addition, the light chain plasmid has a strong promoter immediately before an ATG at the RRS3, such that upon integration into the host cell locus the RRS3-proximal promoter and initiating ATG from the light chain plasmid is brought adjacent to the selection marker gene in the heavy chain plasmid in the proper reading frame to allow transcription and translation of the selection gene. Purified recombinant plasmids having a heavy chain variable region sequence and plasmids having a light chain variable region sequence from the same B cell were then combined and transfected, together with a plasmid that expresses a recombinase, into a modified CHO host cell line having the appropriate RSSs and selection markers at the SEQ D NO:1 (EESYR®; Locus 1) and SEQ ID NO:2 loci. The modified CHO host cell line contains 4 different selection markers at two transcriptionally active loci. Consequently, where the selection markers are different fluorescent markers, the production CHO cell can be isolated by flow cytometry for positive-negative combinations that represent desired cell recombinants. When recombinant plasmids expressing heavy chain and light chain genes are transfected together with a plasmid expressing recombinase, site-specific recombination mediated by the recombinase results in the integration of the antibody plasmids at each chromosomal locus containing the RRSs and replacement. Accordingly, recombinant cells expressing monospecific antibody were isolated and subjected to 12 day fed batch production, followed by harvest and an Octet titer assay using immobilized Protein A. The cells were observed to be isogenic and stable. Overall titer in small shaker flask was observed to increase for the expression of monospecific antibodies when utilizing the two site integration method, with Antibody B resulting in a significant increase, nearly doubling titer (FIG. 2).

Example 2

Expression of Bispecific Antibodies (BsAbs) in Two Specific Expression Enhancing Loci (via Site-Specific Integration)

For the expression of bispecific antibodies, three antibody chains and two selectable markers were cloned into plasmids analogous to Example 1, such that AbC1, AbC2, and selectable marker 1 are flanked by RRS sites compatible with the first locus, or integration site (EESYR®, SEQ ID NO:1; Locus 1), and AbC1, AbC3, selectable marker 2 are compatible with the second locus, or integration site (SEQ ID NO:2). In our observations, AbC1 as a conventional LC does not require two gene copies for adequate expression. For each site, 1 or 2 plasmids were made, where the 3 expression cassettes are either arranged in tandem or arranged into 2 plasmids where 2 expression cassettes are cloned into one vector and the remaining expression cassette is cloned into the second vector. See FIG. 3.

Figure 5:
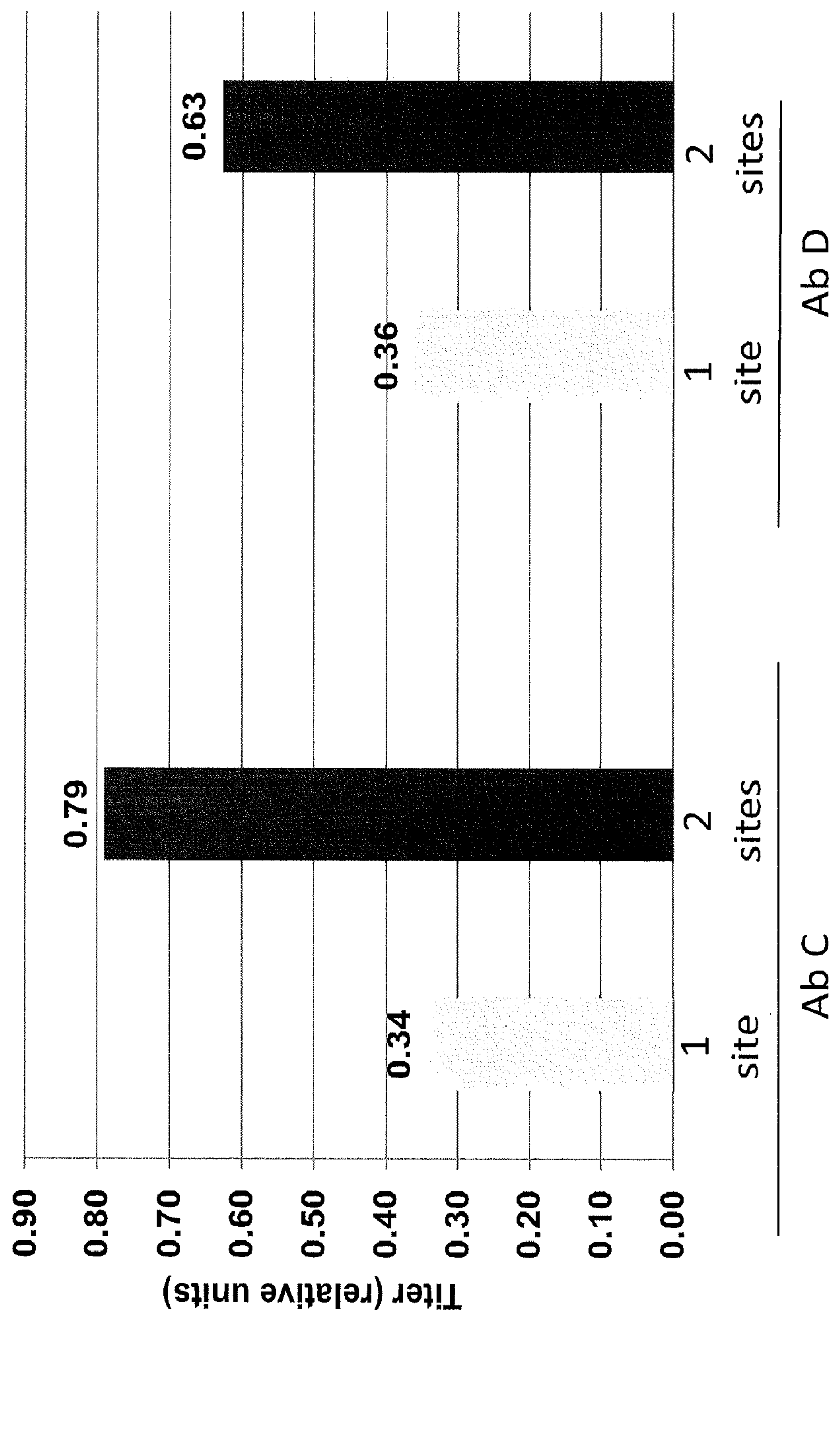
FIG. 5. Using the two vector cloning strategy for integration within one expression enhancing locus versus two loci, bispecific antibody C and bispecific antibody D were cloned, cells isolated and subjected to 12 day fed batch culture, followed by harvest and an Octet titer assay using immobilized anti-Fe, and a second anti-Fc* (modified Fc detection antibody, see US 2014-0134719 A1, published May 15, 2014). The cells were also observed to be isogenic and stable. Total bispecific titer (heterodimer formation) was observed to increase of 1.75 to 2 fold utilizing the two site integration method, compared to expression of the bispecific antibody (heterodimer) in one integration site.

When recombinant plasmids expressing the heavy chain and light chain genes are transfected together with a plasmid expressing recombinase, site-specific recombination mediated by the recombinase results in the integration of the antibody plasmids at each chromosomal locus containing the RRSs and replacement. Accordingly, recombinant cells expressing bispecific antibody were isolated and subjected to 12 day fed batch production, followed by harvest and an Octet titer assay using immobilized anti-Fc, and a second anti-Fc* (modified Fc detection antibody, see US 2014-0134719 A1, published May 15, 2014). The cells were observed to be isogenic and stable. Overall titer in small shaker flask was observed to increase significantly from 1.75 to more than 2 fold from utilization of the two site integration method (FIG. 5).

Example 3

Large Scale Production of Bispecific and Monospecific Antibodies Following Site-Specific Integration Host cells (CHO-K1) were created as described above analogous to Example 1 (see also FIG. 3 for bispecific antibodies and FIG. 1 for monospecific antibodies). Host cells enabled for RMCE of gene cassettes in the EESYR® locus (Locus 1) and SEQ ID NO: 2 (Locus 2) were compared to host cells enabled for RMCE of gene cassettes into only one integration site (Locus 1/EESYR®). Vectors carrying antibody light chain and heavy chains (AbC1, AbC2, AbC3) and the requisite RRS and selection marker nucleic acids (see FIG. 3) were recombined into production cell lines ($RSX^{2BP}$) to create host cells expressing Ab E, Ab Ab G, and Ab H. As such, each bispecific antibody host cell expresses one common light chain, and two heavy chains that bind different antigens where one of the heavy chains is engineered in its CH3 domain to differentially bind Protein A (as described in U.S. Pat. No. 8,586,713, herein incorporated by reference).

For monospecific antibodies, antibody light chain and heavy chain (AbC1, AbC2) were cloned into vectors in which RSS sites are flanking the Ab expression cassettes (and the expression cassette also provides a selectable marker gene) as depicted in FIG. 1. Recombination was perfumed to create host cells ($RSX^2$) expressing Ab J and Ab K.

2L, 15L, or 50L bioreactors were inoculated from a seed culture of the antibody-producing cell line $RSX^2$ derived from CHO-K1. The inoculated cells were grown at 36.5' C. for thirteen days and fed glucose and other supplemental nutrients as needed. Cells were grown in chemically defined (hydrolysate-free and serum-free) base media. Total antibody was harvested and subjected to purification.

Total IgG antibody (titer) was determined following Protein A/Protein G chromatography. For bispecific antibodies, total IgG antibody as well as each of the three species of antibody including bispecific (heterdimeric Fc/Fc*), homodimer with wild-type heavy chains (Fc/Fc) and homodimer with modified heavy chains (Fc*/Fc*), was measured in order to determine the ratio of the desired bispecific antibody species. Total titers were determined by an HPLC method utilizing Protein A/Protein G columns using elution techniques as described in U.S. Pat. No. 8,586,713. Briefly, the three bioreactor species bind to columns during sample loading and the bispecific species (Fc/Fc*) elutes first off of the Protein A column employing a pH step gradient in the presence of an ionic modifier. The bispecific species is collected during the first elution step, followed by elution of the two homodimeric species.

Figure 6A:
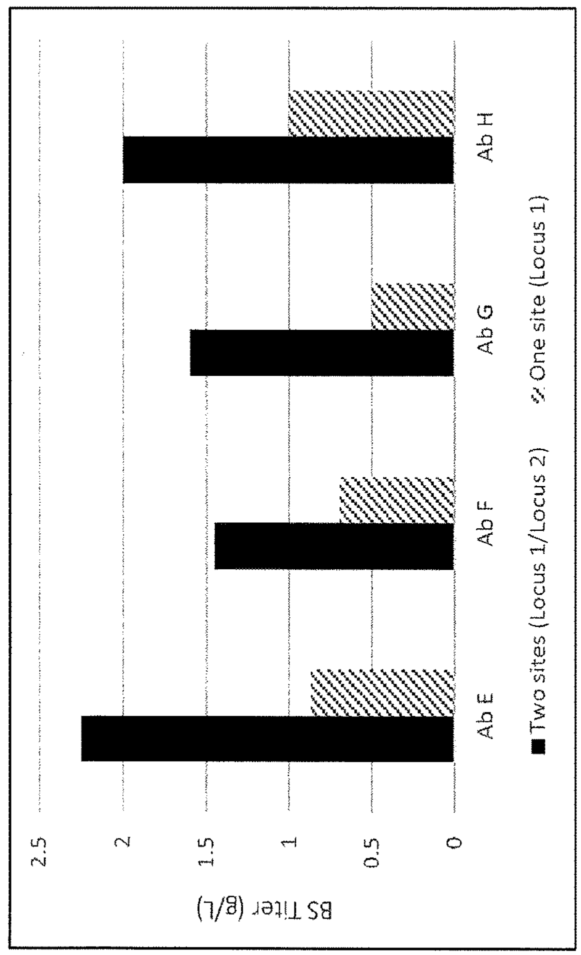
FIGS. 6A and 6B, Bispecific antibody E (Ab E), bispecific antibody F (Ab F), bispecific antibody G (Ab G), and bispecific antibody H (Ab H) were cloned in RSX or $RSX^{2BP}$. Each bispecific antibody-expressing cell comprises a (common) light chain nucleotide, heavy chain nucleotide (wild-type Fc) and modified heavy chain nucleotide (Fc*) in either one expression-enhancing locus (RSX) or two expression-enhancing loci ($RSX^{2BP}$). Cells were isolated and subjected to 13 day fed batch culture in bioreactors, followed by harvest and HPLC elution methods to determine overall antibody and bispecific antibody titers (FIG. 6A). Ratio of bispecific antibody species titer (purified away from the homodimeric species) per total antibody titer was determined as a percentage total Ab (FIG. 6B).

Table 1 shows that the overall (total) IgG titer and bispecific antibody titer (FIG. 6A) in pilot large scale production culture were highly improved by utilizing host cells expressing antibody via two integration sites.

TABLE 1

| Total IgG and Bispecifc IgG Titer Measurement | | | | |
|---|---|---|---|---|
| | Bispecific titer (g/L) | | Total titer (g/L) | |
| Antibody | Two sites (Locus 1/Locus 2) | One site (Locus 1) | Two sites (Locus 1/Locus 2) | One site (Locus 1) |
| Ab E | 2.25 | 0.87 | 4.47 | 2.7 |
| Ab F | 1.45 | 0.7 | 2.9 | 2.4 |
| Ab G | 1.6 | 0.5 | 2.7 | 1.3 |
| Ab H | 2 | 1 | 3.2 | 2.5 |

Figure 6B:
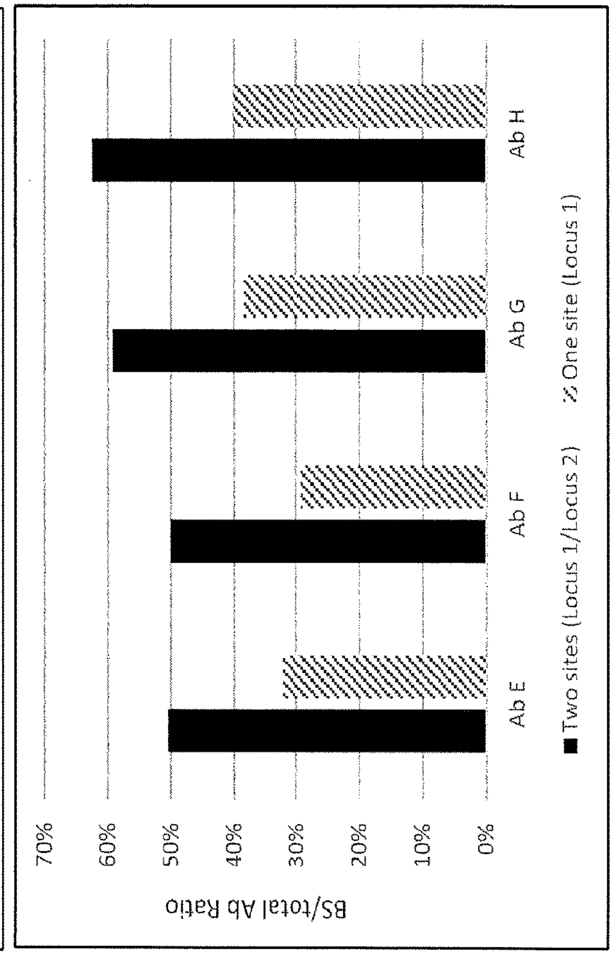

Bispecific titers were determined as described above. As seen in Table 2, the titers of bispecific antibody as a ratio of the total IgG titer produced by the cell is significantly higher in production cultures of host cells having the two integration site construction. See FIG. 6B. In fact, it was unexpected that 50% or greater Bispecific ratios were consistently achieved.

TABLE 2

| Ratio of Bispecific Antibodies per Total IgG Production | | |
|---|---|---|
| | Bispecific Ratio (% total IgG) | |
| | Two sites (Locus 1/Locus 2) | One site (Locus 1) |
| Ab E | 50% | 32% |
| Ab F | 50% | 29% |
| Ab G | 59% | 38% |
| Ab H | 63% | 40% |

Figure 7:
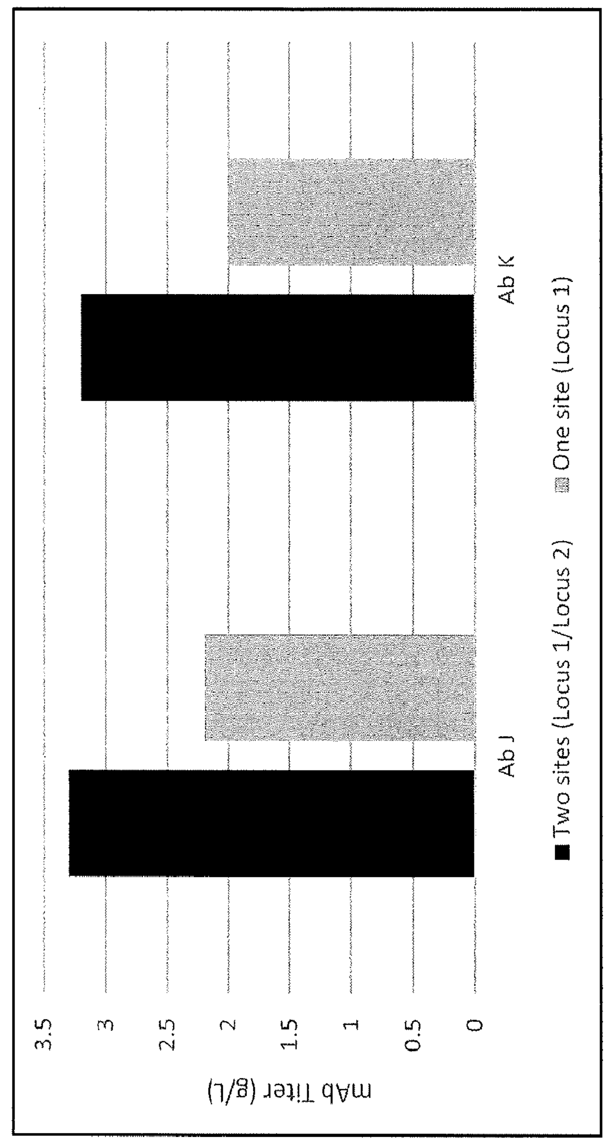
FIG. 7. Monospecifc antibodies J and K (Ab J and Ab K, respectively) were cloned in RSX or $RSX^2$. Cells were isolated and subjected to 13 day fed batch culture in bioreactors, followed by harvest and HPLC methods to determine overall IgG titers.

Monospecific antibodies were expressed using the two integration site method to determine improvements in overall IgG titers. Table 3 illustrates that overall titer in large bioreactor scale was observed to increase significantly from 0.6 to 1.3 fold. See also FIG. 7. For production bioreactors used in manufacturing, especially those at 500 L up to 10,000 L in culture volume, observed increases in titer by use of these improved cell lines equates to a significant amount of increased product yield per batch.

TABLE 3

| Total IgG (Monospecific) Titer Measurement | | |
|---|---|---|
| | Total Titer (g/L) | |
| | Two sites (Locus 1/Locus 2) | One site (Locus 1) |
| Ab J | 3.3 | 2.7 |
| Ab K | 3.2 | 2 |

Although the foregoing invention has been described in some detail by way of illustration and example, it will be readily apparent to those of ordinary skill in the art that certain changes and modifications may be made to the teachings of the invention without departing from the spirit or scope of the appended claims.

SEQUENCES
13515 bases
DNA
*Cricetulus griseus*

SEQ ID NO: 1

```
tctagaaaca aaaccaaaaa tattaagtca ggcttggctt caggtgctgg ggtggagtgc     60
tgacaaaaat acacaaattc ctggctttct aaggcttttt cggggattca ggtattgggt    120
gatggtagaa taaaaatctg aaacataggt gatgtatctg ccatactgca tgggtgtgta    180
tgtgtgtgta tgtgtgtctg tgtgtgtgcc cagacagaaa taccatgaag gaaaaaaaca    240
cttcaaagac aggagagaag agtgacctgg gaaggactcc ccaatgagat gagaactgag    300
cacatgccag aggaggtgag gactgaacca ttcaacacaa gtggtgaata gtcctgcaga    360
cacagagagg gccagaagca ctcagaactc cagggggtca ggagtggttc tctggaggct    420
tctgcccttg gaggttcctg aggaggaggc ttccatattg aaaatgtagt tagtggccgt    480
ttccattagt acagtgacta gagagagctg agggaccact ggactgaggc ctagatgctc    540
agtcagatgg ccatgaaagc ctagacaagc acttccgggt ggaaaggaaa cagcaggtgt    600
gaggggtcag gggcaagtta gtgggagagg tcttccagat gaagtagcag gaacggagac    660
gcactggatg gccccacttg tcaaccagca aaagcttgga tcttgttcta agaggccagg    720
gacatgacaa gggtgatctc ggtttttaaa aggctttgtg ttacctaatc acttctatta    780
gtcagatact ttgtaacaca aatgagtact tggcctgtat tttagaaact tctgggatcc    840
tgaaaaaaca caatgacatt ctggctgcaa cacctggaga ctcccagcca ggccctggac    900
ccgggtccat tcatgcaaat actcagggac agattcttca ctaggtactg atgagctgtc    960
ttggatgcaa atgtggcctc ttcattttac tacaagtcac catgagtcag gaggtgctgt   1020
```

-continued

```
ttgcacagtg tgactaagtg atggagtgtt gactgcagcc attcccggcc ccagcttgtg   1080
agagagatcc ttttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtccccaccg ctgtcccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt ctcagatgac   1440
atgtgacaca gaaggtgttc cctctggaga catgtgatgt ccctgtcatt agtggaatca   1500
gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catacgcata ttacacccca aacgtatcac   1800
ctatacatac cacacataca cacccctcca cacatcacac acataccaca cccacacaca   1860
gcacacacat acataggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacattt gtgtatgcac acatgcacac accaatcaca tgggaagact caggttcttc   2160
actaaggttc acatgaactt agcagttcct ggttatctcg tgaaacttgg aagattgctg   2220
tggagaagag gaagcgttgg cttgagccct ggcagcaatt aaccccgccc agaagaagta   2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctattttgtt atatctttat taaatattct tttagtttta   2460
tgtgcgtgaa taccttgctt gcataaatgt atgggcactg tatgtgttct tggtgccggt   2520
ggaggccagg agagggcatg gatcctccgg agctggcgtt tgagacagtt gtgacccaca   2580
gtgtggggtc tgggaactgg gtcttagtgt tccgcaagtg cagctggggc tcttaacctc   2640
tgagccatcc ctccagcttc aagaaactta ttttcttagg acatggggga agggatccag   2700
ggctttaggc ttgtttgttc agcaaatact cttttcgtgt attttgaatt ttattttatt   2760
ttactttttt gggatagaat cacattctgc agctgaggct gggcctgaac tcatcaaaat   2820
cctcctgtct cagtctacca ggtgataaga ttactgatgt gagcctggct ttgacaagca   2880
ctttagagtc cccagccctt ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttattttttta attaaaaatg   3060
attagctaca tgtcacctgt atgcgtctgt atcatctata tatccttcct tccttctctc   3120
tctttctctc ttcttcttct cacccccaag catctatttt caaatccttg tgccgaggag   3180
atgccaagag tctcgttggg ggagatggtg agggggcgat acaggggaag agcaggagga   3240
aagggggaca gactggtgtg ggtctttgga gagctcagga gaatagcagc gatcttccct   3300
gtccctggtg tcacctctta cagccaacac cattttgtgg cctggcagaa gagttgtcaa   3360
gctggtcgca ggtctgccac acaaccccaa tctggcccca agaaaaggca cctgtgtgtg   3420
actctggggt taaaggcgct gcctggtcgt ctccagctgg acttgaaact cccgtttaat   3480
```

-continued

```
aaagagttct gcaaaataat acccgcagag tcacagtgcc aggttcccgt gctttcctga   3540
agcgccaggc acgggttccc taggaaatgg ggccttgctt gccaagctcc cacggcttgc   3600
cctgcaaacg gcctgaatga tctggcactc tgcgttgcca ctgggatgaa atggaaaaaa   3660
gaaaaagaag aagtgtctct ggaagcgggc gcgctcacac aaacccgcaa cgattgtgta   3720
aacactctcc attgagaatc tggagtgcgg ttgccctcta ctggggagct gaagacagct   3780
agtgggggcg gggggaggac cgtgctagca tccttccacg gtgctcgctg gctgtggtgc   3840
atgccgggaa ccgaaacgcg gaactaaagt caagtcttgc tttggtggaa ctgacaatca   3900
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcat tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggcc   4920
ctgcaacagg aagggaggga ggaagggggg gaacgagaga gaggaaagag agacagaagc   4980
taagataggg aatgagagag gaaggaagaa acgggaagaa attcagactc cttcctgagt   5040
tccgccaacg cctagtgaca tcctgtgcac accctaaggt ggcctttgtg tggcactggc   5100
ttgggtggtc gggaaaggca ttttcagctt gttgcagaac tgccacagta gcatgctggg   5160
tccgtgaaag tttctgcccg ttaacaagaa gtctctacta cttgtgacct caccagtgaa   5220
aatttcttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg gggtgtcaaa aggaaaagaa gggaaacagg cacttgggaa aatgtactcc   5400
cgcccacccg aattttggct tggcaaccgt ggtggaggag caagaaacac gtggacgttt   5460
gaggaggcat ggggtactag gaggacagga agcagaagga gagagctggg ctgacagcct   5520
gcaggcattg cacagtttca gaaggagatt acagcatgac tgagttttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag ggccaccaca   5820
tccccagaaa gagtggagct gctaaaaaag catttgtgat aggcacagtt atattgaatg   5880
```

-continued

```
catggagcag agattacgga aaaatcgaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata attttcatgt tggagtttat ttgtgctaaa aggcagaaaa   6120
gggtaaaaag cacatattaa gagttatgag gttctacgaa taaaaataat gttacttaca   6180
gctattcctt aattagtacc cccttccacc tgtggtaatt tcctgagata gtcagtgggg   6240
aaaagatctc tccttctctt ctttctcccc ctcccctcct ctccctccct ccctccctcc   6300
ctccctcctc tccctccctc cccctttcct tctttctttg ctccttctcc tctgcctcct   6360
tctccctttc ttcttcattt attctaagta gcttttaaca gcacaccaat tacctgtgta   6420
taacgggaaa acacaggctc aagcagatta gagaagattg atctgtgttc actagcgtgc   6480
aattcagagg tgggtgaaga taaaaggcaa acatttgagg ccatttcctt atttggcacg   6540
gcacttagga agtggaacat gcctaatcta ctggtttgta ccacctttcc ctataatgga   6600
ctgtttggga agctcctggg caaccgattc tggcatctca ttggtcagag gcctgttaaa   6660
tggtactctt atttgcaaag aaggctgtaa cttgtagctt taaaagcctc tcctcaagaa   6720
agaagggaga aaggatatgg ctagacatat ctaatagact taaccactgt gaaaagcctt   6780
agtatgaatc agatagaacc tatttttaac tcagttttga aaaaaataat ctttatattt   6840
atttgtgtgt gtgtgtgtgt gtgtgtgtgt gtgtgtgtgt gtgtgtgtgt gaaccacatg   6900
tagcaggtgc tggaggaggc cagaagaggg caccagatct cctggaactg acaccacaca   6960
tggttatgag ctgcctgatg tgggtgctgg gaactgaact ctcgtgttct gcaagagcag   7020
caactgttct cttaactgat gagccatctc tccagccccc cccataattt taattgttca   7080
ttttagtaaa ttttattcat aatcaattat cacagtataa aacaatgatt ttatatatat   7140
catatacata tcaaggatga cagtgagggg gatatgtgtg tgtgtgtgtg tgtgtgtgtg   7200
tgtgtgtgtg tgtgttattt gtgtgtgtgc tttttaagaa ggtgccatag tcactgcatt   7260
tctctgaagg atttcaaagg aatgagacat gtctgtctgc caggaaccct atcttcctct   7320
ttgggaatct gacccaaatg aggtattctg aggaactgaa tgaagagctc aagtagcagt   7380
gtcttaaacc caaatgtgct gtctagagaa agtcaacgtc atcagtgagc tgaggagaga   7440
tttactgagc ggaagacaag cgctctttga tttaagtggc tcgaacagtc acggctgtgg   7500
agtggagcct gtgctcaggt ctgaggcagt ctttgctagc cagctgtgat gagcagtgaa   7560
gaaagggtgg agatggaggc agggtgggag cagggctatg gttcagacta ggtatcgtga   7620
gcacaccagc tggttgactt gtggtctgtg ggtcaggcgt tgtaaacgcc ctcagggtca   7680
ggcagtcaca ttgcttgaag ctgaatgggt gaggcaacac agagagtgca aagaaggcaa   7740
agtaccacct cttccccgac ccaggtcact tctgggttat agctgagact ccggacagca   7800
tgcaaccagc tggttagagc ttcagggaaa acttgatgtc tgcatgttgc tatgaaatgt   7860
gattcggtac atctggagaa aatttataat gctggctcag tcaagcactg aacaaaggta   7920
ccttggcttt gggagctaca tgacattgac ttgtaggcag actttttttt ttctgcccgc   7980
caattcccag ataaccaata tggaggctca atattaatta taaatgctcg gctgatagct   8040
caggcttgtt actagctaac tcttccaact taaatgaacc catttctatt atctacattc   8100
tgccacgtga ctttaccttg tacttcctgt ttcctctcct tgtctgactc tgcccttctg   8160
cttcccagag tccttagtct ggttctcctg cctaacctta tcctgcccag ctgctgacca   8220
agcatttata attdatatta agtctcccag tgagactctc atccagggag gacttgggtg   8280
ctccccccctc ctcattgcca tccgtgtctt cctcttccct cgcttccccc tcctcttcct   8340
```

-continued

```
gctcttcctc ctccacccct cctttcatag tattgatggc aagggtgttc tagaatggag   8400
gagtgcccat aggcatgcaa agaaaccagt taggatgctc tgtgaggggt tgtaatcata   8460
agcgatggac acaattcaag ccacagagtg aagacggaag gatgcactgt gctctagagc   8520
aacttctggg gcagaatcac agggtgagtt tctgacttga gggcgaagag gccacgagga   8580
agggagtgag tttgtctgag ctagaagcta cggcccacct cttggtagca gacctgccca   8640
caagcatgct ttgttaatca tgtgggatct gattttcctc taaatctatg ttcaactctt   8700
aagaaaatgt gaattctcac attaaaattt agatatacgt cttttggtgg ggggggtgta   8760
aaaaatcctc aagaatatgg atttctgggg gccggagaga tggctcagag gttaagagaa   8820
ctggttgctc ttctagacat tctgagttca attcccagca accacatggt ggctcacaac   8880
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaaccaaa aaaaaaaaaa adaaaaadaa aaaaaaaaga gtatggattc   9180
taagaaagcc gtaacagctg gagctgtgta cggagttcag cgtggtacta gaagaacaga   9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaaggggg gatttttaat taggaaaacg atttcctgta  10080
tcacttgtga aactggaggt tgatttgggg cataggacaa tagatttgat gctttgcaaa  10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg gggggcaggg gcggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
```

-continued

```
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga catggtgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta ttttattttt attattgtaa attatgtatg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttccttc ccaaaatgcc aagtgtacaa ggtgagggaa tcacccttgg attcagagcc  12120
cagggtcgtc ctccttaacc tggacttgtc tttctccggc agcctctgac acccctcccc  12180
ccatttctc tatcagaagg tctgagcaga gttggggcac gctcatgtcc tgatacactc  12240
cttgtcttcc tgaagatcta acttctgacc cagaaagatg gctaaggtgg tgaagtgttt  12300
gacatgaaga cttggtctta agaactggag caggggaaaa aagtcggatg tggcagcatg  12360
tacccgaaat cccagaactg gggaggtaga gacggatgag tgcccggggc tagctggctg  12420
ctcagccagc ctagctgaat tgccaaattc caactcctat tgaaaaacct ttaccaaaca  12480
aacaaacaaa caaataataa caacaacaac aacaacaaac taccccatac aaggtgggcg  12540
gctcttggct cttgaggaat gactcaccca aacccaaagc ttgccacagc tgttctctgg  12600
cctaaatggg gtgggggtgg ggcagagaca gagacagaga gagacatgac ttcctgggct  12660
gggctgtgtg ctctaggcca ccaggaactt tcctgtcttg ctctctgtct ggcacagcca  12720
gagcaccagc acccagcagg tgcacacacc tccctccgtg cttcttgagc aaacacaggt  12780
gccttggtct gtctattgaa ccggagtaag ttcttgcaga tgtatgcatg gaaacaacat  12840
tgtcctggtt ttatttctac tgttgtgata aaaaccgggg aactccagga agcagctgag  12900
gcagaggcaa atgcaaggaa tgctgcctcc tagcttgctc cccatggctt gccgggcctg  12960
ctttctgcaa gcccttctct ccccattggc atgcctgaca tgaacagcgt ttgaaatgct  13020
ctcaaatgtc actttcaaag aaggcttctc tgatcttgct aactaaatca gaccatgttt  13080
caccgtgcat tatctttctg ctgtctgtct gtctgtctgt ctgtctatct gtctatcatc  13140
tatcaatcat ctatctatct atcttctatt tatctaccta tcattcaatc atctatcttc  13200
```

-continued

```
taactagtta tcatttattt atttgtttac ttactttttt tatttgagac agtatttctc  13260

tgagtgacag ccttggctgt cctggaaccc attctgtaac caggctgtcc tcaaactcac  13320

agagatccaa ctgcctctgc ctctctggtg ctggggttaa agacgtgcac caccaacgcc  13380

ccgctctatc atctatttat gtacttatta ttcagtcatt atctatcctc taactatcca  13440

tcatctgtct atccatcatc tatctatcta tctatctatc tatctatcta tctatcatcc  13500

atctataatc aattg                                                   13515
```

14931 bases
DNA
*Cricetulus griseus*
misc_feature (2176) . . . (2239)
n is a, c, g, t or nucleotide is missing

SEQ ID NO: 2

```
catgtacact tatgcaagta tgatatggcc caacacagta ttttacacca atttttatct     60

ataaaatata catgtacatc aaaatatatt attaataata acatcattat tctttctttc    120

caagtaataa acacatacac tgaaattttg gttcttgtgg ataattttaa tgaaacagga    180

aatgcaaatt tatcttagca tgtttacttc actttctttg catagataac cagtaatcac    240

attgatggat catgtagtga aatgtatttt taggtatcta aggaattttg gcttcgtttt    300

gtgcttgttg acactgaatt ctattcctaa caacagtgtg taaggattct gtctgatttc    360

ttttaccagt atttgtccat ttgcattttc tttattattc atggctgctg ttctagaaag    420

tggaaggtag tgtgtcaagt ctgtttaaca tgtttccctg atgatcagtg tcttaacacc    480

tctctgagta catgttggcc aatgtcgttt ctagacccat ctattcttgc ttgacttatc    540

ctggtacatg cctgccaaga aatttctcct catcctttct gtctcttcac tgatttactt    600

gatgtgtgga tttcacattg atcatatgga aatagaagat acaattttct ttattcacag    660

tttggaagac tttcaatctc atagatcatc attatttttt gctactgttc cctatgctat    720

ggtgaaattt ccatttgaat aattgcttaa acaattaaca agaaagaatc tatttttact    780

tgcaataact tccatttcag aacatttact acactgttac tatatccaaa aactagtttt    840

atatatcatg tgagaaatga ctaattcata atttggccat gacatttttt tcagaaacag    900

aaaaagtgac caatacatac acaatgctat aaatattaag acttcagcaa attaaatatt    960

tattcatgat atcacataaa attcatttat tatgttttat ttaaatgtgt ttttaaaaca   1020

gtggtatcac taaatattaa gttagatgtg tttatgtgct taatgaattt atattttaga   1080

atgttataag ttgtatatag tcaaatatgt aataaatttt attttttagg tctttctcat   1140

taaggtattt taattttggg tcccttttcc agagtgactc tagctcatga tgagttgaca   1200

taaaaactaa acagtacaaa atgtacattg cattcagtat tgcacttgat ctttgcactg   1260

aagtttgagt cagttcatac atttagtact tgggaagtac attaagctaa ctttcattgc   1320

tctggcaaaa tgctcgataa gataagagtc tattgtggaa agccatggca gcaggaaagt   1380

aagactgctg atgatgttta atccatagtc aagacgcaga aggagatgaa tgctggtatc   1440

caacattttt tgctgttcat ttctctagaa accctagtcc ataaagatgt atgacttgca   1500

ttcaaaatgc gtccccttca gttgttcaac ttttctgtaa atatcctttc aggcatgtct   1560

agaagattgt ttcgcaaata cttctcaatc cattcaagtt gatagtgcag attaatcact   1620

gcagaataaa agcctgtaac ttggctcacg tgccaaggaa tatgcacact cctgacacat   1680

caataagtaa atcaaagtgt agcttttgcc tttaacattg ccagacttat gtaatgttct   1740

gcacgttctt cctccatcac tttttattct aatggtgttt ccttgacatt gaatcacgct   1800

gtggaagctg cttagaatta acattgaaat ctactgatat atttatgatg cagcaattta   1860
```

-continued

```
gatttactat tttacttaga atttttata attgagagaa tataatattt tcacagttat   1920
ctatctgctg taaatagagg attttaaaaa aaatctctat aactttttt tacaacacac   1980
agtaaaatta agttaaaatt taataaagtc actatgttga tttcaaagtg tgctacgccc   2040
acggtggtca cgcaggtgta gcagaagatg ccactaaggt gggctaaggc cgatgggttg   2100
gggtctgcgc tccctggaga tgagccccag gcggttccct ggcaatcagc tgcgatcatg   2160
atgcccgatg agccannnnn nnnnnnnnnn nnnnnnnnnn nnnnnnnnnn nnnnnnnnnn   2220
nnnnnnnnnn nnnnnnnnnc tgggtgactt tatggaaaga atttgataga tttcatgatg   2280
tagaagaatt ttattaggct tattttacag gagactaaga ccctgggacc taaagatatc   2340
tgggtcctga gaatcaggaa atgggtagag acgtggttga tggtatgaga cagattttag   2400
agaactctta gatcatgggc aatgaccgca atctgatgct tagaatagat catctataaa   2460
caattatgct gttctttttc tttctgttgt atgatctgat gatgtagccc ccttgccaag   2520
ttccctgatc ccccttgcca agttccctga ttgtaacagt atataagcat tgcttgagag   2580
catattcaac tacattgagt gtgtctgtct gtcatttcct cgccgattcc tgatttctcc   2640
ttgagccttt tcccttgttc tccctcggtc ggtggtctcc acgagaggcg gtccgtggca   2700
aaagtgtata aatgttctaa aacatttgaa ctctaaaaca tgcaaaatga aaaattaaaa   2760
taaataaaca tgaaaattaa aatatattag ctgctaaaag ttaaacaata ctatataata   2820
ttttgttatt agaattcaaa atcacattag ttggatttaa tttgaacatt gcattctttc   2880
aataataatt tcaataaaaa aagtttcccc atgatagtag aaaataataa catatgtatc   2940
tatctattta tttaactaca catatatagc atttgtttca actaaaataa atgaatgagc   3000
aaagcaccta agtaattggt gtctattata tttatgaagc caatagtttc aaataaatta   3060
tcatgcataa ggaggtattg caaatgttaa accttttttg aaacagatat tcccagttac   3120
agaaattata atttctaatc tttcctataa gtagaatgat gataattaat ataggccatt   3180
tgtaaataat gttcagatta aaatattctc tatttcacta gagaagaatg atattaaatg   3240
tattatattt tatttcccat tttgtttgca ccactattct atatccctca gcagtttaaa   3300
tttgtttcac catatgtgtg tgtgtttgta tcttaaatat ggcactaaaa ttagaataat   3360
ttaatataaa tctttaggag aaaagatatt gaattatttt atgttgatag gaaaatatct   3420
tttaattgtc caagaatact ttttcttcta ttttaggact gatcagaccc aggactaata   3480
ttttatatgt actaattcta tgtaccaaaa tatgttatta tctcatgaat tctgtctcaa   3540
tattgaggta ataaaaatag tccatcatga actttaaaat taaaataatg attaattaat   3600
ttttattcat attttgtttg tatgaatggt tatacatcac atgtgtgcct ggtgactgtg   3660
aatgtcagga gaaggtatga aagccactgg aattggaata agagataata tttgagatgt   3720
tatgtgggtg ctgagaatta gacgcaagcc atcttcaaga atagccagca tactatacca   3780
ctgagtaatc cattcatccc tcaataatta tctttgtaga cagtaaatat atttctaaac   3840
tataaatgac cagaaaaatt aatgtattat taatgaagac attcatctca tgtgacacac   3900
ttcacctgtc taaatcagta acactctctc cactaattaa gattttctaa gtgcatgaca   3960
cttactattt ctaaagctgt ccaatggggg ccagtcccca gtcagcaccc agtgagataa   4020
tccatgaatg catttatatc ttaggaaaaa ttcttatcta tgtagtattt agaacatttt   4080
catgtgaggg gataaacaag gaagcacaga tgctttctga tagaaacttt ctctttaatt   4140
catctagaaa aaaaaaacct ctcaggaaaa tctctcttgc tctcctccca atgctctatt   4200
cagcatcttc tacctactta attctagatc tttttctcta tgcctccttg ctgctgccct   4260
gctggctctg ctctatgcct ccccatgtca cttttctttg ctatctcacc gttaccttct   4320
```

-continued

```
ctgcctcact ctctgccttc ttctctgctt ctcacatggc caggctctgg acaattatag   4380
ttatatgtta cattctcata acacatgata tgtcacatag tttctctcag gctagggata   4440
tcacaatgac tggccaatga gcaagtggcc ttgcatgtag ctctaagttg gtgatggttc   4500
ccagacagta agtagccatt tggttgaaat ttgaggttgg gtagtacatg aagactgaat   4560
tttcttcaaa ctatggcctt gaaatagtaa aacaacacct atgaaaatga cgacctgtat   4620
ttgtctttag aggcaaccac atattgtctg cagggcctgc tttgaatttg ctctgaagtt   4680
agcttgtttg tgtaaaagga agaatcctat atcagcctga gaaatgtaaa atatcctagc   4740
atttcaagtc atcaaaatta tatggagagt ataaatcatc cttctgacta ttcatagtca   4800
tatttgtgtc caccaagtat aaaacacact accaaagggc tgtggaaaaa atcgccataa   4860
ctgttcttat tagggaggca tagcagtggt acctgaggaa gttacagcaa caaccagtca   4920
tccagtcaat aaccccatgg ctttgccact tggaggtacc caataatgtt tggctttgcc   4980
gagtaggact ccaacaaatt cagagggtca atttttaaat gctggttgtc actgctgaac   5040
agtcccattg ccctctgcat aattccacaa tggaaagctt tttacactga ttgccaatca   5100
ttaaacagcc tactcagcat aaacaggtat gatattattc tgcattttgt tacattacta   5160
gatgaattcc tatttcttcc tacaatagtg gaactgaaaa aagatacaca atcatactac   5220
ccctctacta atcttatgac ttatatcatt tcaattttca gaccataatg caaactattg   5280
accaaaacat gtgaagatga aaaatagaaa tgtagaataa tattacatat aaaaagaaaa   5340
ggcggactta ttttgtttta tttcttagca tgcatagcaa tacatgattt gaggtttata   5400
taataaaggg acaataaatc ttcaagaaac ttacccctac tgaattaaaa tattaaagaa   5460
ggtcacacat ttactcaaat atattagact actgggcaaa tagacatgaa aagtagagtt   5520
aatattgagg taggccttct gtgaaatgtc taaggaaatt atgtttcata cagtgtgtaa   5580
ccaagtggga atcatatcag aaagcagtca aaagcttata ttacaagtaa cagatgcttg   5640
gttatatgac ctcccagagc ttgactgtct atacacaaaa agtggtgtta ataaaactgt   5700
aatttgggct atgttttttt aaatggcttc accaacatga aaggaaggga atgagcatgt   5760
catggatgct tagagattat gcttccagca agaagaattg agctttggct cttattacag   5820
aaacatgaca aggtgtgagt tttatttatt agaaattata taatatttta agctggggac   5880
taaaaatttt attgaaacaa acaggcaagg gataggcatg tactagaagc aaaaatagga   5940
tgtcaatgct gtaatgttat tttttggacc aaaatagtat ttcctataga aatgacaatg   6000
atcttaggtt attattcttc ataaagatga caagttcaca agatatccta gttcattaaa   6060
atcgttttag tcatttaata gagtgctgtg atagattaca caaaggaaag cacttacgat   6120
gagaaataat gatatccaca attattttct taattcttag aaacattcta ttgttatatc   6180
tcaatctcag aagccactta ttgctttatt attgaaacat atgaaattgt aagttatata   6240
ttgtctatgg tgacatttca aagaacatgt gacgtacagt gtagcacaga taaagaacat   6300
aactgcagct gaatcagtaa ctaaacttac atacattaaa tctgccatgt tggcaacagt   6360
gtgtgcacta ccaaaggatg tactaatgct cacgacactc ccctatgtca ccctttgttc   6420
atcattacat cataggtcta ttttgtttgc ttttgaaatc tagaccaagt cttttgtgtc   6480
tttccaagca cagagctcat taatttacct catagacttg ttaaacttct tctggttcat   6540
caattgaata gaaatactca ctactaatta tgtgagaccc tgccagtacc atagcacatg   6600
gataattttt acataaaaca tgcatacaag taagattatt cagactgaac atgaatttta   6660
gagaaatcag gaaggagtat atgggagtgg ttggagtgag actagagaaa tgtaattaaa   6720
```

-continued

```
ctataatctc aatacaaaga tctactaagc aaaaaacatg aaacattgtc attcaagtga   6780

aacatcagtc ttcaaattgg aaagatattt ttactaggaa aatgtctggt agatggttat   6840

tatctagaaa acacaaaaat tagaaaacgg taaactttaa taaaaagaat aatacaatga   6900

gactacatga aaagttctta actaatgaaa caaatatctt gaaacttttt tcttaaaagt   6960

ttaatatcaa taaccatcat ggaaattcaa attaaaacta tttacatatt acccctgaaa   7020

taataactaa tacccaataa aaataatata aacaaaaaat ggcaatgcat gccatcatgg   7080

atttgggaga gagaatgttc attgcagttc tgaatggata ctggtgccac cacggtgaaa   7140

atctctgtat aggtccttcc aaaagctgaa aatagacata tcacaagacc tgccacacat   7200

ttttcaagca aatacccaaa ggactctacc tgactgcaga gacactttct cataaaatat   7260

tattgttgat ctattcataa tatctggaaa atagaaacag ccaagatgcc catcaactga   7320

ttaatagatg ataaaattat tgtacatttc agtgtaatat tattcagttt ttaagaaaaa   7380

tgaaattatg taataagcat gtaaatggat atatcttgaa acaaccattc cccattatat   7440

tacctaaaca ttgaaagtcc aaaatcatat gatcttttta gtggatctac taatcttttg   7500

ctatatgtat tttattgaac tacccatgga tgtgagataa ttggtaacaa cagcacatgg   7560

gagagcatgg gatcattcaa ggaagattag agagaatgca ttttttagga gataatggag   7620

gagcaataga aaggattaaa tgaggttact gatgaaagtg atggttagag aaggcaatat   7680

gaggagggat aactagcact tagggccttt tgaaaaagac atagagaaaa tactattgta   7740

gaaacttcct ataattggtg tatagttata tacaccaaag agctcagatg gagttaccct   7800

ataatggaaa tattaactac tttttatcac tgtgataaaa catcctgaac agagcaacat   7860

agattgggaa gcatttactt tggcttacag ttctaacggg ataaaaattc atgatgaaag   7920

aatgaatatg tcagcaaaca gcagtagcaa tggcctgaga agcaggtgag agctcacatc   7980

ttgaagtgta agaatgtagc agagagaaca aactgcaaat gaccagaaaa tgcttttgga   8040

tcagagccca tacccctctg actgacttct ccagaaattc tgaacaaata aaactcccca   8100

aacagagcca taactgaagg tccagtgtct gagactacta ggggtatttc ttattcaaac   8160

cactacaatg gggtgggggg agcaatcctc caagtaggca ctacacacag acaaataaaa   8220

actctagtaa ctggaatgga ttgacttatt tgaattactt gccagtggag ctacatagag   8280

cacaattatt gtatttaaat taccctttat gatcttacaa aacttgacag taagatcata   8340

ttgctaaaga aaccacatat ttgaatcagg gaacatggtg atatctagtt gttcttcaac   8400

tggaaacttc atgctttctg cccagcattc atgttgctgg aaagagcaat gtacactacc   8460

agtgtagaaa ttaaatcatc aatcttatca agatgtggat cctataagtt acaataaaaa   8520

ttagcctgat aagatatccc caccagaaga atattcacat aaatgctatg ggagcaacaa   8580

gctattttct aaattagctt taatcctatt ctacaagaga gaatccatat ctagaatagt   8640

tatagggatc aagaacccat ggcttgattg gtcataggcc caatgggaga tcctaatatt   8700

attgttctac aaaatgaaaa taactcctaa tgacttgttg ctgcagtaat aagttagtat   8760

gttgctcaac tatcacaaga gaagttttgt cttacaataa atggcaatta aagcagcccc   8820

acaagattta tatcataccg atctcctcat ggcctatgca tctagaagct aggaaacaaa   8880

gaggacccta agagagacat acatggtccc cctggagaag gggaaggggg caagacctcc   8940

aaagctaatt gggagcatgg gggaggggag agggagttag aagaaagaga aggggataaa   9000

aggagggaga ggaggacaag agagagaagg aagatctagt caagagaaga tagaggagag   9060

caagaaaaga gataccatag tagagggagc cttgtatgtt taaatagaaa actggcacta   9120

gggaattgtc caaagatcca caaggtccaa ctaataatct aagcaatagt cgagaggcta   9180
```

-continued

```
ccttaaaagc ctttctctga taatgagatt gatgactacc ttatatacca tcctagagcc   9240
ttcatccagt agctgatgga agcagaagca gacatctaca gctaaacact gagctagttg   9300
cagacaggga ggagtgatga gcaaagtcaa gaccaggctg gagaaacaca cagaaacagc   9360
agacctgaaa aaaatgttgc acatggaccc cagactgata gctgggagtc cagcatagga   9420
cttttctaga aaccctgaat gaggatatca gtttggaggt ctggttaatc tatggggaca   9480
ctggtagtgg atcaatattt atccctagtt catgactgga atttgggtac ccattccaca   9540
tggaggaatt ctctgtcagc ctagacacat gggggaggtt ctaggtcctg ctccaaataa   9600
tgtgttagac tttgaagaac tcccttgaga agactcaccc tccctgggga gcagaaaggg   9660
gatgggatga gggttggtga gggacaggag aggaggggag ggtgagggaa ctgggattga   9720
caagtaaatg atgcttgttt ctaatttaaa tgaataaagg aaaagtaaaa gaagaaaaga   9780
aaacaggcca aaagattata aaagacagag gtggtgggtg actataaaga aacactatta   9840
tctaaataaa aatatgtcag aagcacacat gaacttatag tgtttatgaa agtatgtata   9900
ataactacat aatctcaagc caagaaaaaa atatcatctt tcagtgatga aggtgatttt   9960
atttctccca gaattaaagc caaagaccta atgaaagtaa ttatcttcaa aaggttgaaa  10020
atacatactt tgcaatacac agatctgcct agaaatctca tgttcacaat acacatgatg  10080
ctcaattgaa ttccattcaa tgttacagtt tagataaaca gtttgtagat aaactcacaa  10140
tgtatcattt ctttttattt tttgaccaaa cagcttctca tctgttattc agaataattc  10200
ctcgatggca ggatatccat cccaattggg ggaaggggag aatttgaaga aaacctagac  10260
cacatacata tttgccattg ggaaacaaag tctaaaatga tgttgttcat atcttctcta  10320
ctagtcctct ccccgtccca aagaaccttg gtatatgtgc ctcattttac agagagagga  10380
aagcaggaac tgagcatccc ttacttgcca tcctcaaccc aaaatttgca tcattgctca  10440
gctctgccct tctcatatga cagttacaag tcaaggcttc caaagtccct ctgtcatgtt  10500
tggtgtcaat agtttataca gatgacttca tgtcttcata tctaatgtct tatatagatt  10560
aatattaaac aatgttattt ctctaaccac attttaaatt aatttaaaaa tctattaatt  10620
gtgtatataa aatgcagaca gagtgctgag acacaatata agcctgatga tctgaatttg  10680
aaactcacac ccaccacatg gagaatcaac ttccaaaaat tttcctatta cttccacact  10740
tacaccattg tacaaacaca ataataatga acaaaatgaa atgaaataaa aaattaagtc  10800
tctgtaggta atgctactgt gcagcaaaag taaaaatggc agcttaagct tgctttatgg  10860
ttacacttta ccatcttcca ttaattataa ggacttcaat catggcagaa ctatgctgtt  10920
attgtctcag tgtaacctaa ccaggtgttc cagatgttct taatgtggac acctaaacta  10980
tttgatattt gggttaagat ctttccctct ttcagaagaa acctcaggac agagggaatc  11040
ttgtctttta attttgagtc tgtagacttt ttccatttca aatatacatg aaacaagtga  11100
tgaagaaaat taatcaaaag gtgggaattg caatgatatt aggttcaata ttaagcttca  11160
atattatcat ggaatcgcct gttatacact gagtgtttgg caataaggga tttttagaag  11220
aaggagtttt tattctcaac aggttcctta agtttagctc aaataaatct aagcaatcca  11280
ctctagaatt aaatagtttc ctaagggcac agctatgaat agagctcaat ttacatataa  11340
aattttgttc accatttatg tcattccagt tttcattagt acaaggaaaa tacaaaatat  11400
ttagatgtca atatcaagtg aatagttcat ctcctttttt aatatatatc acctaaatca  11460
ccattttctc agaaaaatct ggcctgaagt tctgtctgga acttcaacat gaaaaatatg  11520
cacagcttgc tattataaat cctagttgat ttttaagatt catgtctggt gtctgactca  11580
```

-continued

```
gaggggccag aggctagaca aatatttttt gaatcttcat tgtgaagatt tttaatgatt 11640
attttaatat aaataacaaa gatgatggat aatgtaactt tgtacagttc atagacgctg 11700
aactactttg tgcttaaaat gttagttccc tatcataaat gataggtgat aagtgtatgt 11760
ttaatacttt ccctctgagc tatattcatg tactagagaa ttattttaaa catgaaaaga 11820
ctgtgtttat agtctcagct cctgagaact ggtccaacct taggcaggtg aatgccagga 11880
gcaacgtttt tcttctacag aggatgcttt gctgccaagc aacctggttg tgtggaaatg 11940
ttcctttttt aatcaagttt aaagggtctt catcatgctg ttgctccaca tattttcagg 12000
ttagagcttg gtccttggag tattatcttt taccagaaaa ttcatagtat tctttcaata 12060
actaacaact aaacttttcg ataaaaaaga attggaattt caattttaaa gcctgagtaa 12120
aattcttgtg aatcaggata ttttatttta agtcttatct tttaaaaagt tattttattt 12180
tttaaaaaat tataatatac tttcataatt tccctccttc acttttcttt acaaacactt 12240
ctatagatca ccatgtgttt ttttttttac atttatggcc tctttctgtt cattgttatt 12300
acatacaaat agtcttgcct atagaagaac accacaattt gttacctgat aacaaattat 12360
caacccttaa aacctacaaa ctattgatat tactgaaaag actatactta tagatgtaaa 12420
gatatatgtg tgtgcacata tatagataca catatatgta ggatttttaa ttttagattt 12480
tagacatcaa aattatttat atgactgaga aactagacac tataaatgag cattcagtat 12540
tcaacaccgt gattttagat attgtcacaa tgacagaaaa ttttcttata gaaaatttta 12600
agttttgtga ttgctctgtg cacttagtga agtctcacag aaaaagaatc atagtatttt 12660
tagtttataa taaaaagtac atataattaa aatggttggc acaaaacaac atttgagcat 12720
ttttcctatt tactatcaag tagtatcatt ttgaaataat aatttgacta gtttcaaaaa 12780
tgaaaacaaa atttaaacta aatgcctaat ctagcctgat aacattttta tgaatgaaat 12840
tattcaatag tgttatcaat taggggccca aaacttttcc taaaataaaa cttttaattt 12900
ttttccattt ttatttaaat tagaaacaaa attgttttac atgtaaatca gagtttcctc 12960
accctcccct tctccctgtc cctcactaac accctacttg tcccatacca tttctgctcc 13020
ccagggaggg tgaggccttc catggggaaa cttcagagtc tgtctatcct ttcggatagg 13080
gcctaggccc tcacccattt gtctaggcta aggctcacaa agtttactcc tatgctagtg 13140
ataagtactg atctactaca agagacacca tagatttcct aggcttcctc actgacaccc 13200
atgttcatgg ggtctggaac aatcatatgc tagtttccta ggtatcagtc tggggaccat 13260
gagctccccc ttgttcaggt caactgtttc tgtgggtttc accaccctgg tcttgactgc 13320
tttgctcatc actcctccct ttctgtaact gggttccagt acaattccgt gtttagctgt 13380
gggtgtctac ttctactttc atcagcttct gggatggagc ctctaggata gcatacaatt 13440
agtcatcatc tcattatcag ggaagggcat ttaaagtagc ctctccattg ttgcttggat 13500
tgttagttgg tgtcatcttt gtagatctct ggacatttcc ctagtgccag atatctcttt 13560
aaacctacaa gactacctct attatggtat ctcttttctt gctctcgtct attcttccag 13620
acaaaatctt cctgctccct tatattttcc tctcccctcc tcttctcccc ttctcattct 13680
cctagatcca tcttcccttc ccccatgctc ccaagagaga tgttgctcag gagatcttgt 13740
tccttaaccc ttttcttggg gatctgtctc tcttagggtt gtccttgttt cctagcttct 13800
ctggaagtgt ggattgtaag ctggtaatca tttgctccat gtctaaaatc catatatgag 13860
tgatgtttgt ctttttgtga ctgggttacc tcactcaaaa tggtttcttc catatgtctg 13920
tggatttcaa tagcacaaac aacatacagt atcttggggc aacactaacc aaacaagtga 13980
aagaccagta tagcaagaac tttgagttta aagaaagaaa ttaaagaaga taccagaaaa 14040
```

-continued

```
tggaaagatc tcccatgctc tttgataggc agaatcaaca tagtaaaaat ggcaatcttg  14100
ccaaaatcca tctacagact caatgcaatc cccattaaat accagcacac ttcttcacag  14160
acctgaaaga ataatactta actttatatg gagaaacaaa agacccagga taggccaaac  14220
aaccctgtac aatgaaggca cttccagagg catccccatc cctgacttca agctctatta  14280
tagagtaata atcctgaaaa cagcttggta atggcacaaa aatagacagg tagaccaatg  14340
gaattgagtt gaaaaccctg atattaaccc acatatctat gaacacctga ctttgacaaa  14400
gaagctaagg ttatacaatg taagaaagaa agcatcttca acaaatcgtg ctggcataac  14460
tggatgctgg catgtagaag actgcagata gatccatgtc taatgccatg cacaaaactt  14520
aagtccaaat ggatcaaaaa cctcaacata aatccagcca cactgaacct catagaagag  14580
aaagtgggaa gtatccttga ataaattggt acaggagacc acatcttgaa cttaacacca  14640
gtagcacaga caatcagatc aataatcaat aaatgggacc tcctgaaact gagaagcttc  14700
tgtaaggcaa tggataagtc aacaggacaa aatggcagcc cacggaatgg gaaaagatat  14760
tcaccaatcc tatatctgac agagggctgc tctctatttg caaagaacac aataagctag  14820
tttttaaaac accaattaat ccgattataa agttgggtag agaactaaat aaagaattgt  14880
taacagagca atctaacttg gcagaaagac acataagaaa gtgctcacca t           14931
```

4001 bases
DNA
*Cricetulus griseus*

SEQ ID NO: 3

```
ccaagatgcc catcaactga ttaatagatg ataaaattat tgtacatttc agtgtaatat     60
tattcagttt ttaagaaaaa tgaaattatg taataagcat gtaaatggat atatcttgaa    120
acaaccattc cccattatat tacctaaaca ttgaaagtcc aaaatcatat gatcttttta    180
gtggatctac taatcttttg ctatatgtat tttattgaac tacccatgga tgtgagataa    240
ttggtaacaa cagcacatgg gagagcatgg gatcattcaa ggaagattag agagaatgca    300
ttttttagga gataatggag gagcaataga aaggattaaa tgaggttact gatgaaagtg    360
atggttagag aaggcaatat gaggagggat aactagcact tagggccttt tgaaaaagac    420
atagagaaaa tactattgta gaaacttcct ataattggtg tatagttata tacaccaaag    480
agctcagatg gagttaccct ataatggaaa tattaactac tttttatcac tgtgataaaa    540
catcctgaac agagcaacat agattgggaa gcatttactt tggcttacag ttctaacggg    600
ataaaaattc atgatgaaag aatgaatatg tcagcaaaca gcagtagcaa tggcctgaga    660
agcaggtgag agctcacatc ttgaagtgta agaatgtagc agagagaaca aactgcaaat    720
gaccagaaaa tgcttttgga tcagagccca taccccctcg actgacttct ccagaaattc    780
tgaacaaata aaactcccca aacagagcca taactgaagg tccagtgtct gagactacta    840
ggggtatttc ttattcaaac cactacaatg gggtgggggg agcaatcctc caagtaggca    900
ctacacacag acaaataaaa actatagtaa ctggaatgga ttgacttatt tgaattactt    960
gccagtggag ctacatagag cacaattatt gtatttaaat taccctttat gatcttacaa   1020
aacttgacag taagatcata ttgctaaaga aaccacatat ttgaatcagg gaacatggtg   1080
atatctagtt gttcttcaac tggaaacttc atgctttctg cccagcattc atgttgctgg   1140
aaagagcaat gtacactacc agtgtagaaa ttaaatcatc aatcttatca agatgtggat   1200
cctataagtt acaataaaaa ttagcctgat aagatatccc caccagaaga atattcacat   1260
aaatgctatg ggagcaacaa gctattttct aaattagctt taatcctatt ctacaagaga   1320
gaatccatat ctagaatagt tatagggatc aagaacccat ggcttgattg gtcataggcc   1380
```

-continued

```
caatgggaga tcctaatatt attgttctac aaaatgaaaa taactcctaa tgacttgttg   1440

ctgcagtaat aagttagtat gttgctcaac tctcacaaga gaagttttgt cttacaataa   1500

atggcaatta aagcagcccc acaagattta tatcataccg atctcctcat ggcctatgca   1560

tctagaagct aggaaacaaa gaggacccta agagagacat acatggtccc cctggagaag   1620

gggaaggggg caagacctcc aaagctaatt gggagcatgg gggaggggag agggagttag   1680

aagaaagaga aggggataaa aggagggaga ggaggacaag agagagaagg aagatctagt   1740

caagagaaga tagaggagag caagaaaaga gataccatag tagagggagc cttgtatgtt   1800

taaatagaaa actggcacta gggaattgtc caaagatcca caaggtccaa ctaataatct   1860

aagcaatagt cgagaggcta ccttaaaagc ctttctctga taatgagatt gatgactacc   1920

ttatatacca tcctagagcc ttcatccagt agctgatgga agcagaagca gacatctaca   1980

gctaaacact gagctagttg cagacaggga ggagtgatga gcaaagtcaa gaccaggctg   2040

gagaaacaca cagaaacagc agacctgaaa aaaatgttgc acatggaccc cagactgata   2100

gctgggagtc cagcatagga cttttctaga aaccctgaat gaggatatca gtttggaggt   2160

ctggttaatc tatggggaca ctggtagtgg atcaatattt atccctagtt catgactgga   2220

atttgggtac ccattccaca tggaggaatt ctctgtcagc ctagacacat gggggaggtt   2280

ctaggtcctg ctccaaataa tgtgttagac tttgaagaac tcccttgaga agactcaccc   2340

tccctgggga gcagaaaggg gatgggatga gggttggtga gggacaggag aggaggggag   2400

ggtgagggaa ctgggattga caagtaaatg atgcttgttt ctaatttaaa tgaataaagg   2460

aaaagtaaaa gaagaaaaga aaacaggcca aaagattata aaagacagag gtggtgggtg   2520

actataaaga aacactatta tctaaataaa aacatgtcag aagcacacat gaacttatag   2580

tgtttatgaa agtatgtata ataactacat aatctcaagc caagaaaaaa atatcatctt   2640

tcagtgatga aggtgatttt atttctccca gaattaaagc caaagaccta atgaaagtaa   2700

ttatcttcaa aaggttgaaa atacatactt tgcaatacac agatctgcct agaaatctca   2760

tgttcacaat acacatgatg ctcaattgaa ttccattcaa tgttacagtt tagataaaca   2820

gtttgtagat aaactcacaa tgtatcattt ctttttattt tttgaccaaa cagcttctca   2880

tctgttattc agaataattc ctcgatggca ggatatccat cccaattggg ggaaggggag   2940

aatttgaaga aaacctagac cacatacata tttgccattg ggaaacaaag tctaaaatga   3000

tgttgttcac atcttctcta ctagtcctct ccccgtccca aagaaccttg gtatatgtgc   3060

ctcattttac agagagagga aagcaggaac tgagcatccc ttacttgcca tcctcaaccc   3120

aaaatttgca tcattgctca gctctgccct tctcatatga cagttacaag tcaaggcttc   3180

caaagtccct ctgtcatgtt tggtgtcaat agtttataca gatgacttca tgtcttcata   3240

tctaatgtct tatatagatt aatattaaac aatgttattt ctctaaccac attttaaatt   3300

aatttadaaa tccattaatt gtgtctataa aatgcagaca gagtgctgag acacaatata   3360

agcctgatga tctgaatttg aaactcacac ccaccacatg gagaatcaac ttccaaaaat   3420

tttcctatta cttccacact tacaccattg tacaaacaca ataataatga acaaaatgaa   3480

atgaaataaa aaattaagtc tctgtaggta atgctactgt gcagcaaaag taaaaatggc   3540

agcttaagct tgctttatgg ttacacttta ccatcttcca ttaattataa ggacttcaat   3600

catggcagaa ctatgctgtt attgtctcag tgtaacctaa ccaggtgttc cagatgttct   3660

taatgtggac acctaaacta tttgatattt gggttaagat ctttccctct ttcagaagaa   3720

acctcaggac agagggaatc ttgtctttta attttgagtc tgtagacttt ttccatttca   3780

aatatacatg aaacaagtga tgaagaaaat taatcaaaag gtgggaattg caatgatatt   3840
```

-continued

```
aggttcaata ttaagcttca atattatcat ggaatcgcct gttatacact gagtgtttgg   3900

caataaggga tttttagaag aaggagtttt tattctcaac aggttcctta agtttagctc   3960

aaataaatct aagcaatcca ctctagaatt aaatagtttc c                       4001
```

What is claimed is:

1. A cell comprising, a first exogenous nucleic acid integrated within a first enhanced expression locus; and a second exogenous nucleic acid integrated within a second enhanced expression locus;

wherein the first and second exogenous nucleic acids together encoding an antigen-binding protein.

2. The cell of claim 1, wherein the first exogenous nucleic acid comprises a nucleotide sequence encoding a first heavy chain fragment (HCF), and the second exogenous nucleic acid comprises a nucleotide sequence encoding a light chain fragment (LCF).

3. The cell of claim 2, wherein the second exogenous nucleic acid further comprises a nucleotide sequence encoding a second HCF.

4. The cell of claim 3, wherein the first exogenous nucleic acid further comprises a nucleotide sequence encoding a second LCF.

5. A cell comprising, integrated within a first enhanced expression locus, from 5' to 3': a first recombinase recognition site (RRS), a first exogenous nucleic acid, and a second RRS;

integrated within a second enhanced expression locus, from 5' to 3': a third RRS, a second exogenous nucleic acid, and a fourth RRS;

wherein the first and second RRS are different, and the third and fourth RRSs are different.

6. The cell of claim 5, wherein the first exogenous nucleic acid comprises a first selectable marker gene, and the second exogenous nucleic acid comprises a second selectable marker gene, wherein the first and the second selectable marker genes are different.

7. The cell of claim 5, where the first exogenous nucleic acid comprises a first selectable marker gene, a first additional RRS, and a first additional selectable marker gene, wherein the first and first additional selectable marker genes are different, and the first additional RRS is different from the first and second RRSs.

8. The cell of claim 5, wherein the second exogenous nucleic acid comprises a second selectable marker gene, a second additional RRS, and a second additional selectable marker gene, wherein the second and second additional selectable marker genes are different from each other and also from the first and first additional selectable marker genes, and wherein the second additional RRS is different from the third and fourth RRSs.

9. The cell of claim 5, wherein the cell is a CHO cell.

10. The cell of claim 9, wherein one of the two enhanced expression loci is selected from the group consisting of a nucleotide sequence at least 90% identical to SEQ ID NO: 1, a nucleotide sequence at least 90% identical to SEQ ID NO: 2, and a nucleotide sequence at least 90% identical to SEQ ID NO:3.

11. A set of vectors for expressing a bispecific antigen-binding protein in a cell, comprising a first vector comprising from 5' to 3', a first RRS, a first nucleic acid comprising a nucleotide sequence encoding a first HCF, and a second RRS;

a second vector comprising from 5' to 3', a third RRS, a second nucleic acid comprising a nucleotide sequence encoding a second HCF, and a fourth RRS; and a nucleotide sequence encoding a first LCF;

wherein the first, second, third, and fourth RRSs are different;

wherein the bispecific antigen-binding protein comprises the first HCF, the second HCF and the first LCF, and wherein the first and second HCFs are different; and wherein either (a) the nucleotide sequence encoding the first LCF is in a third vector and is flanked by a 5' RRS and 3' RRS, wherein (i) the 3' RRS is the same as the first RRS, and the 5' RRS is different from the first and second RRSs, or (ii) the 5' RRS is the same as the second RRS, and the 3' RRS is different from the first and second RRSs; or (b) the set of vectors further comprises a nucleotide sequence encoding a second LCF that is either within the second nucleic acid in the second vector, or is in a fourth vector separate from the first, second and third vectors.

12. The set of vectors of claim 11, wherein the nucleotide sequence encoding the first LCF is within the first nucleic acid in the first vector.

13. The set of vectors of claim 11, wherein in (b) the first and second LCFs are the same.

14. The set of vectors of claim 13, wherein the nucleotide sequence encoding the first LCF is within the first nucleic acid in the first vector, and the nucleotide sequence encoding the second LCF is on the fourth vector.

15. The set of vectors of claim 14, wherein the nucleotide sequence encoding the second LCF on the fourth vector is flanked by a 5' RRS and 3' RRS, wherein (i) the 3' RRS is the same as the third RRS, and the 5' RRS is different from the third and fourth RRSs, or (ii) the 5' RRS is the same as the fourth RRS, and the 3' RRS is different from the third and fourth RRSs.

16. The set of vectors of claim 13, wherein the nucleotide sequence encoding the first LCF is within the first nucleic acid in the first vector, and the nucleotide sequence encoding the second LCF is within the second nucleic acid on the second vector.

17. The set of vectors of claim 13, wherein the nucleotide sequence encoding the first LCF is on the third vector, and the nucleotide sequence encoding the second LCF is on the fourth vector.

18. The set of vectors of claim 17, wherein the nucleotide sequence encoding the first LCF on the third vector is flanked by a 5' RRS and 3' RRS, wherein (i) the 3' RRS on the third vector is the same as the first RRS, and the 5' RRS on the third vector is different from the first and second RRSs, or (ii) the 5' RRS on the third vector is the same as the second RRS, and the 3' RRS on the third vector is different from the first and second RRSs; and wherein the nucleotide sequence encoding the second LCF on the fourth vector is flanked by a 5' RRS and 3' RRS, wherein (i) the 3' RRS on the fourth vector is the same as the third RRS, and the 5' RRS on the fourth vector is different from the third and fourth RRSs, or (ii) the 5' RRS on the fourth vector is the same as the fourth RRS, and the 3' RRS on the fourth vector is different from the third and fourth RRSs.

19. A system comprising a cell and a set of vectors, wherein the cell comprises, integrated within a first enhanced expression locus: from 5' to 3', a first recombinase recognition site (RRS), a first exogenous nucleic acid, and a second RRS;

integrated within a second enhanced expression locus: from 5' to 3', a third RRS, a second exogenous nucleic acid, and a fourth RRS;

wherein the first and second RRSs are different, and the third and fourth RRSs are different; and wherein the first and second enhanced expression loci are different;

wherein the set of vectors comprises, a first vector comprising from 5' to 3', a first vector 5' RRS, a first nucleic acid, and a first vector 3' RRS, wherein the first vector 5' and 3' RRSs are different;

a second vector comprising from 5' to 3', a second vector 5' RRS, a second nucleic acid, and a second vector 3' RRS, wherein the second vector 5' and 3' RRSs are different;

a nucleotide sequence encoding a first heavy chain fragment (HCF) and a nucleotide sequence encoding a first light chain fragment (LCF), wherein one of the nucleotide sequences is in the first nucleic acid and the other nucleotide sequences is in the second nucleic acid; wherein the first HCF and the first LCF are regions of an antigen-binding protein; and wherein upon introduction of the vectors into the cell, the first and second nucleic acids in the vectors integrate into the first enhanced expression locus and the second enhanced expression locus, respectively, through recombination mediated by the RRSs.

20. The system of claim 19, wherein the antigen-binding protein is a monospecific antigen-binding protein.

21. The system of claim 20, wherein the first and third RRSs are the same, and the second and fourth RRSs are the same.

22. The system of claim 20, wherein the antigen-binding protein is a bispecific antigen-binding protein.

23. The system of claim 22, further comprising a nucleotide sequence encoding a second HCF that is different from the first HCF.

24. The system of claim 23, further comprising a nucleotide sequence encoding a second LCF, and wherein optionally the first and second LCFs are the same.

25. The system of claim 19, wherein the cell is a CHO cell.

26. The system of claim 25, wherein the two enhanced expression loci include a locus comprising the nucleotide sequence of SEQ ID NO: 1 and a locus comprising the nucleotide sequence of SEQ ID NO: 2.

27. A method, comprising:

(i) providing the system of claim 19;

(ii) introducing the vectors into the cell by transfection; and (iii) selecting a transfected cell where the nucleic acids in the vectors have integrated into the first and second enhanced expression loci through recombination mediated by the RRSs.

28. The method of claim 27, further comprising;

(iv) expressing and obtaining the antigen-binding protein from the selected transfected cell.

29. A method of making an antigen-binding protein, comprising:

providing the cell of claim 1, and expressing and obtaining the antigen-binding protein from the cell.

30. The cell of claim 3, wherein the first and second HCFs are different.

31. The cell of claim 3, wherein the nucleotide sequence encoding the first HCF encodes a first CH3 domain, and wherein the nucleotide sequence encoding the second HCF encodes a second CH3 domain.

32. The cell of claim 31, wherein the first and second CH3 domains differ in at least one amino acid position.

33. The cell of claim 31, wherein the nucleotide sequences encoding the first and second CH3 domains differ from each other in that one of the nucleotide sequences has been codon modified.

34. The cell of claim 33, wherein the first and second LCFs are the same.

35. The cell of claim 2, wherein each of the nucleotide sequences encoding a HCF or LCF is operably linked to a promoter.

36. The cell of claim 3, wherein each of the nucleotide sequences encoding a HCF or LCF is operably linked to a promoter.

37. The cell of claim 4, wherein each of the nucleotide sequences encoding a HCF or LCF is operably linked to a promoter.

38. The cell of claim 2, wherein the antigen-binding protein is monospecific.

39. The cell of claim 3, wherein the antigen-binding protein is monospecific.

40. The cell of claim 30, wherein the antigen-binding protein is bispecific.

41. The cell of claim 1, wherein one of the two enhanced expression loci is selected from the group consisting of a nucleotide sequence at least 90% identical to SEQ ID NO:

1, a nucleotide sequence at least 90% identical to SEQ ID NO: 2, and a nucleotide sequence at least 90% identical to SEQ ID NO: 3.

42. The cell of claim 1, wherein one of the two enhanced expression loci comprises SEQ ID NO: 1, and the other one of the two enhanced expression loci comprises SEQ ID NO: 2 or SEQ ID NO: 3.

43. The cell of claim 1, wherein the cell is a CHO cell.

* * * * *

UNITED STATES PATENT AND TRADEMARK OFFICE

CERTIFICATE OF CORRECTION

PATENT NO. : 11,512,144 B2
APPLICATION NO. : 16/095084
DATED : November 29, 2022
INVENTOR(S) : Robert Babb It is certified that error appears in the above-identified patent and that said Letters Patent is hereby corrected as shown below:

On the Title Page

(73) Assignee should read:
Regeneron Pharmaceuticals, Inc.,
Tarrytown, NY (US)

Signed and Sealed this
Twenty-third Day of May, 2023

Katherine Kelly Vidal

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 13515
<212> TYPE: DNA
<213> ORGANISM: Cricetulus griseus

<400> SEQUENCE: 1

```
tctagaaaca aaaccaaaaa tattaagtca ggcttggctt caggtgctgg ggtggagtgc     60

tgacaaaaat acacaaattc ctggctttct aaggcttttt cggggattca ggtattgggt    120

gatggtagaa taaaaatctg aaacataggt gatgtatctg ccatactgca tgggtgtgta    180

tgtgtgtgta tgtgtgtctg tgtgtgtgcc cagacagaaa taccatgaag gaaaaaaaca    240

cttcaaagac aggagagaag agtgacctgg gaaggactcc ccaatgagat gagaactgag    300

cacatgccag aggaggtgag gactgaacca ttcaacacaa gtggtgaata gtcctgcaga    360

cacagagagg gccagaagca ctcagaactc caggggggtca ggagtggttc tctggaggct    420

tctgcccttg gaggttcctg aggaggaggc ttccatattg aaaatgtagt tagtggccgt    480

ttccattagt acagtgacta gagagagctg agggaccact ggactgaggc ctagatgctc    540

agtcagatgg ccatgaaagc ctagacaagc acttccgggt ggaaaggaaa cagcaggtgt    600

gaggggtcag gggcaagtta gtgggagagg tcttccagat gaagtagcag gaacggagac    660

gcactggatg gccccacttg tcaaccagca aaagcttgga tcttgttcta agaggccagg    720

gacatgacaa gggtgatctc ggtttttaaa aggctttgtg ttacctaatc acttctatta    780

gtcagatact ttgtaacaca aatgagtact tggcctgtat tttagaaact tctgggatcc    840

tgaaaaaaca caatgacatt ctggctgcaa cacctggaga ctcccagcca ggccctggac    900

ccgggtccat tcatgcaaat actcagggac agattcttca ctaggtactg atgagctgtc    960

ttggatgcaa atgtggcctc ttcattttac tacaagtcac catgagtcag gaggtgctgt   1020

ttgcacagtg tgactaagtg atggagtgtt gactgcagcc attcccggcc ccagcttgtg   1080

agagagatcc ttttaaattg aaagtaagct caaagttacc acgaagccac acatgtataa   1140

actgtgtgaa taatctgtgc acatacacaa accatgtgaa taatctgtgt acatgtataa   1200

actgtgtgaa taatctgtgt gcagcctttc cttacctact accttccagt gatcaggttt   1260

ggactgcctg tgtgctactg gaccctgaat gtccccaccg ctgtcccctg tcttttacga   1320

ttctgacatt tttaataaat tcagcggctt cccctctgct ctgtgcctag ctataccttg   1380

gtactctgca ttttggtttc tgtgacattt ctctgtgact ctgctacatt ctcagatgac   1440

atgtgacaca gaaggtgttc cctctggaga catgtgatgt ccctgtcatt agtggaatca   1500

gatgccccca aactgttgtc cagtgtttgg gaaagtgaca cgtgaaggag gatcaggaaa   1560

agaggggtgg aaatcaagat gtgtctgagt atctcatgtc cctgagtggt ccaggctgct   1620

gacttcactc ccccaagtga gggaggccat ggtgagtaca cacacctcac acatactata   1680

tccaacacac acacacacac acacacacac acgcacgcac gcacgcacgc acgcacacat   1740

gcacacacac gaactacatt tcacaaacca catacgcata ttacacccca aacgtatcac   1800
```

```
ctatacatac cacacataca caccccctcca cacatcacac acataccaca cccacacaca   1860

gcacacacat acataggcac acattcacac accacacata tacatttgtg tatgcataca   1920

tgcatacaca cacaggcaca cagacaccac acacatgcat tgtgtacgca cacatgcata   1980

cacacacata ggcacacatt gagcacacac atacatttgt gtacgcacac tacatagaca   2040

tatatgcatt tgtatatgca cacatgcatg cacacataca taggcacaca tagagcacac   2100

acatacattt gtgtatgcac acatgcacac accaatcaca tgggaagact caggttcttc   2160

actaaggttc acatgaactt agcagttcct ggttatctcg tgaaacttgg aagattgctg   2220

tggagaagag gaagcgttgg cttgagccct ggcagcaatt aaccccgccc agaagaagta   2280

ggtttaaaaa tgagagggtc tcaatgtgga acccgcaggg cgccagttca gagaagagac   2340

ctacccaagc caactgagag caaaggcaga gggatgaacc tgggatgtag tttgaacctc   2400

tgtaccagct gggcttcatg ctattttgtt atatctttat taaatattct tttagtttta   2460

tgtgcgtgaa taccttgctt gcataaatgt atgggcactg tatgtgttct tggtgccggt   2520

ggaggccagg agagggcatg gatcctccgg agctggcgtt tgagacagtt gtgacccaca   2580

gtgtggggtc tgggaactgg gtcttagtgt tccgcaagtg cagctggggc tcttaacctc   2640

tgagccatcc ctccagcttc aagaaactta ttttcttagg acatggggga agggatccag   2700

ggctttaggc ttgtttgttc agcaaatact cttttcgtgt attttgaatt ttattttatt   2760

ttactttttt gggatagaat cacattctgc agctcaggct gggcctgaac tcatcaaaat   2820

cctcctgtct cagtctacca ggtgataaga ttactgatgt gagcctggct ttgacaagca   2880

ctttagagtc cccagccctt ctggacactt gttccaagta taatatatat atatatatat   2940

atatatatat atatatatat atatattgtg tgtgtgtgtt tgtgtgtgta tgagacactt   3000

gctctaaggg tatcatatat atccttgatt tgcttttaat ttattttttta attaaaaatg   3060

attagctaca tgtcacctgt atgcgtctgt atcatctata tatccttcct tccttctctc   3120

tctttctctc ttcttcttct cacccccaag catctatttt caaatccttg tgccgaggag   3180

atgccaagag tctcgttggg ggagatggtg agggggcgat acaggggaag agcaggagga   3240

aagggggaca gactggtgtg ggtctttgga gagctcagga gaatagcagc gatcttccct   3300

gtccctggtg tcacctctta cagccaacac cattttgtgg cctggcagaa gagttgtcaa   3360

gctggtcgca ggtctgccac acaaccccaa tctggcccca agaaaaggca cctgtgtgtg   3420

actctggggt taaaggcgct gcctggtcgt ctccagctgg acttgaaact cccgtttaat   3480

aaagagttct gcaaaataat acccgcagag tcacagtgcc aggttcccgt gctttcctga   3540

agcgccaggc acgggttccc taggaaatgg ggccttgctt gccaagctcc cacggcttgc   3600

cctgcaaacg gcctgaatga tctggcactc tgcgttgcca ctgggatgaa atggaaaaaa   3660

gaaaaagaag aagtgtctct ggaagcgggc gcgctcacac aaacccgcaa cgattgtgta   3720

aacactctcc attgagaatc tggagtgcgg ttgccctcta ctggggagct gaagacagct   3780

agtgggggcg gggggaggac cgtgctagca tccttccacg gtgctcgctg gctgtggtgc   3840

atgccgggaa ccgaaacgcg gaactaaagt caagtcttgc tttggtggaa ctgacaatca   3900

acgaaatcac ttcgattgtt ttcctctttt tactggaatt cttggatttg atagatgggg   3960

gaggatcaga gggggagggg aggggcgggg agacggaggg aggaggggag gaggggagga   4020

ggggaggagg ggaggagggg aagggatgga ggaaaatact aacttttcta attcaacatg   4080

acaaagattc ggagaaagtg caccgctagt gaccgggagg aggaatgccc tattgggcat   4140
```

-continued

```
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggcc   4920
ctgcaacagg aagggaggga ggaagggggg gaacgagaga gaggaaagag agacagaagc   4980
taagataggg aatgagagag gaaggaagaa acgggaagaa attcagactc cttcctgagt   5040
tccgccaacg cctagtgaca tcctgtgcac accctaaggt ggcctttgtg tggcactggc   5100
ttgggtggtc gggaaaggca ttttcagctt gttgcagaac tgccacagta gcatgctggg   5160
tccgtgaaag tttctgcccg ttaacaagaa gtctctacta cttgtgacct caccagtgaa   5220
aatttcttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg gggtgtcaaa aggaaaagaa gggaaacagg cacttgggaa aatgtcctcc   5400
cgcccacccg aattttggct tggcaaccgt ggtggaggag caagaaacac gtggacgttt   5460
gaggaggcat ggggtcctag gaggacagga agcagaagga gagagctggg ctgacagcct   5520
gcaggcattg cacagtttca gaaggagatt acagcatgac tgagttttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag ggccaccaca   5820
tccccagaaa gagtggagct gctaaaaagc catttgtgat aggcacagtt atcttgaatg   5880
catggagcag agattacgga aaaatcgaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata attttcatgt tggagtttat ttgtgctaaa aggcagaaaa   6120
gggtaaaaag cacatcttaa gagttatgag gttctacgaa taaaaataat gttacttaca   6180
gctattcctt aattagtacc cccttccacc tgtggtaatt tcctgagata gtcagtgggg   6240
aaaagatctc tccttctctt ctttctcccc ctcccctcct ctccctccct ccctccctcc   6300
ctccctcctc tccctccctc cccctttcct tctttctttg ctccttctcc tctgcctcct   6360
tctccctttc ttcttcattt attctaagta gcttttaaca gcacaccaat tacctgtgta   6420
taacgggaaa acacaggctc aagcagctta gagaagattg atctgtgttc actagcgtgc   6480
aattcagagg tgggtgaaga taaaaggcaa acatttgagg ccatttcctt atttggcacg   6540
```

```
gcacttagga agtggaacat gcctaatcta ctggtttgta ccacctttcc ctataatgga   6600
ctgtttggga agctcctggg caaccgattc tggcatctca ttggtcagag gcctgttaaa   6660
tggtactctt atttgcaaag aaggctgtaa cttgtagctt taaaagcctc tcctcaagaa   6720
agaagggaga aaggatatgg ctagacatat ctaatagact taaccactgt gaaaagcctt   6780
agtatgaatc agatagaacc tatttttaac tcagttttga aaaaaataat ctttatattt   6840
atttgtgtgt gtgtgtgtgt gtgtgtgtgt gtgtgtgtgt gtgtgtgtgt gaaccacatg   6900
tagcaggtgc tggaggaggc cagaagaggg caccagatct cctggaactg acaccacaca   6960
tggttatgag ctgcctgatg tgggtgctgg gaactgaact ctcgtgttct gcaagagcag   7020
caactgttct cttaactgat gagccatctc tccagccccc cccataattt taattgttca   7080
ttttagtaaa ttttattcat aatcaattat cacagtataa aacaatgatt ttatatatat   7140
catatacata tcaaggatga cagtgagggg gatatgtgtg tgtgtgtgtg tgtgtgtgtg   7200
tgtgtgtgtg tgtgttattt gtgtgtgtgc tttttaagaa ggtgccatag tcactgcatt   7260
tctctgaagg atttcaaagg aatgagacat gtctgtctgc caggaaccct atcttcctct   7320
ttgggaatct gacccaaatg aggtattctg aggaactgaa tgaagagctc aagtagcagt   7380
gtcttaaacc caaatgtgct gtctagagaa agtcaacgtc atcagtgagc tgaggagaga   7440
tttactgagc ggaagacaag cgctctttga tttaagtggc tcgaacagtc acggctgtgg   7500
agtggagcct gtgctcaggt ctgaggcagt ctttgctagc cagctgtgat gagcagtgaa   7560
gaaagggtgg agatggaggc agggtgggag cagggctatg gttcagacta ggtatcgtga   7620
gcacaccagc tggttgactt gtggtctgtg ggtcaggcgt tgtaaacgcc ctcagggtca   7680
ggcagtcaca ttgcttgaag ctgaatgggt gaggcaacac agagagtgca aagaaggcaa   7740
agtaccacct cttccccgac ccaggtcact tctgggttat agctgagact ccggacagca   7800
tgcaaccagc tggttagagc ttcagggaaa acttgatgtc tgcatgttgc tatgaaatgt   7860
gattcggtac atctggagaa aatttataat gctggctcag tcaagcactg aacaaaggta   7920
ccttggcttt gggagctaca tgacattgac ttgtaggcag actttttttt ttctgcccgc   7980
caattcccag ataaccaata tggaggctca atattaatta taaatgctcg gctgatagct   8040
caggcttgtt actagctaac tcttccaact taaatgaacc catttctatt atctacattc   8100
tgccacgtga ctttaccttg tacttcctgt ttcctctcct tgtctgactc tgcccttctg   8160
cttcccagag tccttagtct ggttctcctg cctaacctta tcctgcccag ctgctgacca   8220
agcatttata attaatatta agtctcccag tgagactctc atccagggag gacttgggtg   8280
ctcccccctc ctcattgcca tccgtgtctt cctcttccct cgcttccccc tcctcttcct   8340
gctcttcctc ctccacccct cctttcatag tattgatggc aagggtgttc tagaatggag   8400
gagtgcccat aggcatgcaa agaaaccagt taggatgctc tgtgaggggt tgtaatcata   8460
agcgatggac acaattcaag ccacagagtg aagacggaag gatgcactgt gctctagagc   8520
aacttctggg gcagaatcac agggtgagtt tctgacttga gggcgaagag gccacgagga   8580
agggagtgag tttgtctgag ctagaagcta cggcccacct cttggtagca gacctgccca   8640
caagcatgct ttgttaatca tgtgggatct gatttcctcc taaatctatg ttcaactctt   8700
aagaaaatgt gaattctcac attaaaattt agatatacgt cttttggtgg ggggggtgta   8760
aaaaatcctc aagaatatgg atttctgggg gccggagaga tggctcagag gttaagagaa   8820
ctggttgctc ttctagacat tctgagttca attcccagca accacatggt ggctcacaac   8880
```

```
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaaccaaa aaaaaaaaaa aaaaaaaaaa aaaaaaaaga gtatggattc   9180
taagaaagcc gtaacagctg gagctgtgta cggagttcag cgtggtacta gaagaacaga   9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaaggggg gatttttaat taggaaaacg atttcctgta  10080
tcacttgtga aactggaggt tgatttgggg cataggacaa tagatttgat gctttgcaaa  10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg gggggcaggg gcgggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga catggtgctg gagaaaggga  11280
```

```
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta ttttattttt attattgtaa attatgtatg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttccttc ccaaaatgcc aagtgtacaa ggtgagggaa tcacccttgg attcagagcc  12120
cagggtcgtc ctccttaacc tggacttgtc tttctccggc agcctctgac acccctcccc  12180
ccattttctc tatcagaagg tctgagcaga gttggggcac gctcatgtcc tgatacactc  12240
cttgtcttcc tgaagatcta acttctgacc cagaaagatg gctaaggtgg tgaagtgttt  12300
gacatgaaga cttggtctta agaactggag caggggaaaa aagtcggatg tggcagcatg  12360
tacccgaaat cccagaactg gggaggtaga gacggatgag tgcccggggc tagctggctg  12420
ctcagccagc ctagctgaat tgccaaattc caactcctat tgaaaaacct ttaccaaaca  12480
aacaaacaaa caaataataa caacaacaac aacaacaaac taccccatac aaggtgggcg  12540
gctcttggct cttgaggaat gactcaccca aacccaaagc ttgccacagc tgttctctgg  12600
cctaaatggg gtgggggtgg ggcagagaca gagacagaga gagacatgac ttcctgggct  12660
gggctgtgtg ctctaggcca ccaggaactt tcctgtcttg ctctctgtct ggcacagcca  12720
gagcaccagc acccagcagg tgcacacacc tccctccgtg cttcttgagc aaacacaggt  12780
gccttggtct gtctattgaa ccggagtaag ttcttgcaga tgtatgcatg gaaacaacat  12840
tgtcctggtt ttatttctac tgttgtgata aaaaccgggg aactccagga agcagctgag  12900
gcagaggcaa atgcaaggaa tgctgcctcc tagcttgctc cccatggctt gccgggcctg  12960
ctttctgcaa gcccttctct ccccattggc atgcctgaca tgaacagcgt ttgaaatgct  13020
ctcaaatgtc actttcaaag aaggcttctc tgatcttgct aactaaatca gaccatgttt  13080
caccgtgcat tatctttctg ctgtctgtct gtctgtctgt ctgtctatct gtctatcatc  13140
tatcaatcat ctatctatct atcttctatt tatctaccta tcattcaatc atctatcttc  13200
taactagtta tcatttattt atttgtttac ttactttttt tatttgagac agtatttctc  13260
tgagtgacag ccttggctgt cctggaaccc attctgtaac caggctgtcc tcaaactcac  13320
agagatccaa ctgcctctgc ctctctggtg ctggggttaa agacgtgcac caccaacgcc  13380
ccgctctatc atctatttat gtacttatta ttcagtcatt atctatcctc taactatcca  13440
tcatctgtct atccatcatc tatctatcta tctatctatc tatctatcta tctatcatcc  13500
atctataatc aattg                                                   13515
```

<210> SEQ ID NO 2
<211> LENGTH: 14931
<212> TYPE: DNA
<213> ORGANISM: Cricetulus griseus
<220> FEATURE:
<221> NAME/KEY: misc_feature
<222> LOCATION: (2176)..(2239)
<223> OTHER INFORMATION: n is a, c, g, t or nucleotide is missing

<400> SEQUENCE: 2

```
catgtacact tatgcaagta tgatatggcc caacacagta ttttacacca atttttatct     60

ataaaatata catgtacatc aaaatatatt attaataata acatcattat tctttctttc    120

caagtaataa acacatacac tgaaattttg gttcttgtgg ataattttaa tgaaacagga    180

aatgcaaatt tatcttagca tgtttacttc actttctttg catagataac cagtaatcac    240

attgatggat catgtagtga aatgtatttt taggtatcta aggaattttg gcttcgtttt    300

gtgcttgttg acactgaatt ctattcctaa caacagtgtg taaggattct gtctgatttc    360

ttttaccagt atttgtccat ttgcattttc tttattattc atggctgctg ttctagaaag    420

tggaaggtag tgtgtcaagt ctgtttaaca tgtttccctg atgatcagtg tcttaacacc    480

tctctgagta catgttggcc aatgtcgttt ctagacccat ctattcttgc ttgacttatc    540

ctggtacatg cctgccaaga aatttctcct catcctttct gtctcttcac tgatttactt    600

gatgtgtgga tttcacattg atcatatgga aatagaagat acaattttct ttattcacag    660

tttggaagac tttcaatctc atagatcatc attatttttt gctactgttc cctatgctat    720

ggtgaaattt ccatttgaat aattgcttaa acaattaaca agaaagaatc tatttttact    780

tgcaataact tccatttcag aacatttact acactgttac tatatccaaa aactagtttt    840

atatatcatg tgagaaatga ctaattcata atttggccat gacatttttt tcagaaacag    900

aaaaagtgac caatacatac acaatgctat aaatattaag acttcagcaa attaaatatt    960

tattcatgat atcacataaa attcatttat tatgttttat ttaaatgtgt ttttaaaaca   1020

gtggtatcac taaatattaa gttagatgtg tttatgtgct taatgaattt atattttaga   1080

atgttataag ttgtatatag tcaaatatgt aataaatttt attttttagg tctttctcat   1140

taaggtattt taattttggg tcccttttcc agagtgactc tagctcatga tgagttgaca   1200

taaaaactaa acagtacaaa atgtacattg cattcagtat tgcacttgat ctttgcactg   1260

aagtttgagt cagttcatac atttagtact tgggaagtac attaagctaa ctttcattgc   1320

tctggcaaaa tgctcgataa gataagagtc tattgtggaa agccatggca gcaggaaagt   1380

aagactgctg atgatgttta atccatagtc aagacgcaga aggagatgaa tgctggtatc   1440

caacattttt tgctgttcat ttctctagaa accctagtcc ataaagatgt atgacttgca   1500

ttcaaaatgc gtccccttca gttgttcaac ttttctgtaa atatcctttc aggcatgtct   1560

agaagattgt ttcgcaaata cttctcaatc cattcaagtt gatagtgcag attaatcact   1620

gcagaataaa agcctgtaac ttggctcacg tgccaaggaa tatgcacact cctgacacat   1680

caataagtaa atcaaagtgt agcttttgcc tttaacattg ccagacttat gtaatgttct   1740

gcacgttctt cctccatcac tttttattct aatggtgttt ccttgacatt gaatcacgct   1800

gtggaagctg cttagaatta acattgaaat ctactgatat atttatgatg cagcaattta   1860

gatttactat tttacttaga attttttata attgagagaa tataatattt tcacagttat   1920

ctatctgctg taaatagagg attttaaaaa aaatctctat aacttttttt tacaacacac   1980
```

```
agtaaaatta agttaaaatt taataaagtc actatgttga tttcaaagtg tgctacgccc   2040
acggtggtca cgcaggtgta gcagaagatg ccactaaggt gggctaaggc cgatgggttg   2100
gggtctgcgc tccctggaga tgagccccag gcggttccct ggcaatcagc tgcgatcatg   2160
atgcccgatg agccannnnn nnnnnnnnnn nnnnnnnnnn nnnnnnnnnn nnnnnnnnnn   2220
nnnnnnnnnn nnnnnnnnnc tgggtgactt tatggaaaga atttgataga tttcatgatg   2280
tagaagaatt ttattaggct tattttacag gagactaaga ccctgggacc taaagatatc   2340
tgggtcctga gaatcaggaa atgggtagag acgtggttga tggtatgaga cagattttag   2400
agaactctta gatcatgggc aatgaccgca atctgatgct tagaatagat catctataaa   2460
caattatgct gttctttttc tttctgttgt atgatctgat gatgtagccc ccttgccaag   2520
ttccctgatc ccccttgcca agttccctga ttgtaacagt atataagcat tgcttgagag   2580
catattcaac tacattgagt gtgtctgtct gtcatttcct cgccgattcc tgatttctcc   2640
ttgagccttt tcccttgttc tccctcggtc ggtggtctcc acgagaggcg gtccgtggca   2700
aaagtgtata aatgttctaa aacatttgaa ctctaaaaca tgcaaaatga aaaattaaaa   2760
taaataaaca tgaaaattaa aatatattag ctgctaaaag ttaaacaata ctatataata   2820
ttttgttatt agaattcaaa atcacattag ttggatttaa tttgaacatt gcattctttc   2880
aataataatt tcaataaaaa aagtttcccc atgatagtag aaaataataa catatgtatc   2940
tatctattta tttaactaca catatatagc atttgtttca actaaaataa atgaatgagc   3000
aaagcaccta agtaattggt gtctattata tttatgaagc caatagtttc aaataaatta   3060
tcatgcataa ggaggtattg caaatgttaa accttttttg aaacagatat tcccagttac   3120
agaaattata atttctaatc tttcctataa gtagaatgat gataattaat ataggccatt   3180
tgtaaataat gttcagatta aaatattctc tatttcacta gagaagaatg atattaaatg   3240
tattatattt tatttcccat tttgtttgca ccactattct atatccctca gcagtttaaa   3300
tttgtttcac catatgtgtg tgtgtttgta tcttaaatat ggcactaaaa ttagaataat   3360
ttaatataaa tctttaggag aaaagatatt gaattatttt atgttgatag gaaaatatct   3420
tttaattgtc caagaatact ttttcttcta ttttaggact gatcagaccc aggactaata   3480
ttttatatgt actaattcta tgtaccaaaa tatgttatta tctcatgaat tctgtctcaa   3540
tattgaggta ataaaaatag tccatcatga actttaaaat taaaataatg attaattaat   3600
ttttattcat attttgtttg tatgaatggt tatacatcac atgtgtgcct ggtgactgtg   3660
aatgtcagga gaaggtatga aagccactgg aattggaata agagataata tttgagatgt   3720
tatgtgggtg ctgagaatta gacgcaagcc atcttcaaga atagccagca tactatacca   3780
ctgagtaatc cattcatccc tcaataatta tctttgtaga cagtaaatat atttctaaac   3840
tataaatgac cagaaaaatt aatgtattat taatgaagac attcatctca tgtgacacac   3900
ttcacctgtc taaatcagta acactctctc cactaattaa gattttctaa gtgcatgaca   3960
cttactattt ctaaagctgt ccaatggggg ccagtcccca gtcagcaccc agtgagataa   4020
tccatgaatg catttatatc ttaggaaaaa ttcttatcta tgtagtattt agaacatttt   4080
catgtgaggg gataaacaag gaagcacaga tgctttctga tagaaacttt ctctttaatt   4140
catctagaaa aaaaaaacct ctcaggaaaa tctctcttgc tctcctccca atgctctatt   4200
cagcatcttc tccctactta attctagatc tttttctcta tgcctccttg ctgctgccct   4260
gctggctctg ctctatgcct ccccatgtca cttttctttg ctatctcacc gttaccttct   4320
ctgcctcact ctctgccttc ttctctgctt ctcacatggc caggctctgg acaattatag   4380
```

```
ttatatgtta cattctcata acacatgata tgtcacatag tttctctcag gctagggata   4440
tcacaatgac tggccaatga gcaagtggcc ttgcatgtag ctctaagttg gtgatggttc   4500
ccagacagta agtagccatt tggttgaaat ttgaggttgg gtagtacatg aagactgaat   4560
tttcttcaaa ctctggcctt gaaatagtaa aacaacacct atgaaaatga cgacctgtat   4620
ttgtctttag aggcaaccac atattgtctg cagggcctgc tttgaatttg ctctgaagtt   4680
agcttgtttg tgtaaaagga agaatcctat atcagcctga gaaatgtaaa atatcctagc   4740
atttcaagtc atcaaaatta tatggagagt ataaatcatc cttctgacta ttcatagtca   4800
tatttgtgtc caccaagtat aaaacacact accaaagggc tgtggaaaaa atcgccataa   4860
ctgttcttat tagggaggca tagcagtggt acctgaggaa gttacagcaa caaccagtca   4920
tccagtcaat aaccccatgg ctttgccact tggaggtacc caataatgtt tggctttgcc   4980
gagtaggact ccaacaaatt cagagggtca atttttaaat gctggttgtc actgctgaac   5040
agtcccattg ccctctgcat aattccacaa tggaaagctt tttacactga ttgccaatca   5100
ttaaacagcc tactcagcat aaacaggtat gatattattc tgcattttgt tacattacta   5160
gatgaattcc tatttcttcc tacaatagtg gaactgaaaa aagatacaca atcatactac   5220
ccctctacta atcttatgac ttatatcatt tcaattttca gaccataatg caaactattg   5280
accaaaacat gtgaagatga aaaatagaaa tgtagaataa tattacatat aaaaagaaaa   5340
ggcggactta ttttgtttta tttcttagca tgcatagcaa tacatgattt gaggtttata   5400
taataaaggg acaataaatc ttcaagaaac ttacccctac tgaattaaaa tattaaagaa   5460
ggtcacacat ttactcaaat atattagact actgggcaaa tagacatgaa aagtagagtt   5520
aatattgagg taggccttct gtgaaatgtc taaggaaatt atgtttcata cagtgtgtaa   5580
ccaagtggga atcatatcag aaagcagtca aaagcttata ttacaagtaa cagatgcttg   5640
gttatatgac ctcccagagc ttgactgtct atacacaaaa agtggtgtta ataaaactgt   5700
aatttgggct atgttttttt aaatggcttc accaacatga aaggaaggga atgagcatgt   5760
catggatgct tagagattat gcttccagca agaagaattg agctttggct cttattacag   5820
aaacatgaca aggtgtgagt tttatttatt agaaattata taatatttta agctggggac   5880
taaaaatttt attgaaacaa acaggcaagg gataggcatg tactagaagc aaaaatagga   5940
tgtcaatgct gtaatgttat tttttggacc aaaatagtat ttcctataga aatgacaatg   6000
atcttaggtt attattcttc ataaagatga caagttcaca agatatccta gttcattaaa   6060
atcgttttag tcatttaata gagtgctgtg atagattaca caaaggaaag cacttacgat   6120
gagaaataat gatatccaca attattttct taattcttag aaacattcta ttgttatatc   6180
tcaatctcag aagccactta ttgctttatt attgaaacat atgaaattgt aagttatata   6240
ttgtctatgg tgacatttca aagaacatgt gacgtacagt gtagcacaga taaagaacat   6300
aactgcagct gaatcagtaa ctaaacttac atacattaaa tctgccatgt tggcaacagt   6360
gtgtgcacta ccaaaggatg tactaatgct cacgacactc ccctatgtca ccctttgttc   6420
atcattacat catagtcta ttttgtttgc ttttgaaatc tagaccaagt cttttgtgtc   6480
tttccaagca cagagctcat taatttacct catagacttg ttaaacttct tctggttcat   6540
caattgaata gaaatactca ctactaatta tgtgagaccc tgccagtacc atagcacatg   6600
gataattttt acataaaaca tgcatacaag taagattatt cagactgaac atgaatttta   6660
gagaaatcag gaaggagtat atgggagtgg ttggagtgag actagagaaa tgtaattaaa   6720
```

```
ctataatctc aatacaaaga tctactaagc aaaaaacatg aaacattgtc attcaagtga   6780
aacatcagtc ttcaaattgg aaagatattt ttactaggaa aatgtctggt agatggttat   6840
tatctagaaa acacaaaaat tagaaaacgg taaactttaa taaaaagaat aatacaatga   6900
gactacatga aaagttctta actaatgaaa caaatatctt gaaacttttt tcttaaaagt   6960
ttaatatcaa taaccatcat ggaaattcaa attaaaacta tttacatatt acccctgaaa   7020
taataactaa tacccaataa aaataatata aacaaaaaat ggcaatgcat gccatcatgg   7080
atttgggaga gagaatgttc attgcagttc tgaatggata ctggtgccac cacggtgaaa   7140
atctctgtat aggtccttcc aaaagctgaa aatagacata tcacaagacc tgccacacat   7200
ttttcaagca aatacccaaa ggactctacc tgactgcaga gacactttct cataaaatat   7260
tattgttgat ctattcataa tatctggaaa atagaaacag ccaagatgcc catcaactga   7320
ttaatagatg ataaaattat tgtacatttc agtgtaatat tattcagttt ttaagaaaaa   7380
tgaaattatg taataagcat gtaaatggat atatcttgaa acaaccattc cccattatat   7440
tacctaaaca ttgaaagtcc aaaatcatat gatcttttta gtggatctac taatcttttg   7500
ctatatgtat tttattgaac tacccatgga tgtgagataa ttggtaacaa cagcacatgg   7560
gagagcatgg gatcattcaa ggaagattag agagaatgca ttttttagga gataatggag   7620
gagcaataga aaggattaaa tgaggttact gatgaaagtg atggttagag aaggcaatat   7680
gaggagggat aactagcact tagggccttt tgaaaaagac atagagaaaa tactattgta   7740
gaaacttcct ataattggtg tatagttata tacaccaaag agctcagatg gagttaccct   7800
ataatggaaa tattaactac tttttatcac tgtgataaaa catcctgaac agagcaacat   7860
agattgggaa gcatttactt tggcttacag ttctaacggg ataaaaattc atgatgaaag   7920
aatgaatatg tcagcaaaca gcagtagcaa tggcctgaga agcaggtgag agctcacatc   7980
ttgaagtgta agaatgtagc agagagaaca aactgcaaat gaccagaaaa tgcttttgga   8040
tcagagccca tacccctctg actgacttct ccagaaattc tgaacaaata aaactcccca   8100
aacagagcca taactgaagg tccagtgtct gagactacta ggggtatttc ttattcaaac   8160
cactacaatg gggtgggggg agcaatcctc caagtaggca ctacacacag acaaataaaa   8220
actctagtaa ctggaatgga ttgacttatt tgaattactt gccagtggag ctacatagag   8280
cacaattatt gtatttaaat taccctttat gatcttacaa aacttgacag taagatcata   8340
ttgctaaaga aaccacatat ttgaatcagg gaacatggtg atatctagtt gttcttcaac   8400
tggaaacttc atgctttctg cccagcattc atgttgctgg aaagagcaat gtacactacc   8460
agtgtagaaa ttaaatcatc aatcttatca agatgtggat cctataagtt acaataaaaa   8520
ttagcctgat aagatatccc caccagaaga atattcacat aaatgctatg ggagcaacaa   8580
gctattttct aaattagctt taatcctatt ctacaagaga gaatccatat ctagaatagt   8640
tatagggatc aagaacccat ggcttgattg gtcataggcc caatgggaga tcctaatatt   8700
attgttctac aaaatgaaaa taactcctaa tgacttgttg ctgcagtaat aagttagtat   8760
gttgctcaac tctcacaaga gaagttttgt cttacaataa atggcaatta aagcagcccc   8820
acaagattta tatcataccg atctcctcat ggcctatgca tctagaagct aggaaacaaa   8880
gaggacccta agagagacat acatggtccc cctggagaag gggaaggggg caagacctcc   8940
aaagctaatt gggagcatgg gggaggggag agggagttag aagaaagaga aggggataaa   9000
aggagggaga ggaggacaag agagagaagg aagatctagt caagagaaga tagaggagag   9060
caagaaaaga gataccatag tagagggagc cttgtatgtt taaatagaaa actggcacta   9120
```

```
gggaattgtc caaagatcca caaggtccaa ctaataatct aagcaatagt cgagaggcta   9180
ccttaaaagc ctttctctga taatgagatt gatgactacc ttatatacca tcctagagcc   9240
ttcatccagt agctgatgga agcagaagca gacatctaca gctaaacact gagctagttg   9300
cagacaggga ggagtgatga gcaaagtcaa gaccaggctg gagaaacaca cagaaacagc   9360
agacctgaaa aaaatgttgc acatggaccc cagactgata gctgggagtc cagcatagga   9420
cttttctaga aaccctgaat gaggatatca gtttggaggt ctggttaatc tatggggaca   9480
ctggtagtgg atcaatattt atccctagtt catgactgga atttgggtac ccattccaca   9540
tggaggaatt ctctgtcagc ctagacacat gggggaggtt ctaggtcctg ctccaaataa   9600
tgtgttagac tttgaagaac tcccttgaga agactcaccc tccctgggga gcagaaaggg   9660
gatgggatga gggttggtga gggacaggag aggaggggag ggtgagggaa ctgggattga   9720
caagtaaatg atgcttgttt ctaatttaaa tgaataaagg aaaagtaaaa gaagaaaaga   9780
aaacaggcca aaagattata aaagacagag gtggtgggtg actataaaga aacactatta   9840
tctaaataaa aatatgtcag aagcacacat gaacttatag tgtttatgaa agtatgtata   9900
ataactacat aatctcaagc caagaaaaaa atatcatctt tcagtgatga aggtgatttt   9960
atttctccca gaattaaagc caaagaccta atgaaagtaa ttatcttcaa aaggttgaaa  10020
atacatactt tgcaatacac agatctgcct agaaatctca tgttcacaat acacatgatg  10080
ctcaattgaa ttccattcaa tgttacagtt tagataaaca gtttgtagat aaactcacaa  10140
tgtatcattt ctttttattt tttgaccaaa cagcttctca tctgttattc agaataattc  10200
ctcgatggca ggatatccat cccaattggg ggaaggggag aatttgaaga aaacctagac  10260
cacatacata tttgccattg ggaaacaaag tctaaaatga tgttgttcac atcttctcta  10320
ctagtcctct ccccgtccca aagaaccttg gtatatgtgc ctcattttac agagagagga  10380
aagcaggaac tgagcatccc ttacttgcca tcctcaaccc aaaatttgca tcattgctca  10440
gctctgccct tctcatatga cagttacaag tcaaggcttc caaagtccct ctgtcatgtt  10500
tggtgtcaat agtttataca gatgacttca tgtcttcata tctaatgtct tatatagatt  10560
aatattaaac aatgttattt ctctaaccac attttaaatt aatttaaaaa tccattaatt  10620
gtgtctataa aatgcagaca gagtgctgag acacaatata agcctgatga tctgaatttg  10680
aaactcacac ccaccacatg gagaatcaac ttccaaaaat tttcctatta cttccacact  10740
tacaccattg tacaaacaca ataataatga acaaaatgaa atgaaataaa aaattaagtc  10800
tctgtaggta atgctactgt gcagcaaaag taaaaatggc agcttaagct tgctttatgg  10860
ttacacttta ccatcttcca ttaattataa ggacttcaat catggcagaa ctatgctgtt  10920
attgtctcag tgtaacctaa ccaggtgttc cagatgttct taatgtggac acctaaacta  10980
tttgatattt gggttaagat ctttccctct ttcagaagaa acctcaggac agagggaatc  11040
ttgtctttta attttgagtc tgtagacttt ttccatttca aatatacatg aaacaagtga  11100
tgaagaaaat taatcaaaag gtgggaattg caatgatatt aggttcaata ttaagcttca  11160
atattatcat ggaatcgcct gttatacact gagtgtttgg caataaggga tttttagaag  11220
aaggagtttt tattctcaac aggttcctta agtttagctc aaataaatct aagcaatcca  11280
ctctagaatt aaatagtttc ctaagggcac agctatgaat agagctcaat ttacatataa  11340
aattttgttc accatttatg tcattccagt tttcattagt acaaggaaaa tacaaaatat  11400
ttagatgtca atatcaagtg aatagttcat ctccttttt aatatatatc acctaaatca  11460
```

-continued

```
ccattttctc agaaaaatct ggcctgaagt tctgtctgga acttcaacat gaaaaatatg  11520
cacagcttgc tattataaat cctagttgat ttttaagatt catgtctggt gtctgactca  11580
gaggggccag aggctagaca aatatttttt gaatcttcat tgtgaagatt tttaatgatt  11640
attttaatat aaataacaaa gatgatggat aatgtaactt tgtacagttc atagacgctg  11700
aactactttg tgcttaaaat gttagttccc tatcataaat gataggtgat aagtgtatgt  11760
ttaatacttt ccctctgagc tatattcatg tactagagaa ttattttaaa catgaaaaga  11820
ctgtgtttat agtctcagct cctgagaact ggtccaacct taggcaggtg aatgccagga  11880
gcaacgtttt tcttctacag aggatgcttt gctgccaagc aacctggttg tgtggaaatg  11940
ttcctttttt aatcaagttt aaagggtctt catcatgctg ttgctccaca tattttcagg  12000
ttagagcttg gtccttggag tattatcttt taccagaaaa ttcatagtat tctttcaata  12060
actaacaact aaacttttcg ataaaaaaga attggaattt caattttaaa gcctgagtaa  12120
aattcttgtg aatcaggata ttttatttta agtcttatct tttaaaaagt tattttattt  12180
tttaaaaaat tataatatac tttcataatt tccctccttc acttttcttt acaaacactt  12240
ctatagatca ccatgtgttt tttttttac atttatggcc tctttctgtt cattgttatt  12300
acatacaaat agtcttgcct atagaagaac accacaattt gttacctgat aacaaattat  12360
caacccttaa aacctacaaa ctattgatat tactgaaaag actatactta tagatgtaaa  12420
gatatatgtg tgtgcacata tatagataca catatatgta ggatttttaa ttttagattt  12480
tagacatcaa aattatttat atgactgaga aactagacac tataaatgag cattcagtat  12540
tcaacaccgt gattttagat attgtcacaa tgacagaaaa ttttcttata gaaaatttta  12600
agttttgtga ttgctctgtg cacttagtga agtctcacag aaaaagaatc atagtatttt  12660
tagtttataa taaaaagtac atataattaa aatggttggc acaaaacaac atttgagcat  12720
ttttcctatt tactatcaag tagtatcatt ttgaaataat aatttgacta gtttcaaaaa  12780
tgaaaacaaa atttaaacta aatgcctaat ctagcctgat aacattttta tgaatgaaat  12840
tattcaatag tgttatcaat taggggccca aaacttttcc taaaataaaa cttttaattt  12900
ttttccattt ttatttaaat tagaaacaaa attgttttac atgtaaatca gagtttcctc  12960
accctcccct tctccctgtc cctcactaac accctacttg tcccatacca tttctgctcc  13020
ccagggaggg tgaggccttc catggggaaa cttcagagtc tgtctatcct ttcggatagg  13080
gcctaggccc tcacccattt gtctaggcta aggctcacaa agtttactcc tatgctagtg  13140
ataagtactg atctactaca agagacacca tagatttcct aggcttcctc actgacaccc  13200
atgttcatgg ggtctggaac aatcatatgc tagtttccta ggtatcagtc tggggaccat  13260
gagctccccc ttgttcaggt caactgtttc tgtgggtttc accaccctgg tcttgactgc  13320
tttgctcatc actcctccct ttctgtaact gggttccagt acaattccgt gtttagctgt  13380
gggtgtctac ttctactttc atcagcttct gggatggagc ctctaggata gcatacaatt  13440
agtcatcatc tcattatcag ggaagggcat ttaaagtagc ctctccattg ttgcttggat  13500
tgttagttgg tgtcatcttt gtagatctct ggacatttcc ctagtgccag atatctcttt  13560
aaacctacaa gactacctct attatggtat ctcttttctt gctctcgtct attcttccag  13620
acaaaatctt cctgctccct tatattttcc tctcccctcc tcttctcccc ttctcattct  13680
cctagatcca tcttcccttc ccccatgctc ccaagagaga tgttgctcag gagatcttgt  13740
tccttaaccc ttttcttggg gatctgtctc tcttagggtt gtccttgttt cctagcttct  13800
ctggaagtgt ggattgtaag ctggtaatca tttgctccat gtctaaaatc catatatgag  13860
```

```
tgatgtttgt ctttttgtga ctgggttacc tcactcaaaa tggtttcttc catatgtctg  13920

tggatttcaa tagcacaaac aacatacagt atcttggggc aacactaacc aaacaagtga  13980

aagaccagta tagcaagaac tttgagttta aagaaagaaa ttaaagaaga taccagaaaa  14040

tggaaagatc tcccatgctc tttgataggc agaatcaaca tagtaaaaat ggcaatcttg  14100

ccaaaatcca tctacagact caatgcaatc cccattaaat accagcacac ttcttcacag  14160

acctgaaaga ataatactta actttatatg gagaaacaaa agacccagga taggccaaac  14220

aaccctgtac aatgaaggca cttccagagg catccccatc cctgacttca agctctatta  14280

tagagtaata atcctgaaaa cagcttggta atggcacaaa aatagacagg tagaccaatg  14340

gaattgagtt gaaaaccctg atattaaccc acatatctat gaacacctga ctttgacaaa  14400

gaagctaagg ttatacaatg taagaaagaa agcatcttca acaaatcgtg ctggcataac  14460

tggatgctgg catgtagaag actgcagata gatccatgtc taatgccatg cacaaaactt  14520

aagtccaaat ggatcaaaaa cctcaacata aatccagcca cactgaacct catagaagag  14580

aaagtgggaa gtatccttga ataaattggt acaggagacc acatcttgaa cttaacacca  14640

gtagcacaga caatcagatc aataatcaat aaatgggacc tcctgaaact gagaagcttc  14700

tgtaaggcaa tggataagtc aacaggacaa aatggcagcc cacggaatgg gaaaagatat  14760

tcaccaatcc tatatctgac agagggctgc tctctatttg caaagaacac aataagctag  14820

tttttaaaac accaattaat ccgattataa agttgggtag agaactaaat aaagaattgt  14880

taacagagca atctaacttg gcagaaagac acataagaaa gtgctcacca t           14931
```

<210> SEQ ID NO 3
<211> LENGTH: 4001
<212> TYPE: DNA
<213> ORGANISM: Cricetulus griseus

<400> SEQUENCE: 3

```
ccaagatgcc catcaactga ttaatagatg ataaaattat tgtacatttc agtgtaatat     60

tattcagttt ttaagaaaaa tgaaattatg taataagcat gtaaatggat atatcttgaa    120

acaaccattc cccattatat tacctaaaca ttgaaagtcc aaaatcatat gatcttttta    180

gtggatctac taatcttttg ctatatgtat tttattgaac tacccatgga tgtgagataa    240

ttggtaacaa cagcacatgg gagagcatgg gatcattcaa ggaagattag agagaatgca    300

ttttttagga gataatggag gagcaataga aaggattaaa tgaggttact gatgaaagtg    360

atggttagag aaggcaatat gaggagggat aactagcact tagggccttt tgaaaaagac    420

atagagaaaa tactattgta gaaacttcct ataattggtg tatagttata tacaccaaag    480

agctcagatg gagttaccct ataatggaaa tattaactac tttttatcac tgtgataaaa    540

catcctgaac agagcaacat agattgggaa gcatttactt tggcttacag ttctaacggg    600

ataaaaattc atgatgaaag aatgaatatg tcagcaaaca gcagtagcaa tggcctgaga    660

agcaggtgag agctcacatc ttgaagtgta agaatgtagc agagagaaca aactgcaaat    720

gaccagaaaa tgcttttgga tcagagccca tacccctctg actgacttct ccagaaattc    780

tgaacaaata aaactcccca aacagagcca taactgaagg tccagtgtct gagactacta    840

ggggtatttc ttattcaaac cactacaatg gggtgggggg agcaatcctc caagtaggca    900

ctacacacag acaaataaaa actctagtaa ctggaatgga ttgacttatt tgaattactt    960

gccagtggag ctacatagag cacaattatt gtatttaaat taccctttat gatcttacaa   1020
```

-continued

```
aacttgacag taagatcata ttgctaaaga aaccacatat ttgaatcagg gaacatggtg   1080
atatctagtt gttcttcaac tggaaacttc atgctttctg cccagcattc atgttgctgg   1140
aaagagcaat gtacactacc agtgtagaaa ttaaatcatc aatcttatca agatgtggat   1200
cctataagtt acaataaaaa ttagcctgat aagatatccc caccagaaga atattcacat   1260
aaatgctatg ggagcaacaa gctattttct aaattagctt taatcctatt ctacaagaga   1320
gaatccatat ctagaatagt tatagggatc aagaacccat ggcttgattg gtcataggcc   1380
caatgggaga tcctaatatt attgttctac aaaatgaaaa taactcctaa tgacttgttg   1440
ctgcagtaat aagttagtat gttgctcaac tctcacaaga gaagttttgt cttacaataa   1500
atggcaatta aagcagcccc acaagattta tatcataccg atctcctcat ggcctatgca   1560
tctagaagct aggaaacaaa gaggacccta agagagacat acatggtccc cctggagaag   1620
gggaaggggg caagacctcc aaagctaatt gggagcatgg gggaggggag agggagttag   1680
aagaaagaga aggggataaa aggagggaga ggaggacaag agagagaagg aagatctagt   1740
caagagaaga tagaggagag caagaaaaga gataccatag tagagggagc cttgtatgtt   1800
taaatagaaa actggcacta gggaattgtc caaagatcca caaggtccaa ctaataatct   1860
aagcaatagt cgagaggcta ccttaaaagc ctttctctga taatgagatt gatgactacc   1920
ttatatacca tcctagagcc ttcatccagt agctgatgga agcagaagca gacatctaca   1980
gctaaacact gagctagttg cagacaggga ggagtgatga gcaaagtcaa gaccaggctg   2040
gagaaacaca cagaaacagc agacctgaaa aaaatgttgc acatggaccc cagactgata   2100
gctgggagtc cagcatagga cttttctaga aaccctgaat gaggatatca gtttggaggt   2160
ctggttaatc tatggggaca ctggtagtgg atcaatattt atccctagtt catgactgga   2220
atttgggtac ccattccaca tggaggaatt ctctgtcagc ctagacacat gggggaggtt   2280
ctaggtcctg ctccaaataa tgtgttagac tttgaagaac tcccttgaga agactcaccc   2340
tccctgggga gcagaaaggg gatgggatga gggttggtga gggacaggag aggaggggag   2400
ggtgagggaa ctgggattga caagtaaatg atgcttgttt ctaatttaaa tgaataaagg   2460
aaaagtaaaa gaagaaaaga aaacaggcca aaagattata aaagacagag gtggtgggtg   2520
actataaaga aacactatta tctaaataaa aacatgtcag aagcacacat gaacttatag   2580
tgtttatgaa agtatgtata ataactacat aatctcaagc caagaaaaaa atatcatctt   2640
tcagtgatga aggtgatttt atttctccca gaattaaagc caaagaccta atgaaagtaa   2700
ttatcttcaa aaggttgaaa atacatactt tgcaatacac agatctgcct agaaatctca   2760
tgttcacaat acacatgatg ctcaattgaa ttccattcaa tgttacagtt tagataaaca   2820
gtttgtagat aaactcacaa tgtatcattt ctttttattt tttgaccaaa cagcttctca   2880
tctgttattc agaataattc ctcgatggca ggatatccat cccaattggg ggaaggggag   2940
aatttgaaga aaacctagac cacatacata tttgccattg ggaaacaaag tctaaaatga   3000
tgttgttcac atcttctcta ctagtcctct ccccgtccca aagaaccttg gtatatgtgc   3060
ctcattttac agagagagga aagcaggaac tgagcatccc ttacttgcca tcctcaaccc   3120
aaaatttgca tcattgctca gctctgccct tctcatatga cagttacaag tcaaggcttc   3180
caaagtccct ctgtcatgtt tggtgtcaat agtttataca gatgacttca tgtcttcata   3240
tctaatgtct tatatagatt aatattaaac aatgttattt ctctaaccac attttaaatt   3300
aatttaaaaa tccattaatt gtgtctataa aatgcagaca gagtgctgag acacaatata   3360
agcctgatga tctgaatttg aaactcacac ccaccacatg gagaatcaac ttccaaaaat   3420
```

-continued

```
tttcctatta cttccacact tacaccattg tacaaacaca ataataatga acaaaatgaa   3480

atgaaataaa aaattaagtc tctgtaggta atgctactgt gcagcaaaag taaaaatggc   3540

agcttaagct tgctttatgg ttacacttta ccatcttcca ttaattataa ggacttcaat   3600

catggcagaa ctatgctgtt attgtctcag tgtaacctaa ccaggtgttc cagatgttct   3660

taatgtggac acctaaacta tttgatattt gggttaagat ctttccctct ttcagaagaa   3720

acctcaggac agagggaatc ttgtctttta attttgagtc tgtagacttt ttccatttca   3780

aatatacatg aaacaagtga tgaagaaaat taatcaaaag gtgggaattg caatgatatt   3840

aggttcaata ttaagcttca atattatcat ggaatcgcct gttatacact gagtgtttgg   3900

caataaggga tttttagaag aaggagtttt tattctcaac aggttcctta agtttagctc   3960

aaataaatct aagcaatcca ctctagaatt aaatagtttc c                       4001
```